United States Patent
Wang et al.

(10) Patent No.: US 10,617,706 B2
(45) Date of Patent: Apr. 14, 2020

(54) COMPOUNDS FOR CANCER CHEMOTHERAPEUTIC SENSITIZATION

(71) Applicants: Regents of the University of Minnesota, Minneapolis, MN (US); THE USA, AS REPRESENTED BY THE SECRETARY, DEPT. OF HEALTH AND HUMAN SERVICES, Bethesda, MD (US)

(72) Inventors: Zhengqiang Wang, Minneapolis, MN (US); Jayakanth Kankanala, Minneapolis, MN (US); Yves Pommier, Rockville, MD (US)

(73) Assignees: REGENTS OF THE UNIVERSITY OF MINNESOTA, Minneapolis, MN (US); THE USA, AS REPRESENTED BY THE SECRETARY, DEPT. OF HEALTH AND HUMAN SERVICES, Bethesda, MD (US)

(*) Notice: Subject to any disclaimer, the term of this patent is extended or adjusted under 35 U.S.C. 154(b) by 0 days.

(21) Appl. No.: 16/267,274

(22) Filed: Feb. 4, 2019

(65) Prior Publication Data
US 2019/0240244 A1 Aug. 8, 2019

Related U.S. Application Data

(60) Provisional application No. 62/730,470, filed on Sep. 12, 2018, provisional application No. 62/626,520, filed on Feb. 5, 2018.

(51) Int. Cl.
| | |
|---|---|
| C07D 401/14 | (2006.01) |
| A61K 31/7068 | (2006.01) |
| A61P 35/00 | (2006.01) |
| A61K 45/06 | (2006.01) |
| A61K 9/20 | (2006.01) |
| C07D 471/04 | (2006.01) |

(Continued)

(52) U.S. Cl.
CPC ........ *A61K 31/7068* (2013.01); *A61K 9/0019* (2013.01); *A61K 9/12* (2013.01); *A61K 9/1611* (2013.01); *A61K 9/1623* (2013.01); *A61K 9/1652* (2013.01); *A61K 9/2018* (2013.01); *A61K 9/2027* (2013.01); *A61K 9/2054* (2013.01); *A61K 9/2059* (2013.01); *A61K 45/06* (2013.01); *A61K 47/02* (2013.01); *A61K 47/10* (2013.01); *A61K 47/12* (2013.01); *A61P 35/00* (2018.01); *C07D 471/04* (2013.01); *C07F 5/02* (2013.01)

(58) Field of Classification Search
CPC .................................................. C07D 401/14
See application file for complete search history.

(56) References Cited

U.S. PATENT DOCUMENTS

| | | |
|---|---|---|
| 9,402,842 B2 | 8/2016 | Cushman et al. |
| 2018/0009822 A1 | 1/2018 | An et al. |

OTHER PUBLICATIONS

Raoof et al. (Journal of Medicinal Chemistry (2013), 56(16), 6352-6370).*

(Continued)

*Primary Examiner* — Bruck Kifle
(74) *Attorney, Agent, or Firm* — Viksnins Harris Padys Malen LLP

(57) ABSTRACT

The invention provides a compound of formula (I), (II) or (III):

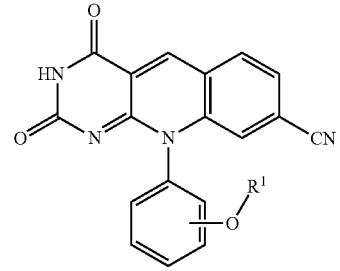

(I)

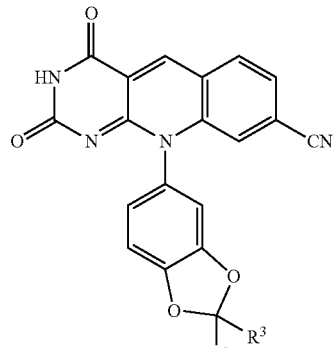

(II)

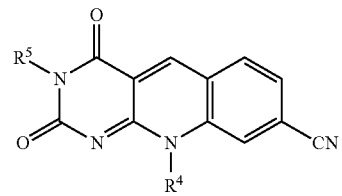

(III)

wherein $R^1$, $R^2$, $R^3$, $R^4$ and $R^5$ have any of the values described in the specification, as well as compositions comprising a compound of formula (I), (II) or (III). The compounds and compositions are useful as chemotherapeutic sensitizing agents.

17 Claims, 3 Drawing Sheets

(51) Int. Cl.
*A61K 9/16* (2006.01)
*A61K 9/00* (2006.01)
*A61K 47/10* (2017.01)
*C07F 5/02* (2006.01)
*A61K 9/12* (2006.01)
*A61K 47/12* (2006.01)
*A61K 47/02* (2006.01)

(56) References Cited

OTHER PUBLICATIONS

Dickens et al. (Bioorganic & Medicinal Chemistry (2013), 21(22), 6868-6877).*
Baell, J , et al., "New Substructure Filters for Removal of Pan Assay Interference Compounds (PAINS) from Screening Libraries and for Their Exclusion in Bioassays", J Med Chem 53, 2719-2740 (2010).
Do, P , et al., "Mutant p53 cooperates with ETS2 to promote etoposide resistance", Genes Dev 26(8), 830-845 (2012).
Gao, R , et al., "Biochemical Characterization of Human Tyrosyl-Dna Phosphodiesterase 2 (TDP2/TTRAP) a Mg2+/Mn2+-Dependent Phosphodiesterase Specific for the Repair of Topoisomerase Cleavage Complexes", J Biol Chem 287, 30842-30852 (2012).
Gomez-Herreros, F , et al., "TDP2 protects transcription from abortive topoisomerase activity and is required for normal neural function", Nat Genet 46, 516-521 (2014).
Gomez-Herreros, F , et al., "TDP2—Dependent Non-Homologous End-Joining Protects against Topoisomerase II—Induced DNA Breaks and Genome Instability in Cells and In Vivo", PLoS Genet 9 (3), e100226, 15 pages (2013).
Hornyak, P , et al., "Mode of action of DNA-competitive small molecule inhibitors of tyrosyl DNA phosphodiesterase 2", Biochem J 473, 1869-1879 (2016).
Laev, S , et al., "Tyrosyl-DNA phosphodiesterase inhibitors: Progress and potential", Bioorg Med Chem 24, 5017-5027 (2016).
Ledesma, F , et al., "A human 5'-tyrosyl DNA phosphodiesterase that repairs topoisomerase-mediated DNA damage", Nature 461, 674-678 (2009).
Maede, Y , "Differential and Common DNA Repair Pathways for Topoisomerase I- and II-Targeted Drugs in a Genetic DT40 Repair Cell Screen Panel", Mol Cancer Ther 13, 214-220 (2014).
Marchand, C , et al., "Deazaflavin Inhibitors of Tyrosyl-DNA Phosphodiesterase 2 (TDP2) Specific for the Human Enzyme and Active against Cellular TDP2", ACS Chem Biol 11, 1925-1933 (2016).
Schellenberg, M , et al., "Mechanism of repair of 5'-topoisomerase II—DNA adducts by mammalian tyrosyl-DNA phosphodiesterase 2", Nat Struct Mol Biol 19, 1363-1371 (2012).
Shi, K , et al., "Structural basis for recognition of 5'-phosphotyrosine adducts by TDP2", Nat Struct Mol Biol 19, 1372-1377 (2012).
Wang, P , "Synthesis and Biological Evaluation of the First Triple Inhibitors of Human Topoisomerase 1, Tyrosyl—DNA Phosphodiesterase 1 (Tdp1), and Tyrosyl—DNA Phosphodiesterase 2 (Tdp2)", Journal of Medicinal Chemistry 60 (8), 3275-3288 (2017).
Zeng, Z , et al., "TDP2/TTRAP is the Major 5'-Tyrosyl DNA Phosphodiesterase Activity in Vertebrate Cells and is Critical for Cellular Resistance to Topoisomerase II-induced DNA Damage", J Biol Chem 286, 403-409 (2011).

* cited by examiner

Figures 1A-1C
Figure 1A
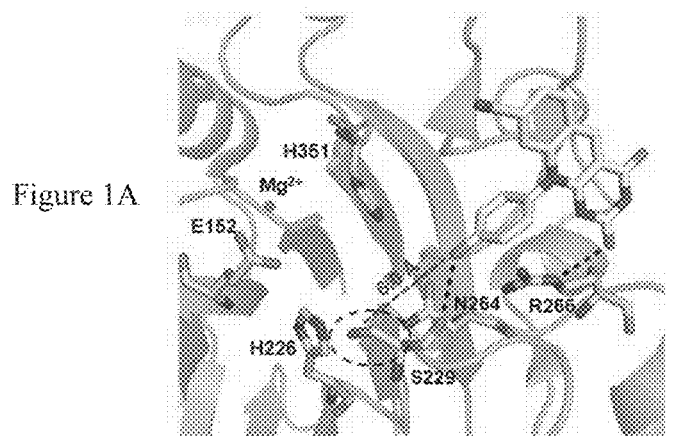
Figure 1B
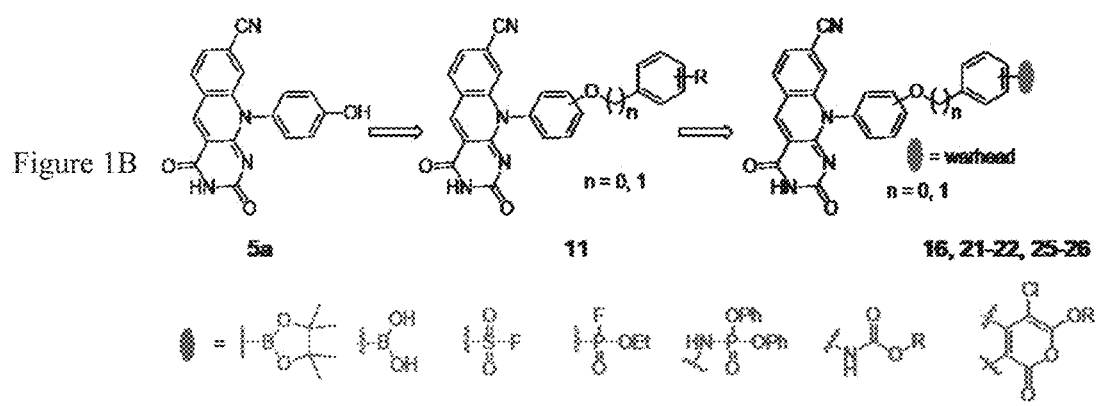
Figure 1C
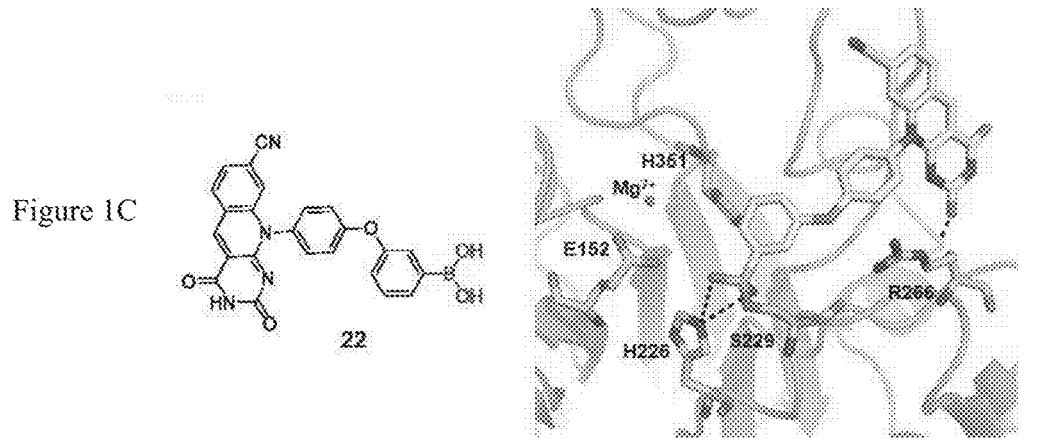

Figures 2A-2B
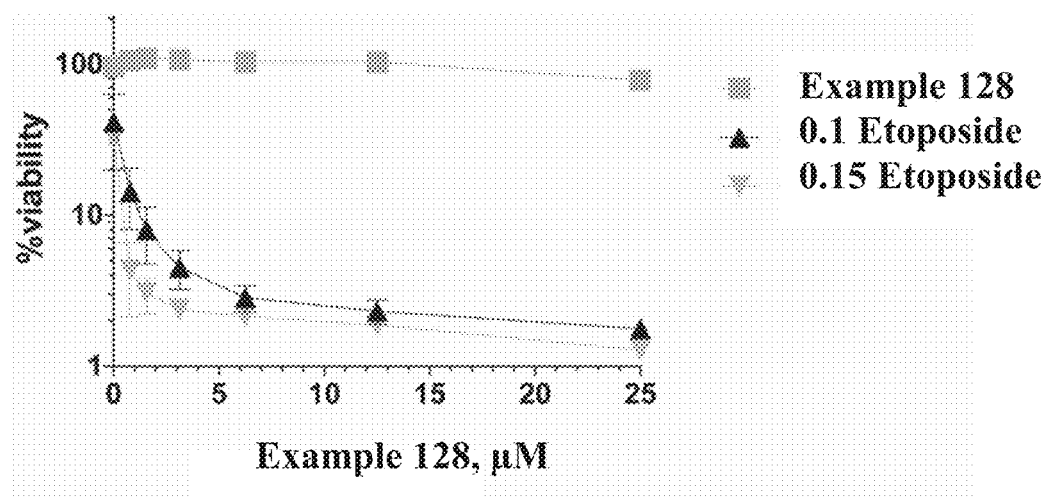
Figure 2A
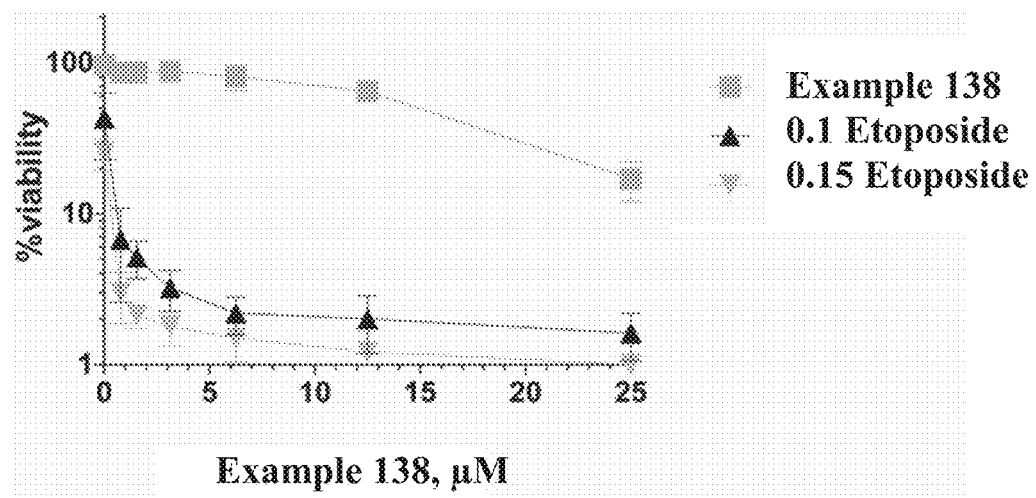
Figure 2B

Figures 2C-2D
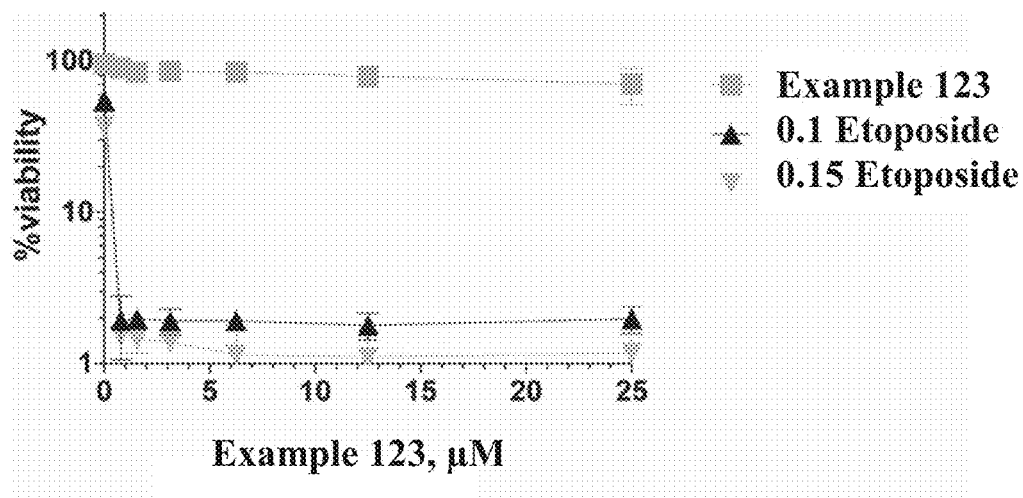
Figure 2C
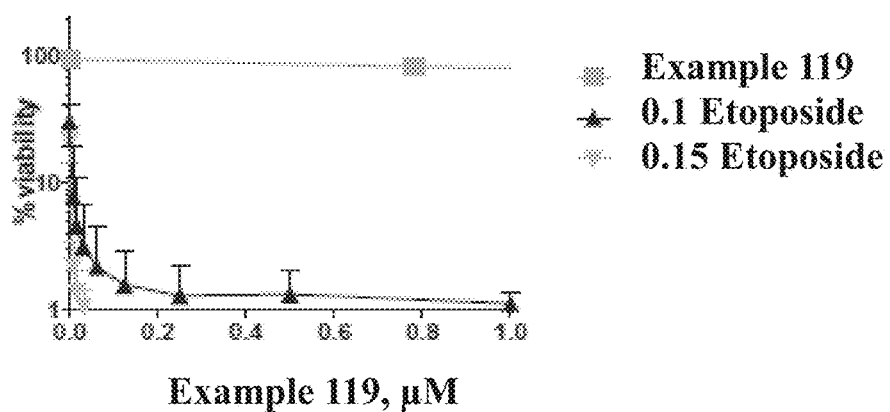
Figure 2D

COMPOUNDS FOR CANCER CHEMOTHERAPEUTIC SENSITIZATION

RELATED APPLICATIONS

This Application claims the benefit of priority to U.S. Provisional Patent Application No. 62/730,470, filed 12 Sep. 2018, and also claims the benefit of priority of U.S. Provisional Patent Application No. 62/626,520, filed 5 Feb. 2018. The entire content of the applications referenced above are hereby incorporated by reference herein.

BACKGROUND OF THE INVENTION

Topoisomerases are ubiquitous cellular enzymes required for controling DNA topology during DNA synthesis by removing free supercoiling. On the molecular level, topoisomerase II (Top2) cuts both strands of DNA duplex using its tyrosine residue to generate transient double-strand breaks (DSBs) and form the Top2 cleavage complex, in which Top2 is covalently linked to the 5'terminus of the DSB via a tyrosyl phosphodiester bond. Continuous DNA transcription and replication requires a re-ligation of the DSB at the end of each catalytic cycle such that a dynamic equilibrium is established between DNA and the Top2cc. However, when the transient Top2 cleavage occurs near a pre-existing DNA damage the re-ligation is stalled and the cleavage complex becomes abortive. Clinically important Top2 poisons work by this mechanism as they bind to and stabilize the Top2cc to prevent re-ligation, resulting in the accumulation of abortive Top2cc. Such DNA damages are often repaired by cellular DNA repair enzymes.

Tyrosyl-DNA phosphodiesterase II (TDP2), a DNA repair enzyme, specifically repairs Top2-mediated DNA damages, including the abortive Top2cc trapped by Top2 poisons (Ledesma, F. C., et al., *Nature* 2009, 461, 674-U125). As a result, the normal cellular function of TDP2 renders cancer cells resistant to Top2 poisons, a major class of drugs widely used to treat cancers such as testicular cancer, lung cancer, lymphoma, leukemia, neuroblastoma, and ovarian cancer. This is supported by observations both in cultured cells and animal models that the lack of TDP2 leads to enhanced cellular sensitivity to DNA breaks induced by Top2 poisons (Ledesma, F. C., et al., *Nature* 2009, 461, 674-U125; Zeng, Z. H., et al., *J. Biol. Chem.* 2011, 286, 403-409; Gomez-Herreros, F., et al., *Nat. Genet.* 2014, 46, 516-521; Gomez-Herreros, F., et al., *PLoS Genet.* 2013, 9, e1003226; and Maede, Y., et al., *Mol. Cancer. Ther.* 2014, 13, 214-20). Importantly, up-regulation of TDP2 transcription through a gain-of-function p53 mutation has indeed been linked to Top2 poison resistance in human lung cancer (Do, P. M., et al., *Genes Dev.* 2012, 26, 830-45). These observations strongly suggest that inhibiting TDP2 could sensitize cancer cells towards clinical Top2 poisons.

TDP2 inhibition, however, is underexplored and poorly understood. Since its discovery in 2009 (Ledesma, F. C., et al., *Nature* 2009, 461, 674-U125), efforts in biochemistry and crystallography have generated critical knowledge to allow basic understanding on TDP2 active site, mode of substrate recognition, enzyme kinetics, and mechanism of catalysis (Gao, R., et al., *J. Biol. Chem.* 2012, 287, 30842-30852; Schellenberg, M. J., et al., *Nat. Struct. Mol. Biol.* 2012, 19, 1363-1371; and Shi, K., et al., *Nat. Struct. Mol. Biol.* 2012, 19, 1372-1377). These studies support a single-metal catalytic mechanism characteristic of the exonuclease-endonuclease-phosphatase (EEP) nuclease superfamily. According to this mechanism, TDP2 cleaves the 5' phosphotyrosine adduct through a hydrolytic reaction promoted by one $Mg^{2+}$ ion and a few key residues at active site. Particularly important to catalysis are residues D262, E152, H351 and S229, as single mutation of any of them was shown to abrogate the catalytic activity of hTDP2 (Schellenberg, M. J., et al., *Nat. Struct. Mol. Biol.* 2012, 19, 1363-1371). Importantly, crystal structures of TDP2 bound to DNA substrates revealed a deep, narrow groove that selectively accommodates the 5' end of single-stranded DNA (Withoff, S., et al., *Anticancer Res.* 1996, 16, 1867-1880 and Shi, K., et al., *Nat. Struct. Mol. Biol.* 2012, 19, 1372-1377). Nevertheless, efforts in TDP2 inhibition to date have been largely limited to random screening of compound libraries using biochemical assays (Laev, S., et al., *Bioorg. Med. Chem.* 2016, 24, 5017-5027). Hits generated typically lack desired drug like properties and fit the profiles of pan-assay interference structure (PAINS) (Baell, J. B., et al. *J. Med. Chem.* 2010, 53, 2719-2740).

Certain specific compounds that were identified through a high-throughput-screening (HTS), selectively inhibited hTDP2 in nanomolar range, presumably by occupying the DNA binding groove of TDP2 and blocking DNA substrates from coming into TDP2 active site (Raoof, A., et al., *J. Med. Chem.* 2013, 56, 6352-6370; and Hornyak, P., et al., *Biochem. J.* 2016, 473, 1869-1879). However, these biochemical inhibitors show only weak efficacy in cancer cells (Marchand, C., et al., *ACS Chem. Biol.* 2016, 11, 1925-1933).

Currently, there is a need for TDP2 inhibitors (e.g. improved TDP2 inhibitors) that are effective in sensitizing cancer cells to allow Top2 poisons to be used at lower and safer doses.

SUMMARY OF THE INVENTION

The invention provides compounds that are effective to sensitize cancer cells. Representative compounds showed efficacy as sensitizing agents in cancer cell lines. Compounds of the invention can be used along with Top2 poisons (e.g. etoposide, teniposide, doxonibicin, or daunorubicin) to treat cancer.

Accordingly, in one embodiment the invention provides a compound of the invention that is a compound of formula (I), (II) or (III):

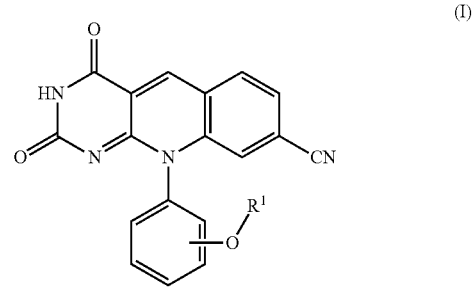

-continued

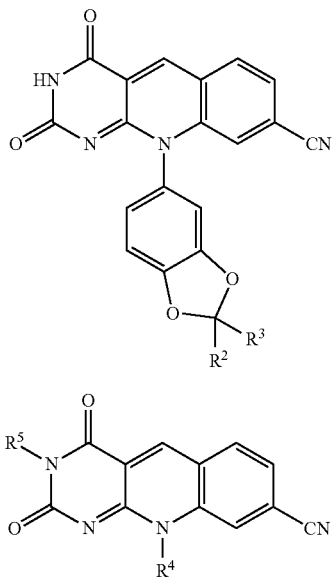

(II)

(III)

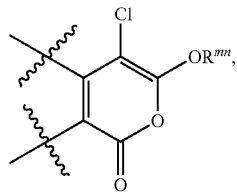

wherein:

R¹ is phenyl, benzyl, or $(C_1-C_3)$alkyl optionally substituted with halo, wherein the phenyl or benzyl is optionally substituted with one or more groups $R^x$ that are independently selected from the group consisting of halo, carboxy, $(C_1-C_6)$alkoxycarbonyl, halo$(C_1-C_6)$alkoxycarbonyl, —C(=O)NR$^b$R$^c$, —NHP(=O)(OR$^d$)(OR$^e$), —NHC(=O)OR$^f$, —B(OR$^g$)(OR$^h$), —S(O)$_2$F, —P(=O)(F)(OR$^k$),

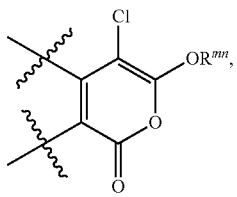

and $(C_1-C_3)$alkyl substituted with halo, $(C_1-C_6)$alkoxycarbonyl, halo$(C_1-C_6)$alkoxycarbonyl, —C(=O)NR$^b$R$^c$, —NHP(=O)(OR$^d$)(OR$^e$), —NHC(=O)OR$^f$, —B(OR$^g$)(OR$^h$), —S(O)$_2$F, or —P(=O)(F)(OR$^k$);

R$^b$ and R$^c$ are each independently H or $(C_1-C_6)$alkyl;

R$^d$ and R$^e$ are each independently H, $(C_1-C_6)$alkyl, or phenyl;

R$^f$ is H, $(C_1-C_6)$alkyl, or phenyl;

R$^g$ and R$^h$ are each independently H or $(C_1-C_6)$alkyl, or R$^g$ and R$^h$ taken together with the boron and oxygens to which they are attached form a 5- or 6-membered ring that is optionally substituted with one or more groups independently selected from $(C_1-C_6)$alkyl;

R$^k$ is $(C_1-C_6)$alkyl; and

R$^{mn}$ is H, $(C_1-C_6)$alkyl, or phenyl;

R² and R³ are each independently selected from H, halo or $(C_1-C_6)$alkyl that is optionally substituted with halo;

R⁴ is phenyl, wherein the phenyl is optionally substituted with one or more groups $R^{xx}$ that are independently selected from the group consisting of halo, carboxy, —OH, —OR$^i$, $(C_1-C_6)$alkoxycarbonyl, halo$(C_1-C_6)$alkoxycarbonyl, —C(=O)NR$^m$R$^n$, —NHP(=O)(OR$^p$)(OR$^q$), —NHC(=O)OR$^s$, —NHS(O)$_2$R$^{ss}$, —B(OR$^t$)(OR$^u$), —S(O)$_2$F, —P(=O)(F)(OR$^v$), and $(C_1-C_3)$alkyl optionally substituted with halo, $(C_1-C_6)$alkoxycarbonyl, halo$(C_1-C_6)$alkoxycarbonyl, —C(=O)NR$^m$R$^n$, —N—P(=O)(OR$^p$)(OR$^q$), —NHC(=O)OR$^s$, —B(OR$^t$)(OR$^u$), —S(O)$_2$F, or —P(=O)(F)(OR$^v$);

R$^m$ and R$^n$ are each independently H or $(C_1-C_6)$alkyl;

R$^p$ and R$^q$ are each independently H, $(C_1-C_6)$alkyl, or phenyl;

R$^s$ is H, $(C_1-C_6)$alkyl, or phenyl;

R$^{ss}$ is $(C_1-C_6)$alkyl, or phenyl;

R$^t$ and R$^u$ are each independently H or $(C_1-C_6)$alkyl, or R$^t$ and R$^u$ taken together with the boron to which they are attached form a 5- or 6-membered ring that is optionally substituted with one or more groups independently selected from $(C_1-C_6)$alkyl;

R$^v$ is $(C_1-C_6)$alkyl; and

R⁵ is $(C_1-C_6)$alkyl or phenyl, wherein the alkyl or phenyl is optionally substituted with one or more groups that are independently selected from the group consisting of halo, $(C_1-C_6)$alkoxycarbonyl, —NHP(=O)(OR$^w$V)(OR$^y$), —C(=O)NR$^z$R$^{aa}$, —NHC(=O)OR$^{bb}$, carboxy, or $(C_1-C_3)$alkyl substituted with —NHP(=O)(OR$^w$)(OR$^y$);

R$^z$ and R$^{aa}$ are each independently H or $(C_1-C_6)$alkyl;

R$^w$ and R$^y$ are each independently H, $(C_1-C_6)$alkyl, or phenyl; and

R$^{bb}$ is H, $(C_1-C_6)$alkyl, or phenyl;

or a salt thereof.

The invention also provides a pharmaceutical composition comprising a compound of formula (I), (II), (III) or a pharmaceutically acceptable salt thereof, and a pharmaceutically acceptable excipient.

The invention also provides a pharmaceutical composition comprising, 1) a compound of formula (I), (II), (III) or a pharmaceutically acceptable salt thereof, 2) a chemotherapeutic agent (e.g. a Top2 poison), and 3) a pharmaceutically acceptable excipient.

The invention also provides a method for sensitize a cancer cell toward therapy comprising contacting the cell with a compound of formula (I), (II), (III) or a pharmaceutically acceptable salt thereof.

The invention also provides a method for treating cancer in an animal (e.g., a mammal such as a human) comprising administering, 1) a compound of formula (I), (II), (III) or a pharmaceutically acceptable salt thereof, and 2) a chemotherapeutic agent (e.g. a Top2 poison) to the animal.

The invention also provides a compound of formula (I), (II), (III) or a pharmaceutically acceptable salt thereof for use in medical therapy.

The invention also provides a compound of formula (I), (II), (III) or a pharmaceutically acceptable salt thereof for the prophylactic or therapeutic treatment of cancer, in combination with a chemotherapeutic agent (e.g. a Top2 poison).

The invention also provides the use of a compound of formula (I), (II), (III) or a pharmaceutically acceptable salt thereof to prepare a medicament for treating cancer in an animal (e.g. a mammal such as a human), in combination with a chemotherapeutic agent (e.g. a Top2 poison).

The invention also provides processes and intermediates disclosed herein that are useful for preparing a compound of formula (I), (II), (III) or a salt thereof.

BRIEF DESCRIPTION OF TIRE FIGURES

FIGS. 1A-1C illustrates structure-guided design of dual mechanism TDP2 inhibitors combining deazaflavin 5a and a warhead. (FIG. 1A) Crystal structure of deazaflavin 5a bound TDP2. The phenolic hydroxyl group of 5a is pointing toward S229 with a distance of 6.0 A; (FIG. 1B) Dual mechanism inhibitors 16, 21-22, 25-26 are designed with the introduction of a typical warhead for serine trapping; (FIG. 1C) docking of 22 validates the design.

FIGS. 2A-2D shows data for representative compounds of the invention from Example 128 (FIG. 2A), efficacy in DT40 cells: Squares: TDP2 inhibitor alone should not kill cancer cells; Triangles TDP2 inhibitor in combination with 0.1 μM ETP; Inverted Triangles: TDP2 inhibitor in combination with 0.15 μM ETP. Example 138 (FIG. 2B), efficacy in DT40 cells: Squares: TDP2 inhibitor alone should not kill cancer cells; Triangles TDP2 inhibitor in combination with 0.1 μM ETP; Inverted Triangles: TDP2 inhibitor in combination with 0.15 μM ETP. Example 123 (FIG. 2C), efficacy in DT40 cells: Squares: TDP2 inhibitor alone should not kill cancer cells; Triangles TDP2 inhibitor in combination with 0.1 μM ETP; Inverted Triangles: TDP2 inhibitor in combination with 0.15 μM ETP. Example 119 (FIG. 2D), efficacy in DT40 cells: Squares: TDP2 inhibitor alone should not kill cancer cells; Triangles TDP2 inhibitor in combination with 0.1 μM ETP; Inverted Triangles: TDP2 inhibitor in combination with 0.15 μM ETP.

DETAILED DESCRIPTION

A recently resolved co-crystal structure (Hornyak, P., et al., *Biochem. J.* 2016, 473, 1869-1879) of deazaflavin analogue 5a with hTDP2 revealed that when occupying the DNA binding groove the phenolic hydroxyl group of 5a is pointing toward S229 with a distance of 6 Å (FIG. 1A). The phenolic hydroxyl group and its positioning offer a handle to chemically attach an electrophilic warhead for serine trapping. Arylation of this phenolic hydroxyl group resulted in compounds (12a-c), which retained potent inhibition against TDP2 (FIG. 1B), suggesting that such modifications are tolerated. Based on this, dual mechanism inhibitors (13) featuring an electrophilic warhead (e.g. a serine trapping fragment) (FIG. 1C) were designed (Shannon, D. A., et al., *Curr. Opin. Chem. Biol.* 2015, 24, 18-26). The design was validated in silico through covalent docking of a 22 (warhead=3-B(OH)$_2$, FIG. 1C) (see Zhu K, B. K., et al., *J Chem Inf Model.* 2014, 54, 1932-1940; and Dora Toledo Warshaviak, et al., *J. Chem. Inf. Model.* 2014, 54, 1941-1950).

The following definitions are used, unless otherwise described: halo or halogen is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include ($C_1$-$C_8$)alkyl, ($C_2$-$C_8$)alkyl, ($C_1$-$C_6$)alkyl, ($C_2$-$C_6$)alkyl and ($C_3$-$C_6$)alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and and higher homologs and isomers.

The term "alkoxycarbonyl" as used herein refers to a group (alkyl)-O—C(=O)—, wherein the term alkyl has the meaning defined herein.

The term "halo($C_1$-$C_6$)alkoxycarbonyl" as used herein refers to a group ($C_1$-$C_6$alkyl)-O—C(=O)—, wherein the $C_1$-$C_6$alkyl is substituted with one or more halo groups.

The term "serine trapping group includes mechanism based electrophiles that covalently react with the serine nucleophile in the active site (J C Powers., et al., *Chem. Rev,* 2002, 102, 4639-4750 and Bachovchin, D A., *Nat Rev Drug Discov.* 2012, 11, 52-68). Examples of serine trapping groups include carbamates, ureas, activated ketones, lactams, lactones, sulfonyl fluorides, isocoumatins, benzoxazinones, saccharins, nitriles, boronic acids, phosphoramidates, and phosphonyl fluorides (J C Powers., et al., *Chem, Rev.* 2002, 102, 4639-4750).

As used herein a wavy line "⁓" that intersects a bond in a chemical structure indicates the point of attachment of the bond that the wavy bond intersects in the chemical structure to the remainder of a molecule.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention.

The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

The pharmaceutical compositions of the invention can comprise one or more excipients. When used in combination with the pharmaceutical compositions of the invention the term "excipients" refers generally to an additional ingredient that is combined with the compound of formula (I), (II), (III) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

The term "residue" as it applies to the residue of a compound refers to a compound that has been modified in any manner which results in the creation of an open valence wherein the site of the open valence. The open valence can be created by the removal of 1 or more atoms from the compound (e.g., removal of a single atom such as hydrogen or removal of more than one atom such as a group of atoms including but not limited to an amine, hydroxyl, methyl, amide (e.g., —C(=O)NH$_2$) or acetyl group). The open valence can also be created by the chemical conversion of a first function group of the compound to a second functional group of the compound (e.g., reduction of a carbonyl group, replacement of a carbonyl group with an amine,) followed by the removal of 1 or more atoms from the second functional group to create the open valence.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Specifically, (C$_1$-C$_6$)alkyl can be methyl, ethyl, propyl, isopropyl, butyl, iso-butyl, sec-butyl, pentyl, 3-pentyl, or hexyl; and (C$_1$-C$_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl.

A specific compound of formula (I) is a compound of formula (Ia):

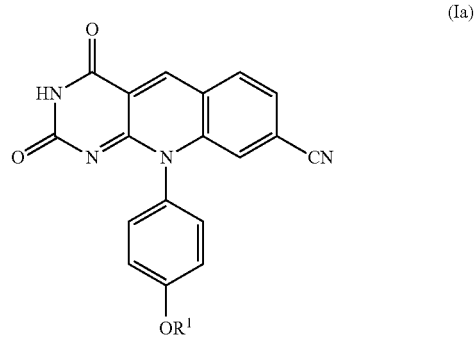

A specific compound of formula (I) is a compound of formula (Ib):

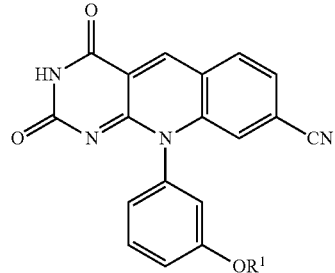

(Ib)

A specific compound of formula (I) is a compound of formula (Ic):

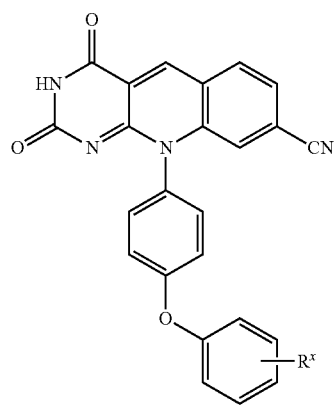

(Ic)

A specific compound of formula (I) is a compound of formula (Id):

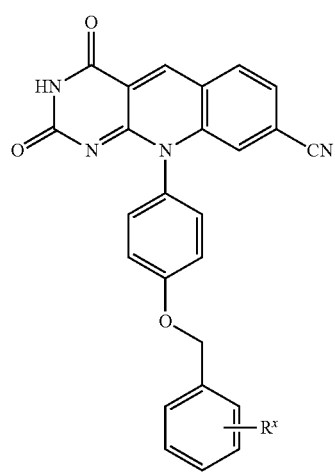

(Id)

A specific compound of formula (I) is a compound of formula (Ia), wherein $R^1$ is phenyl that is substituted with

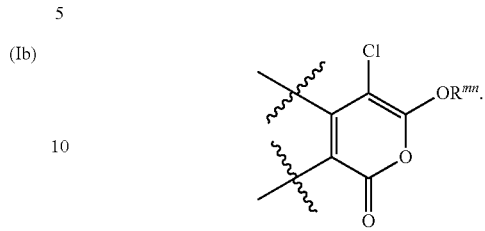

A specific compound of formula (I) is a compound of formula (Ia), wherein $R^1$ is benzyl that is substituted with

A specific value of $R^x$ is bromo, chloro, fluoro, methoxycarbonyl, aminocarbonyl, —NHP(=O)(OPh)(OPh), —CH$_2$—NHP(=O)(OPh)(OPh), —NHC(=O)OPh, —B(OH)(OH), and

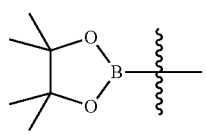

A specific value of $R^x$ is fluoro, bromo, and chloro.

A specific compound or salt is selected from the group consisting of:

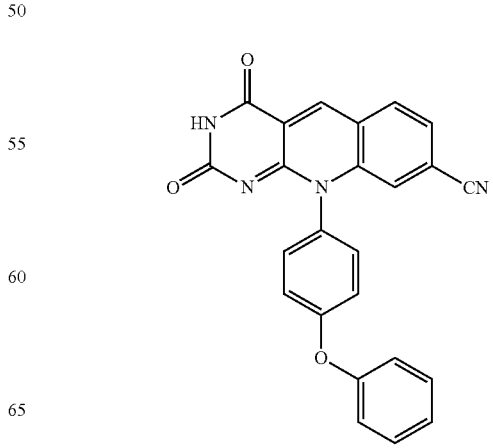

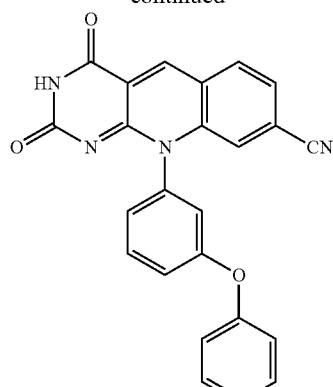
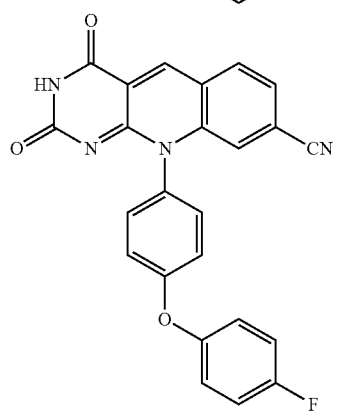
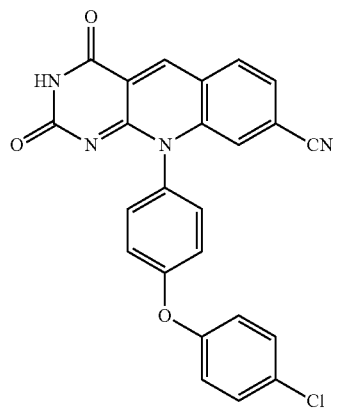
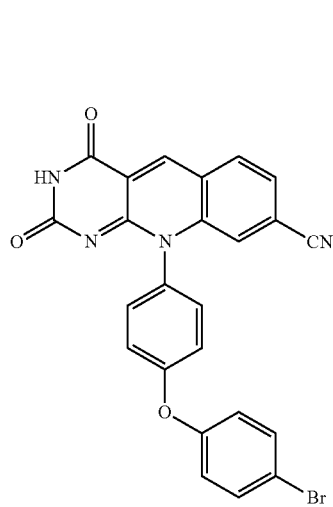
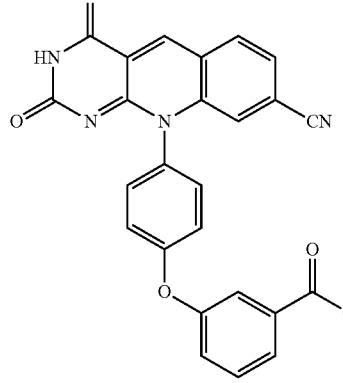
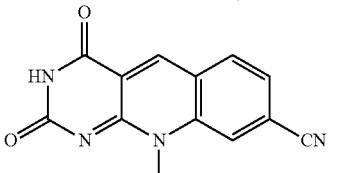
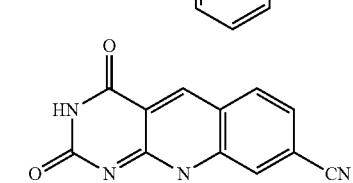
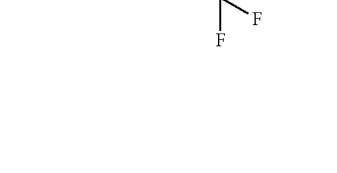

-continued
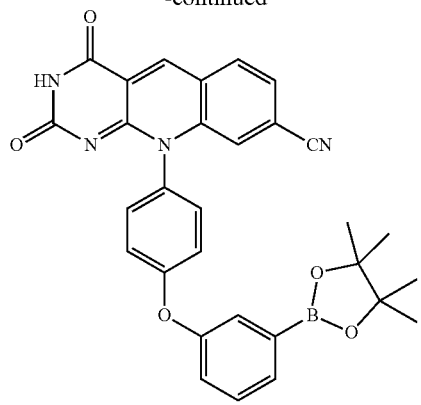
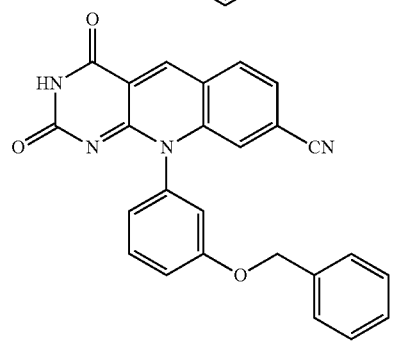
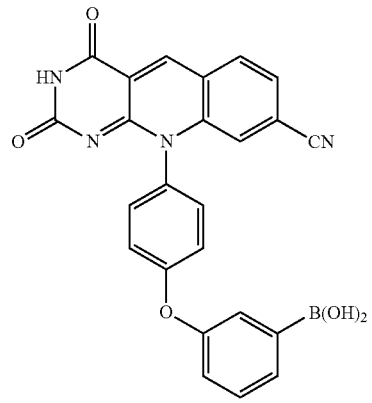
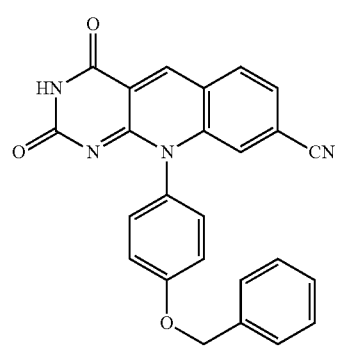
-continued
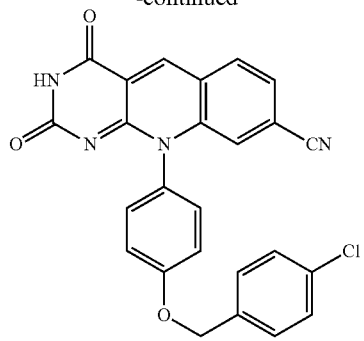
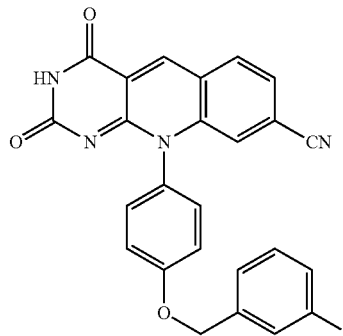
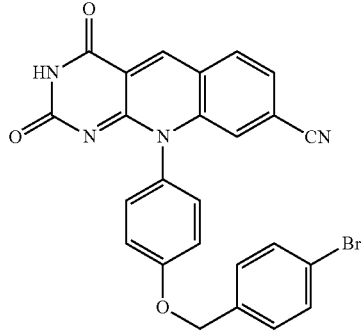
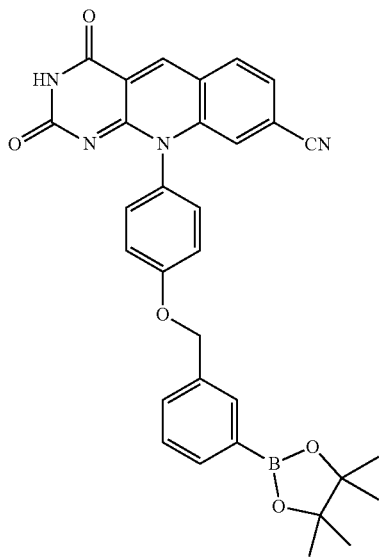

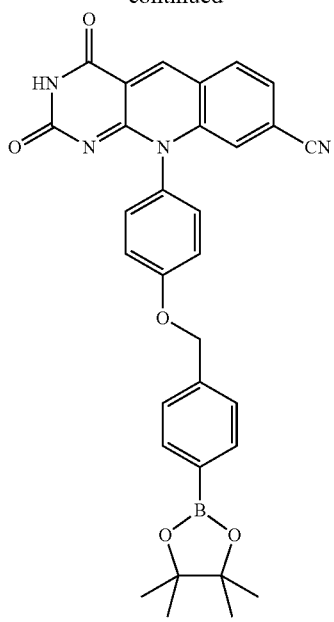
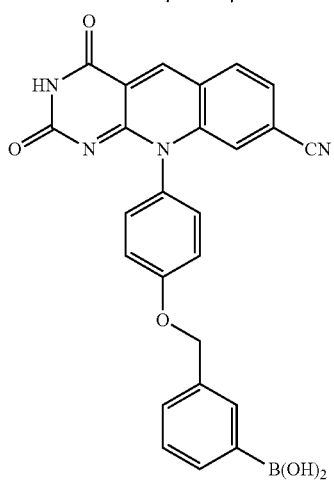
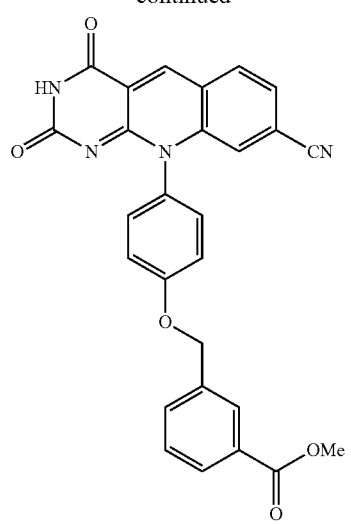
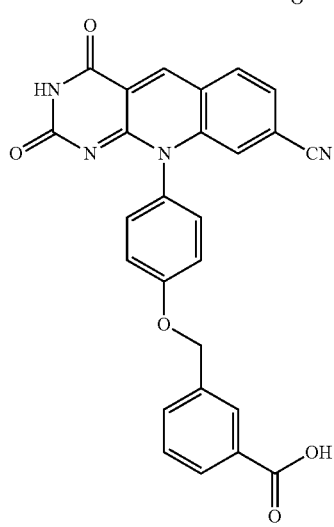
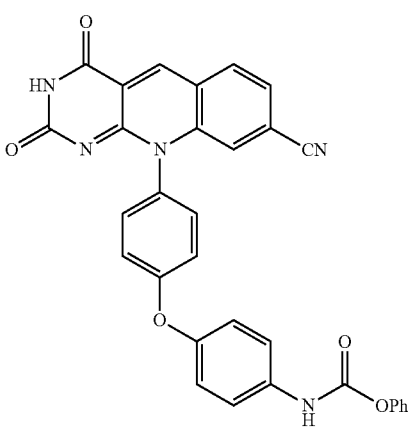 [SMILES: N#Cc1ccc2cc3c(=O)[nH]c(=O)nc-3n(-c3ccc(Oc4ccc(NC(=O)Oc5ccccc5)cc4)cc3)c2c1]
and salts thereof.
A specific value of $R^2$ is H or halo.
A specific value of $R^3$ is H or halo.
A specific compound of formula (II) of salt thereof is selected from the group consisting of:

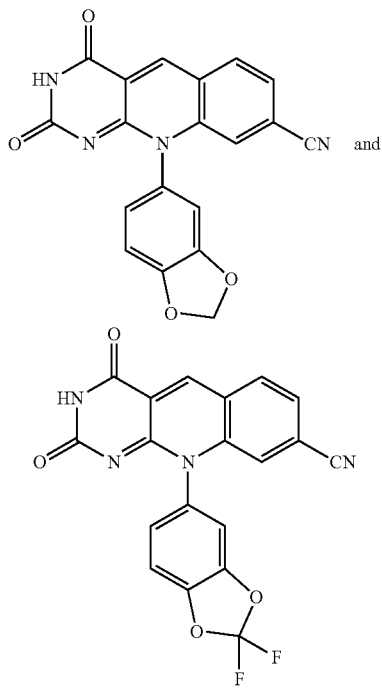

and a salt thereof.

A specific compound of formula (III) is a compound of formula (IIIa):

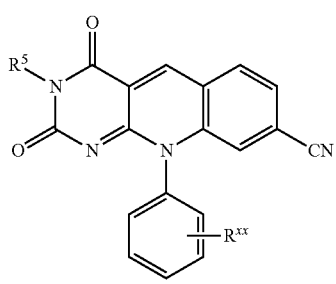
(IIIa)

A specific compound of formula (III) is a compound of formula (IIIb):

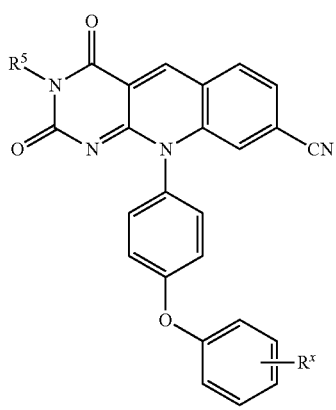
(IIIb)

A specific value for $R^{xx}$ is H, OH, —NHS(O)$_2$Me and —B(OH)$_2$.

A specific value for $R^4$ is phenyl, 4-hydroxyphenyl, 3-hydroxyphenyl, 3-methylsulfonylaminophenyl, 4-methylsulfonylaminophenyl, or 4-(3-boronophenoxy)phenyl.

A specific value for $R^5$ is $(C_1-C_6)$alkyl.

A specific value for $R^5$ is methyl.

A specific value for $R^5$ is phenyl optionally substituted with one or more groups that are independently selected from the group consisting of halo, carboxy, $(C_1-C_6)$alkoxycarbonyl, —NHP(=O)(OPh)(OPh), —C(=O)NH$_2$, —NHC(=O)OPh, and $(C_1-C_3)$alkyl substituted with —NHP(=O)(OPh)(OPh).

A specific value for $R^5$ is methyl, phenyl, 4-chlorophenyl, 3-chlorophenyl, 3,4-dichlorophenyl, 4-fluorophenyl, 3-methoxycarbonylphenyl, 4-bromophenyl, 3-aminocarbonylphenyl, 3-phenoxycarbonylamino, 4-phenoxycarbonylamino,

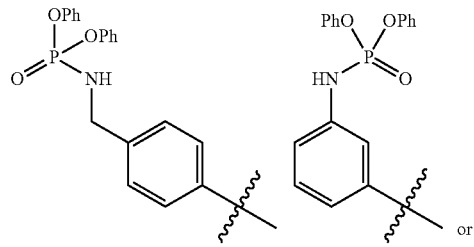
or

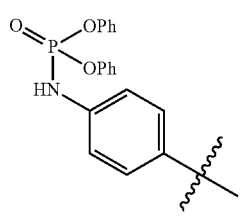

A specific compound or salt is selected from the group consisting of:

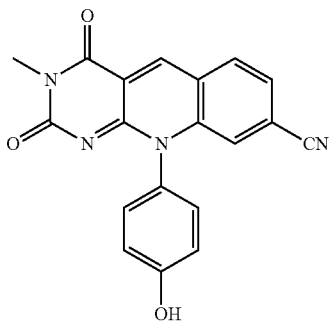

-continued
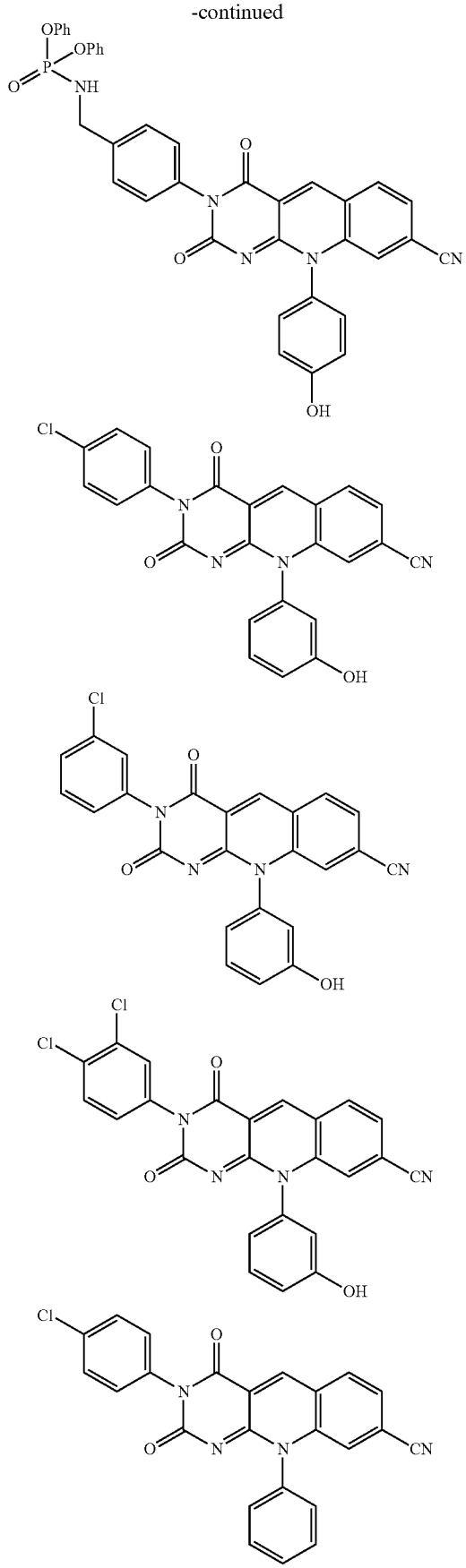
-continued
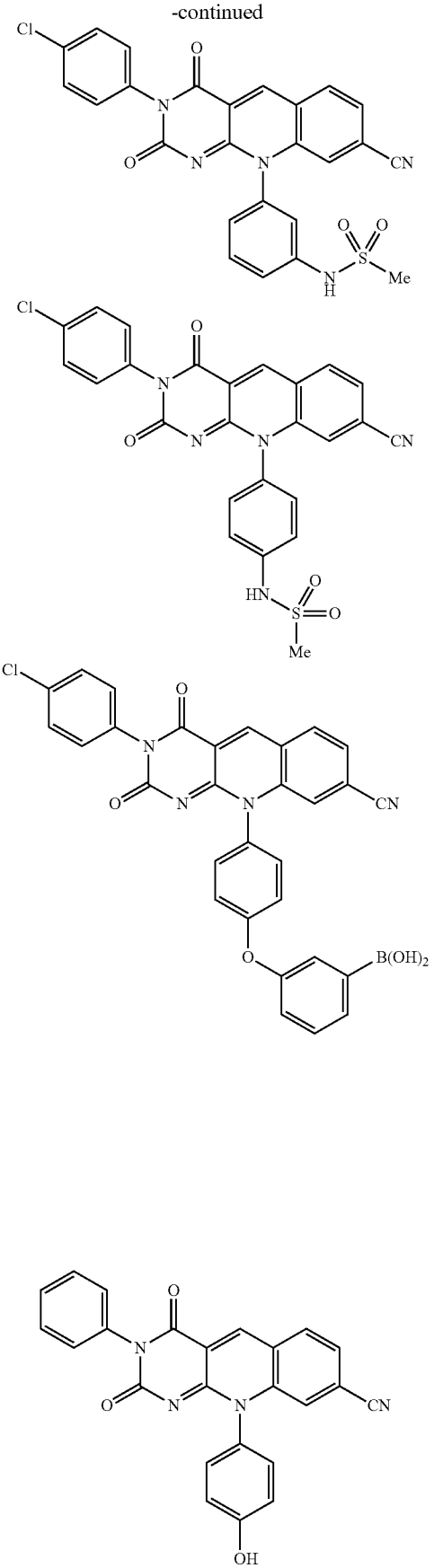

-continued
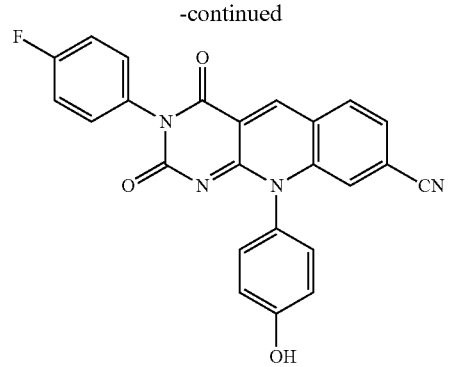
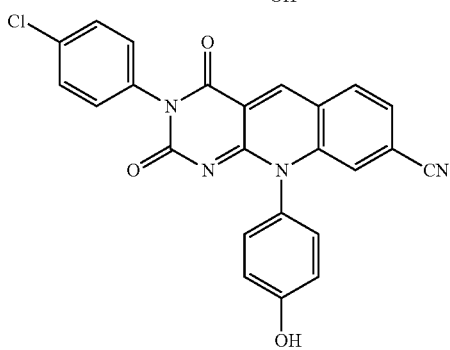
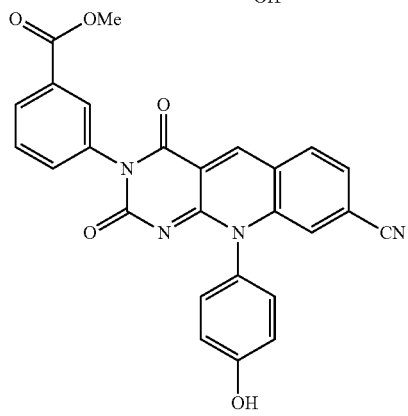
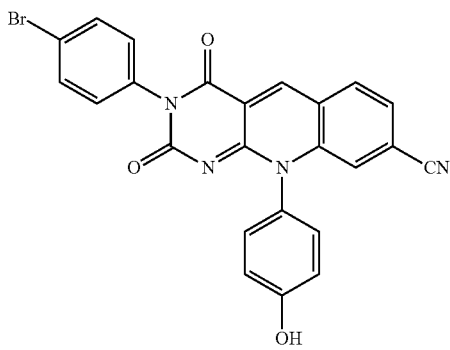
-continued
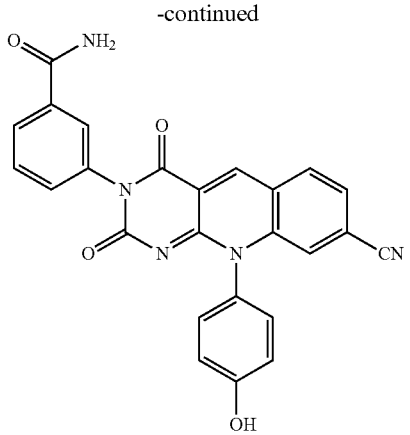
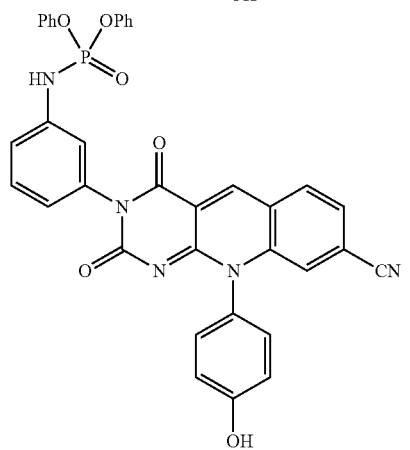
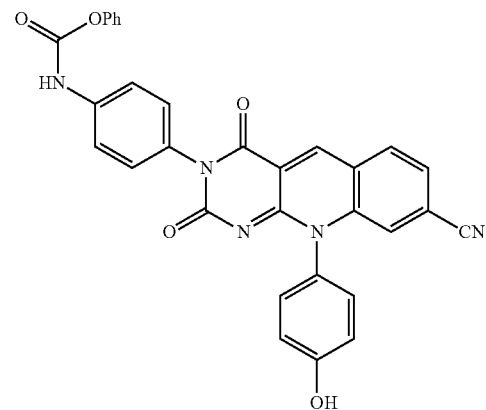 [SMILES: N#Cc1ccc2cc3c(=O)n(-c4ccc(NP(=O)(Oc5ccccc5)Oc5ccccc5)cc4)c(=O)nc-3n(-c3ccc(O)cc3)c2c1]
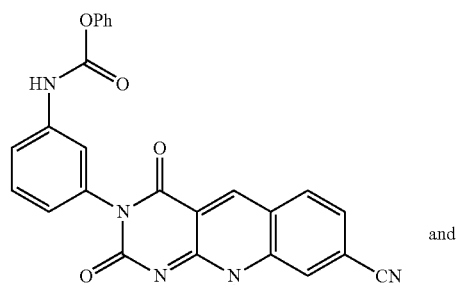
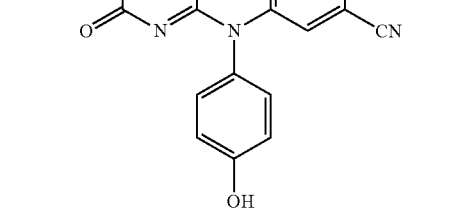
and

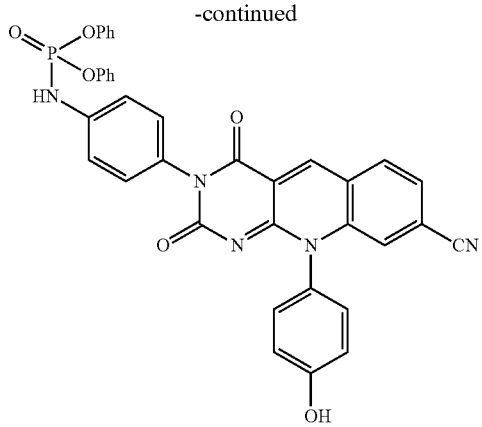

and salts thereof.

In one embodiment, the compound is used for treating cancer in an animal (e.g. a mammal such as a human), in combination with a Top2 poison.

In one embodiment, the compound is used for treating cancer in an animal (e.g. a mammal such as a human), in combination with etoposide.

In one embodiment, the compound is used for treating cancer in an animal (e.g. a mammal such as a human), in combination with mitoxantrone.

In cases where compounds are sufficiently basic or acidic, a salt of a compound of formula (I), (II) or (III) can be useful as an intermediate for isolating or purifying a compound of formula (I), (II) or (III). Additionally, administration of a compound of formula (I), (II) or (III) as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula (I), (II) or (III) can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula (I), (II) or (III) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula (I), (II) or (III) can be determined by comparing their in vitro activity, and in vivo activity in animal models. Methods for the extrapolation of effective dosages in mice, and other animals, to humans are known to the art; for example, see U.S. Pat. No, 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the treatment of cancer. Examples of such agents include TOP2 poisons such as, for example, etoposide, teniposide, doxorubicin, or daunorubicin. Accordingly, in one embodiment the invention also provides a kit comprising a compound of formula (I), (II), (III) or a pharmaceutically acceptable salt thereof, at least one other therapeutic agent (e.g. an anticancer agent such as a TOP2 poison), packaging material, and instructions for administering the compound of formula (I), (II), (III) or the pharmaceutically acceptable salt thereof and the other therapeutic agent or agents to an animal to treat cancer.

Processes for preparing compounds of formula (I), (II) or (III) are provided as further embodiments of the invention and are illustrated by the following procedures. Compounds of the invention can be prepared using procedures and starting materials that are known and available. Compounds of the invention can also be prepared as using the procedures and starting materials illustrated in the following Schemes.

Chemical Synthesis

Compound (5) can be prepared as illustrated in Scheme 1. Reaction of 6-chlorouracil 1 with aniline derivatives (2) provided 6-amination product 3 which upon reacting with 4-cyano-2-fluorobenzaldehyde (4) yielded the deazaflavin core (5, Raoof, A., et al., *J. Med. Chem.* 2013, 56, 6352-6370). Compound 11 was prepared as illustrated in Scheme 1B. The N-Boc protected 3 or 4-aminophenol (6) was treated with 3 or 4-bromobenzyl bromide (7) to yield corresponding O-benzyl derivatives which upon treatment with TFA gave the aniline derivative (9) (Vitaku, E., et al., *Angew. Chem. Int. Ed.* 2016, 55, 2243-2247). Compound 9 was then coupled with 6-chloro uracil (1) to furnish the 6-amination product 10 which underwent condensation followed by SNAr reaction upon treating with 4-cyano-2-fluorobenzaldehyde (4) (Raoof, A., et al., *J. Med. Chem.* 2013, 56, 6352-6370). The ester derivative (10f) was converted to acid (O-aryl) by saponification.

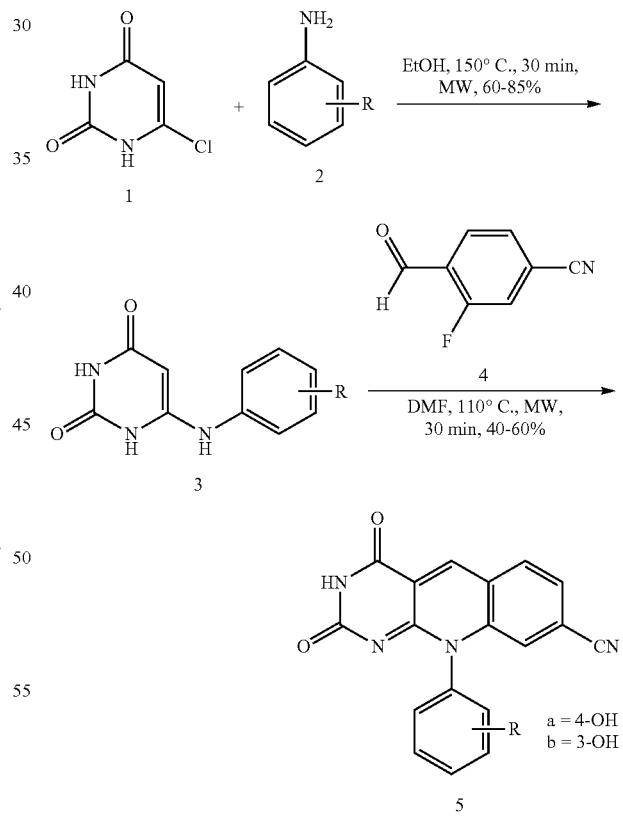

Scheme 1. Synthesis of O-aryl deazaflavin analogues (5 and 11).

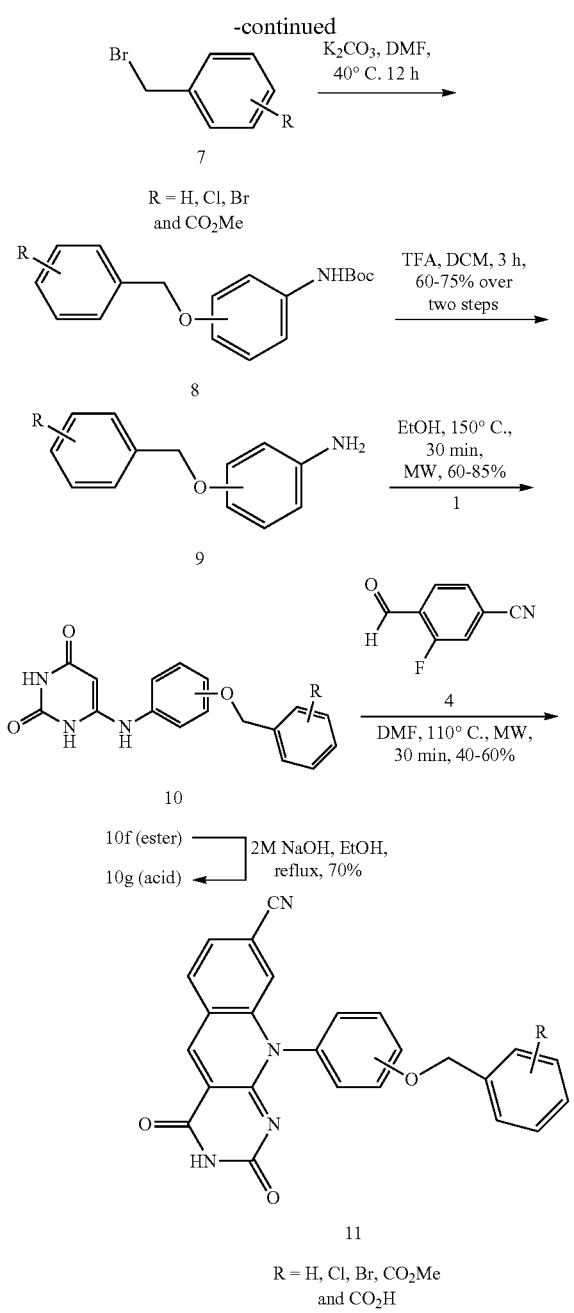

Scheme 2. Synthesis of dual mechanism inhibitors 16, 21, 22, 25 and 26. Compound with a carbamate warhead (16) was synthesized according to procedures illustrated in Scheme 2A. The amine (12) was treated with diphenyl phosphoryl chloride to produce intermediate 13 which was then treated with 10% Palladium over charcoal under hydrogen furnished the key aniline intermediate 14. Compound 14 was treated with 6-chlorouracil (1) followed by condensation and SNAr with 4-cyano-2-fluorobenzaldehyde (4) to produce the desired carbamate 16.

Compound with a boronic acid warhead (22) was synthesized according to procedures illustrated in Scheme 2B. The key aniline intermediate with a boronic acid warhead (19) was achieved via SNAr reaction of 1-fluoronitrobenzene and 18 followed by catalytic hydrogenation. Compound 19 which upon treatment with 6-chlorouracil and subsequent cyclization with 4 produced the corresponding boronate ester derivative (21) (Raoof, A., et al., *J. Med. Chem.* 2013, 56, 6352-6370), which was oxidatively cleaved using NaIO$_4$ to yield boronic acid (22) (Tzschucke, C. C., et al., *Org. Lett.* 2007, 9, 761-764).

In a similar fashion, the boronic warhead on O-benzyl derivatives was installed using the scheme 2B. The Miyaura borylation reaction on 9 enabled the synthesis of boronate esters (23) (Ingale, G., et al., *Tetrahedron Lett.* 2014, 55, 5247-5250), which was coupled with 6-chlorouracil (1) to produce the derivative of 6-amino uracil (24). Treatment of 24 with 4-cyano-2-fluorobenzaldehyde (4) gave the boronate ester (25) (Raoof, A., et al., *J. Med Chem.* 2013, 56, 6352-6370), which was oxidatively cleaved using NaIO$_4$ to yield boronic acid (26) (Tzschucke, C. C., et al., *Org. Lett.* 2007, 9, 761-764).

(A)

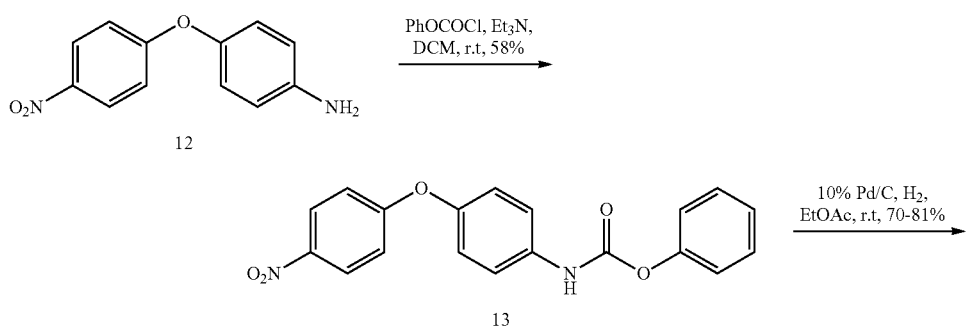

-continued
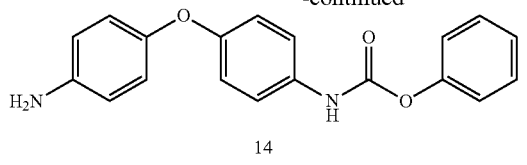
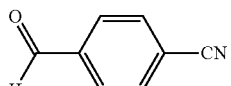
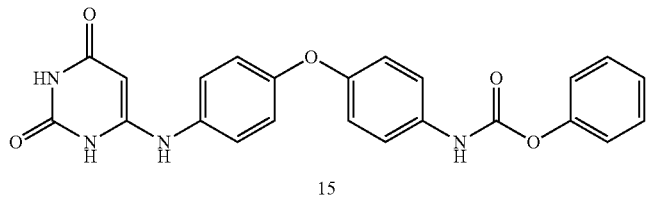
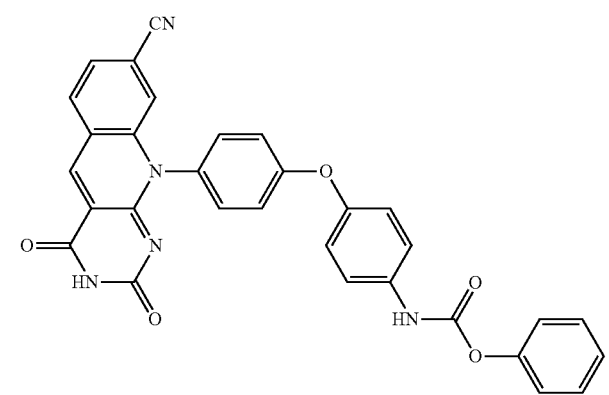
(B)
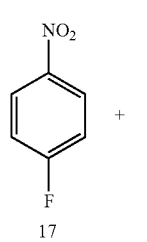 + 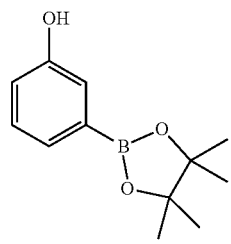 → 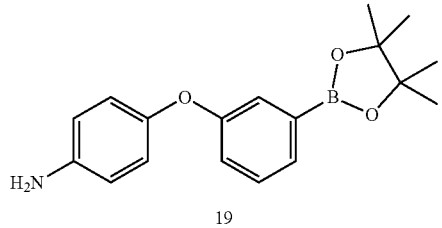
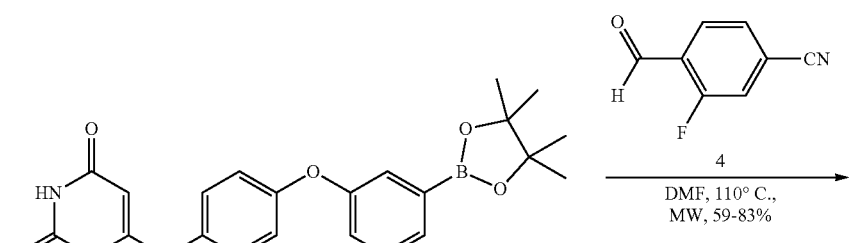

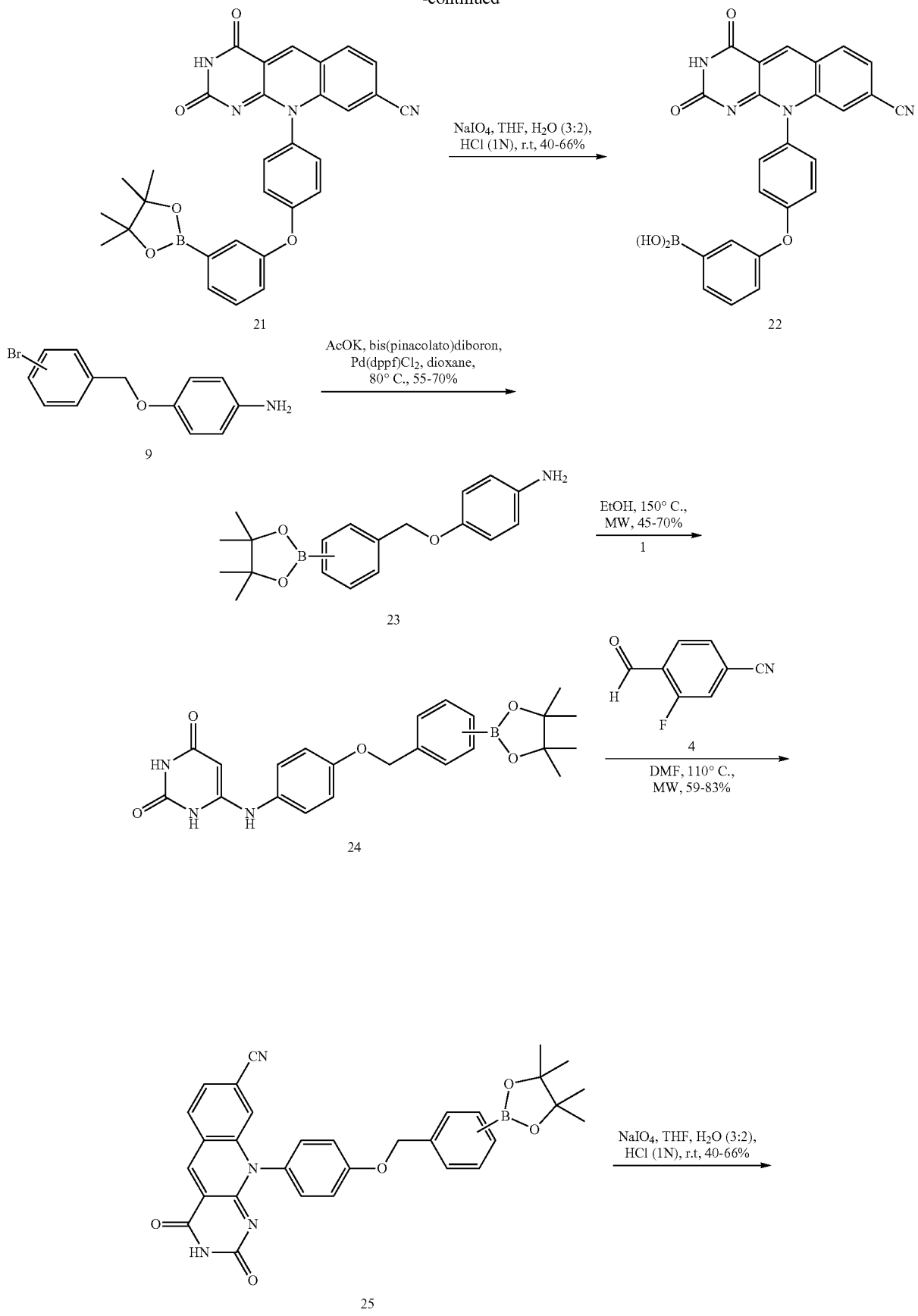

-continued

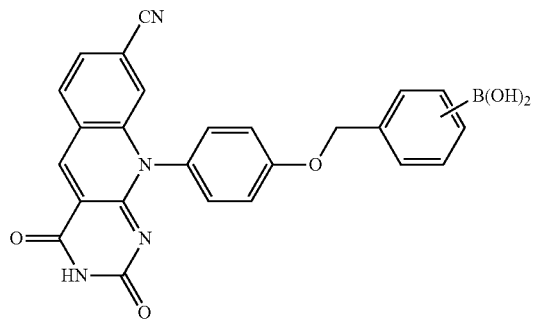

26

Scheme 3. Synthesis of N-aryl deazaflavins 31 via modified Chan-Lam synthesis.

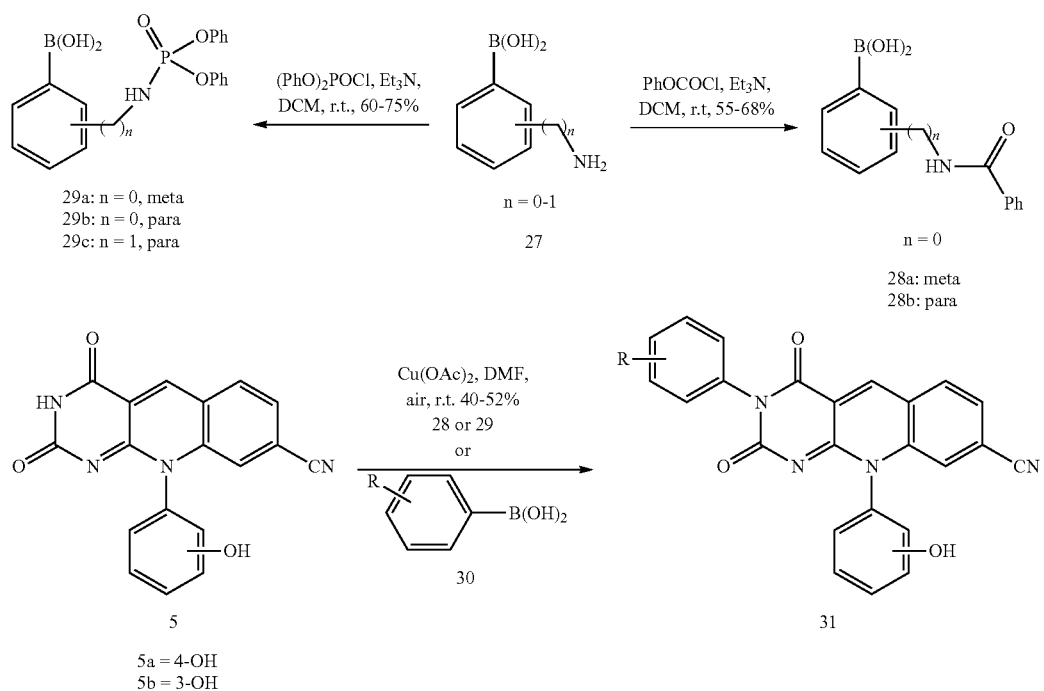

Compounds with a carbamate (28) or a phosphoramidate analogs (29) were synthesized according to procedures illustrated in Scheme 3. The synthesis started with amino phenylboronic acids (27). The amine was treated with phenyl chloroformate to produce intermediates 28, or with diphenyl phosphoryl chloride to generate intermediates 29 (Suksrichavalit, T., et al., *J. Chromatogr. A* 2010, 1217, 3635-3641). Intermediates 28-29 or a substituted boronic add were then subjected to a Chan-Lam synthesis to al low the installation of the carbamate or phosphoramidate-containing phenyl moiety or substituted phenyl moiety onto deazaflavin 5a-b to yield 31.

The invention will now be illustrated by the following non-limiting Examples.

General Procedures. All commercial chemicals were used as supplied unless otherwise indicated. Flash chromatography was performed on a Teledyne Combiflash RF-200 with RediSep columns (silica) and indicated mobile phase. All moisture sensitive reactions were performed under an inert atmosphere of ultrapure argon with oven-dried glassware. $^1$H and $^{13}$C NMR spectra were recorded on a Varian 600 MHz and Bruker 400 spectrometer. Mass data were acquired on an Agilent TOF II TOS/MS spectrometer capable of ESI and APCI ion sources. All tested compounds have a purity ≥95%.

PREPARATIVE EXAMPLES

Preparative Example 1

6-((4-Hydroxyphenyl)amino)pyrimidine-2,4(1H,3H)-dione (3a) (Raoof, A., et al., *J. Med. Chem.* 2013, 56, 6352-6370). To a suspension of 6-chlorouracil (0.50 g, 3.41 mmol, 1.0 eq) and 4-aminophenol (0.56 g, 5.12 mmol, 1.5 eq) in ethanol (5 mL) was irradiated at 150° C. for 30 minutes under microwave conditions. The reaction mixture was cooled and the precipitated solid was filtered, washed with cold methanol and ether and air dried to furnish the desired product as colorless solid (0.56 g, 75%). $^1$H NMR (600 MHz, DMSO-$d_6$) δ 10.31 (s, 1H), 10.06 (s, 1H), 9.50 (s, 1H), 7.82 (s, 1H), 7.02 (d, J=8.1 Hz, 2H), 6.77 (d, J=8.1 Hz, 2H), 4.35 (s, 1H).

Preparative Example 2

6-((3-Hydroxyphenyl)amino)pyrimidine-2,4(1H,3H)-dione (3b). Compound 3b was synthesized using the procedure as reported for 3a by replacing 4-aminophenol with 3-aminophenol. $^1$H NMR (600 MHz, DMSO-$d_6$) δ 10.45 (s, 1H), 10.04 (s, 1H), 9.57 (s, 1H), 8.17 (s, 1H), 7.15 (t, J=8.1 Hz, 1H), 6.63-6.59 (m, 2H), 6.54 (dd, J=8.1, 1.5 Hz, 1H), 4.76 (s, 1H).

Preparative Example 3

6-((4-(Trifluoromethoxy)phenyl)amino)pyrimidine-2,4 (1H,3H)-dione (3c). Compound 3c was synthesized using the procedure as reported for 3a. $^1$H NMR (600 MHz, DMSO-$d_6$) δ 10.50 (s, 1H), 10.29 (s, 1H), 8.43 (s, 1H), 7.36 (d, J=8.6 Hz, 2H), 7.33-7.27 (m, 2H), 4.71 (s, 1H).

Preparative Example 4

6-((4-(Difluoromethoxy)phenyl)amino)pyrimidine-2,4 (1H,3H)-dione (3d). Compound 3d was synthesized using the procedure as reported for 3a. $^1$H NMR (600 MHz, DMSO-$d_6$) δ 10.43 (s, 1H), 10.20 (s, 1H), 8.23 (s, 1H), 7.30 (t, J=78 Hz, 1H), 7.25-7.22 (m, 2H), 7.19-7.16 (m, 2H), 4.58 (s, 1H).

Preparative Example 5

6-(Benzo[d][1,3]dioxol-5-ylamino)pyrimidine-2,4(1H, 3H)-dione (3e). Compound 3e was synthesized using the procedure as reported for 3a. $^1$H NMR (600 MHz, DMSO-$d_6$) δ 10.36 (s, 1H), 10.12 (s, 1H), 7.98 (s, 1H), 6.91 (d, J=8.2 Hz, 1H), 6.82 (d, J=2.1 Hz, 1H), 6.67 (dd, J8.2, 2.1 Hz, 1H), 6.03 (s, 2H), 4.46 (s, 1H).

Preparative Example 6

6-((2,2-Difluorobenzo[d][1,3]dioxol-5-yl)amino)pyrimidine-2,4(1H,3H)-dione (3f). Compound 3f was synthesized using the procedure as reported for 3a. $^1$H NMR (600 MHz, DMSO-$d_6$) δ 10.46 (s, 1H), 10.29 (s, 1H), 8.35 (s, 1H), 7.39 (d, J=8.6 Hz, 1H), 7.33 (d, J=2.1 Hz, 1H), 7.02 (dd, J=8.6, 2.1 Hz, 1H), 4.60 (s, 1H).

Preparative Example 7

6-((4-Phenoxyphenyl)amino)pyrimidine-2,4(1H,3H)-dione (3g). Compound 3g was synthesized using the procedure as reported for 3a. $^1$H NMR (600 MHz, DMSO-$d_6$) δ 10.42 (s, 1H), 10.18 (s, 1H), 8.17 (s, 1H), 7.39 (t, J=7.8 Hz, 2H), 7.23 (d, J=8.6 Hz, 2H), 7.14 (t, J=7.3 Hz, 1H), 7.05-7.01 (m, 4H), 4.58 (s, 1H).

Preparative Example 8

6-((3-Phenoxyphenyl)amino)pyrimidine-2,4(1H,3H)-dione (3h). Compound 3h was synthesized using the procedure as reported for 3a. $^1$H NMR (600 MHz, DMSO-$d_6$) δ 10.48 (s, 1H), 10.19 (s, 1H), 8.38 (s, 1H), 7.41 (t, J=7.8 Hz, 2H), 7.36 (t, J=8.1 Hz, 1H), 7.17 (t, J=7.3 Hz, 1H), 7.06 (d, J=8.0 Hz, 2H), 6.96 (d, J=7.8 Hz, 1H), 6.78 (s, 1H), 6.76 (d, J=8.2 Hz, 1H), 4.76 (s, 1H).

Preparative Example 9

6-((4-(4-Fluorophenoxy)phenyl)amino)pyrimidine-2,4 (1H,3H)-dione (3i). Compound 3i was synthesized using the procedure as reported for 3a. $^1$H NMR (600 MHz, DMSO-$d_6$) δ 10.41 (s, 1H), 10.17 (s, 1H), 8.16 (s, 1H), 7.24-7.20 (m, 4H), 7.09-7.06 (m, 2H), 7.02-6.99 (m, 2H), 4.56 (s, 1H).

Preparative Example 10

6-((4-(4-Chlorophenoxy)phenyl)amino)pyrimidine-2,4 (1H,3H)-dione (3j). Compound 3j was synthesized using the procedure as reported for 3a. $^1$H NMR (600 MHz, DMSO-$d_6$) δ 10.43 (s, 1H), 10.20 (s, 1H), 8.20 (s, 1H), 7.50-7.36 (m, 2H), 7.30-7.19 (m, 2H), 7.09-7.03 (m, 4H), 4.60 (s, 1H).

Preparative Example 11

Methyl 3-(4-((2,6-dioxo-1,2,3,6-tetrahydropyrimidin-4-yl)amino)phenoxy)-benzoate (3k). Compound 3k was synthesized using the procedure as reported for 3a. $^1$H NMR (600 MHz, DMSO-$d_6$) δ 10.43 (s, 1H), 10.22 (s, 1H), 8.22 (s, 1H), 7.72 (d, J=7.7 Hz, 1H), 7.55 (t, J=8.0 Hz, 1H), 7.46 (s, 1H), 7.34 (dd, J=8.2, 2.5 Hz, 1H), 7.26 (d, J=8.8 Hz, 2H), 7.10 (d, J=8.8 Hz, 2H), 4.61 (s, 1H), 3.83 (s, 3H).

Preparative Example 12

3-(4-((2,6-Dioxo-1,2,3,6-tetrahydropyrimidin-4-yl) amino)phenoxy)benzoic acid (3l). Compound 3l was synthesized using the procedure as reported for 3a. $^1$H NMR (600 MHz, DMSO-$d_6$) δ 13.11 (s, 1H), 10.43 (s, 1H), 10.24 (s, 1H), 8.29 (s, 1H), 7.69 (d, J=7.7 Hz, 1H), 7.51 (t, J=7.9 Hz, 1H), 7.46-7.42 (m, 1H), 7.32-7.28 (m, 1H), 7.26-7.22 (m, 2H), 7.11-7.08 (m, 2H), 4.61 (s, 1H).

Preparative Example 13

10-(4-Hydroxyphenyl)-2,4-dioxo-pyrimido[4,5-b]quinoline-8-carbonitrile (5a) (Raoof, A., et al., *J. Med. Chem.* 2013, 56, 6352-6370). To a suspension of 3a (1.0 g, 4.56 mmol) in DMF (5 mL) was added 4-cyano-2-fluorobenzaldehyde (4, 0.82 g, 5.47 mmol) and heated by microwave irradiation at 110° C. for 30 minutes. Water (20 mL) was added to the reaction mixture, and the resulting precipitate was filtered and washed with water. The crude compound was triturated in methanol to furnish the desired compound as yellow solid 5a. $^1$H NMR (600 MHz, DMSO-$d_6$) δ 11.21 (s, 1H), 10.03 (s, 1H), 9.13 (s, 1H), 8.39 (d, J=8.2 Hz, 1H), 7.87 (d, J=8.2 Hz, 1H), 7.20 (d, J=8.6 Hz, 2H), 7.12 (s, 1H), 7.03 (d, J=8.6 Hz, 2H). HRMS-ESI (+) m/z calculated for $C_{18}H_{11}N_4O_3$, 331.0826 [M+H]−; found: 331.0821.

Preparative Example 14

10-(3-Hydroxyphenyl)-2,4-dioxo-2,3,4,10-tetrahydropyrimido[4,5-b]-quinoline-8-carbonitrile (5b). Compound 5b was synthesized using a procedure similar to that described for the preparation of compound 5a. $^1$H NMR (600 MHz, DMSO-$d_6$) δ 11.22 (s, 1H), 10.04 (s, 1H), 9.13 (s, 1H), 8.39 (d, J=8.2 Hz, 1H), 7.87 (dd, J=8.2, 1.2 Hz, 1H), 7.49 (t, J=8.0 Hz, 1H), 7.08 (s, 1H), 7.04 (dd, J=8.2, 1.8 Hz, 1H), 6.82 (d, J=7.7 Hz, 1H), 6.80 (t, J=1.8 Hz, 1H), HRMS-ESI(+) m/z calculated for $C_{18}H_{11}N_4O_3$, 331.0826 [M+H]−; found: 331.0829.

Preparative Example 15

Tert-butyl (4-((4-chlorobenzyl)oxy)phenyl)carbamate (8c). To a solution of N-Boc protected 4-aminophenol (6a, 1.0 g, 4.78 mmol, 1.0 eq) in DMF (15 mL) was added $K_2CO_3$ (1.32 g, 9.56 mmol, 2.0 eq) and stirred for 15 min followed by the addition of 4-Chlorobenzyl bromide (7, 1.18 g, 5.74 mmol, 1.2 eq) over 15 min and stirred at r.t for 12 h. Water was added and the aqueous solution was extracted with EtOAc (3×25 mL) followed by brine, dried over $Na_2SO_4$ and evaporated in vacuo to leave a colorless solid. The crude compound was triturated with ether to furnish 8c which was sufficiently pure for the next step. $^1$H NMR (600 MHz, DMSO-$d_6$) δ 9.13 (s, 1H), 7.49-7.40 (m, 4H), 7.33 (d, J=7.9 Hz, 2H), 6.90 (d, J=9.0 Hz, 2H), 5.03 (s, 2H), 1.45 (s, 9H).

Preparative Example 16

Tert-butyl (4-((4-bromobenzyl)oxy)phenyl)carbamate (8d). Compound 8d was synthesized using a procedure similar to that described for the preparation of compound 8c. $^1$H NMR (600 MHz, DMSO-$d_6$) δ 9.13 (s, 1H), 7.57 (d, J=8.3 Hz, 2H), 7.39 (d, J=8.3 Hz, 2H), 7.33 (d, J=7.9 Hz, 2H), 6.89 (d, J=9.0 Hz, 2H), 5.02 (s, 2H), 1.45 (s, 9H).

Preparative Example 17

Tert-butyl (4-((3-chlorobenzyl)oxy)phenyl)carbamate (8e). Compound 8e was synthesized using a procedure similar to that described for the preparation of compound 8c. $^1$H NMR (600 MHz, DMSO-$d_6$) δ 9.13 (s, 1H), 7.48 (s, 1H), 7.43-7.36 (m, 3H), 7.34 (d, J=8.0 Hz, 2H), 6.92-6.89 (m, 2H), 5.05 (s, 2H), 1.45 (s, 9H).

Preparative Example 18

Methyl 3-((4-((tert-butoxycarbonyl)amino)phenoxy)-methyl)benzoate (8f). $^1$H NMR (600 MHz, DMSO-$d_6$) δ 9.14 (s, 1H), 8.02 (s, 1H), 7.91 (d, J=7.7 Hz, 1H), 7.71 (d, J=7.5 Hz, 1H), 7.54 (t, J=7.7 Hz, 1H), 7.35 (d, J=7.5 Hz, 2H), 6.92 (d, J=9.0 Hz, 2H), 5.13 (s, 2H), 3.86 (s, 3H), 1.46 (s, 9H).

Preparative Example 19

4-((4-Chlorobenzyl)oxy)aniline (9c). To a solution of TFA in DCM (4:1, 15 mL) was added N-Boc protected phenoxy aniline (8c, 1.4 g, 4.2 mmol) and stirred at r.t for 6 h. The solvent was evaporated in vacuo and neutralized with the solution with 2N NaOH (pH=7-9) and extracted with EtOAc (2×20 mL). The combined organic solution was washed with brine, dried over $Na_2SO_4$ and evaporated in vacuo to leave a colorless solid (9c, 0.74 g, 75%). $^1$H NMR (600 MHz, DMSO-$d_6$) δ 7.42-7.40 (m, 4H), 6.70 (d, J=8.6 Hz, 2H), 6.49 (d, J=8.6 Hz, 2H), 4.94 (s, 2H), 4.62 (s, 2H).

Preparative Example 20

4-((4-Bromobenzyl)oxy)aniline (9d). Compound 9d was synthesized using a procedure similar to that described for the preparation of compound 9c. $^1$H NMR (600 MHz, DMSO-$d_6$) δ 7.56 (d, J=8.2 Hz, 2H), 7.36 (d, J=8.2 Hz, 2H), 6.71 (d, J=8.7 Hz, 2H), 6.50 (d, J=8.7 Hz, 2H), 4.92 (s, 2H).

Preparative Example 21

6-((4-(Benzyloxy)phenyl)amino)pyrimidine-2,4(1H,3H)-dione (10a). Compound 10a was synthesized with 6-chlorouracil (1) and 4-(benzyloxy)aniline (9a) using the method as described for compound 3a. $^1$H NMR (600 MHz, DMSO-$d_6$) δ 10.35 (s, 1H), 10.11 (s, 1H), 7.96 (s, 1H), 7.44 (d, J 7.5 Hz, 2H), 7.39 (t, J=7.5 Hz, 2H), 7.33 (t, J=7.5 Hz, 1H), 7.16-7.11 (m, 2H), 7.05-6.99 (m, 2H), 5.10 (s, 2H), 4.42 (s, 1H).

Preparative Example 22

6-((3-(Benzyloxy)phenyl)amino)pyrimidine-2,4(1H,3H)-dione (10b), Compound 10b was synthesized with 6-chlorouracil (1) and 3-(benzyloxy)aniline (9b) using the method as described for compound 3a. $^1$H NMR (600 MHz, DMSO-$d_6$) δ 10.46 (s, 1H), 10.13 (s, 1H), 8.23 (s, 1H), 7.44 (d, J=7.5 Hz, 2H), 7.39 (t, J=7.5 Hz, 2H), 7.33 (t, J=7.5 Hz, 1H), 7.27 (t, J=8.0 Hz, 1H), 6.82-6.80 (m, 3H), 5.09 (s, 2H), 4.73 (s, 1H).

Preparative Example 23

6-((4-((4-Chlorobenzyl)oxy)phenyl)amino)pyrimidine-2,4(1H,3H)-dione (10c). Compound 10c was synthesized with 6-chlorouracil (1) and 4-((4-Chlorobenzyl)oxy)aniline (9c) using the method as described for compound 3a. $^1$H NMR (600 MHz, DMSO-$d_6$) δ 10.36 (s, 1H), 10.12 (s, 1H), 7.97 (s, 1H), 7.49-7.45 (m, 4H), 7.15 (d, J=8.6 Hz, 2H), 7.03 (d, J=8.6 Hz, 2H), 5.10 (s, 2H), 4.43 (s, 1H).

Preparative Example 24

6-((4-((4-Bromobenzyl)oxy)phenyl)amino)pyrimidine-2,4(1H,3H)-dione (10d). Compound 10d was synthesized with 6-chlorouracil (1) and 4-((4-Bromobenzyl)oxy)aniline (9d) using the method as described for compound 3a. $^1$H NMR (600 MHz, DMSO-$d_6$) δ 10.35 (s, 1H), 10.12 (s, 1H), 7.97 (s, 1H), 7.59 (d, J=8.3 Hz, 2H), 7.41 (d, J=8.3 Hz, 2H), 7.14 (d, J=8.8 Hz, 2H), 7.02 (d, J=8.8 Hz, 2H), 5.09 (s, 2H), 4.42 (s, 1H).

Preparative Example 25

6-((4-((3-Chlorobenzyl)oxy)phenyl)amino)pyrimidine-2,4(1H,3H)-dione (10e). Compound 10e was synthesized with 6-chlorouracil (1) and 4-((3-Chlorobenzyl)oxy)aniline (9e) using the method as described for compound 3a. $^1$H NMR (600 MHz, DMSO-$d_6$) δ 10.36 (s, 1H), 10.12 (s, 1H), 7.97 (s, 1H), 7.52 (s, 1H), 7.47-7.35 (m, 3H), 7.15 (d, J=8.8 Hz, 2H), 7.04 (d, J=8.8 Hz, 2H), 5.12 (s, 2H), 4.43 (s, 1H).

Preparative Example 26

Methyl 3-((4-((2,6-dioxo-1,2,3,6-tetrahydropyrimidin-4-yl)amino)phenoxy)-methyl)benzoate (10f). Compound 10f was synthesized with 6-chlorouracil (1) and methyl 3-((4-aminophenoxy)methyl)benzoate (9f) using the method as described for compound 3a. $^1$H NMR (600 MHz, DMSO-$d_6$) δ 10.35 (s, 1H), 10.12 (s, 1H), 8.05 (s, 1H), 7.97 (s, 1H), 7.92 (d, J=7.8 Hz, 1H), 7.73 (d, J=7.7 Hz, 1H), 7.56 (t, J=7.7 Hz, 1H), 7.15 (d, J=8.9 Hz, 2H), 7.05 (d, J=8.9 Hz, 2H), 5.19 (s, 2H), 4.43 (s, 1H), 3.86 (s, 3H).

Preparative Example 27

3-((4-(2,6-Dioxo-1,2,3,6-tetrahydropyrimidin-4-yl)amino)phenoxy) methyl)-benzoic acid (10g). To a solution of 10f (0.3 g, 1.0 eq) in ethanol (5 mL), was added NaOH (1N, 5 mL) and heated to reflux for 3 h. The reaction mixture was cooled and ethanol was evaporated invacuo to leave the aqueous solution. Water (5 mL) was added to it and acidified to a pH of 3-4 with 1N HCl. The resultant precipitate was filtered and washed with excess water and air dried to leave the desired acid 10g as colorless solid (85%). $^1$H NMR (600 MHz, DMSO-d$_6$) δ 13.02 (s, 1H), 10.36 (s, 1H), 10.16 (s, 1H), 8.07 (s, 1H), 8.03 (s, 1H), 7.90 (d, J=7.7 Hz, 1H), 7.70 (d, J=7.5 Hz, 1H), 7.53 (t, J=7.5 Hz, 1H), 7.15 (d, J=8.7 Hz, 2H), 7.05 (d, J=8.7 Hz, 2H), 5.18 (s, 2H), 4.44 (s, 1H).

Preparative Example 28

Phenyl (4-(4-nitrophenoxy)phenyl)carbamate (13). To a solution of 4-(4-nitrophenoxy)aniline (12, 1.0 g, 1.0 eq) in DCM (15 mL), phenyl chloroformate (0.6 mL, 1.1 eq) was added at 0° C. and stirred at r.t for 12 h. The solvent was evaporated and EtOAc (20 mL) was added to it. The organic layer was washed with water (2×15 mL), 1N HCl (2×10 mL), brine (20 mL) and dried over Na$_2$SO$_4$. The solvent was evaporated in vacuo to leave colorless oil which was triturated with diethyl ether to furnish 13 as a colorless solid which was used in the next step without any further purification. $^1$H NMR (600 MHz, DMSO-d$_6$) δ 10.35 (s, 1H), 8.25-8.19 (m, 2H), 7.60 (d, J=8.8 Hz, 2H), 7.44-7.40 (m, 2H), 7.25 (t, J=7.4 Hz, 1H), 7.23-7.20 (m, 2H), 7.19-7.15 (m, 2H), 7.10-7.06 (m, 2H).

Preparative Example 29

Phenyl (4-(4-aminophenoxy)phenyl)carbamate (14). To a solution of 13 (0.8 g) in EtOAc (15 mL), was added 10% palladium over charcoal (0.1 g) and stirred at room temperature for 5 h under hydrogen gas. The reaction mixture was filtered through celite and washed with EtOAc (10 mL). The solvent was evaporated invacuo to leave a colorless oil which was purified using combiflash with 0-15% EtOAc in hexane as an eluent to leave colorless solid (14, 70%). $^1$H NMR (600 MHz, DMSO-d$_6$) δ 10.09 (s, 1H), 7.45-7.36 (m, 4H), 7.29-7.15 (m, 3H), 6.88-6.79 (m, 2H), 6.77-6.68 (m, 2H), 6.61-6.53 (m, 2H), 4.91 (s, 2H).

Preparative Example 30

Phenyl 4-(4-((2,6-dioxo-1,2,3,6-tetrahydropyrimidin-4-yl)amino)phenoxy)-phenyl)carbamate (15). Compound 15 was synthesized with 6-chlorouracil (1) and Phenyl (4-(4-aminophenoxy)phenyl)carbamate (14) using the method as described for compound 3a. $^1$H NMR (600 MHz, DMSO-d$_6$) δ 10.40 (s, 1H), 10.23 (s, 1H), 10.15 (s, 1H), 8.13 (s, 1H), 7.52 (d, J=8.7 Hz, 2H), 7.44-7.40 (m, 2H), 7.27-7.24 (m, 1H), 7.23-7.18 (m, 4H), 7.05-7.02 (m, 2H), 7.00-6.97 (m, 2H), 4.55 (s, 1H).

Preparative Example 31

4-(3-(4,4,5,5-Tetramethyl-1,3,2-dioxaborolan-2-yl)phenoxy)aniline (19). $^1$H NMR (600 MHz, DMSO-d$_6$) δ 8.26 (d, J=9.2 Hz, 2H), 7.59 (d, J=7.3 Hz, 1H), 7.53 (t, J=7.6 Hz, 1H), 7.37-7.32 (m, 2H), 7.13 (d, J=9.2 Hz, 2H), 1.29 (s, 12H).

Preparative Example 32

6-((4-(3-(4,4,5,5-Tetramethyl-1,3,2-dioxaborolan-2-yl) phenoxy)phenyl)-amino)pyrimidine-2,4(1H,3H)-dione (20). Compound 20 was synthesized with 6-chlorouracil (1) and compound 19 using the method as described for compound 3a. $^1$H NMR (600 MHz, DMSO-d$_6$) δ 10.42 (s, 1H), 10.20 (s, 1H), 8.19 (s, 1H), 7.43 (d, J=8.0 Hz, 2H), 7.24 (d, J=8.8 Hz, 2H), 7.19 (dd, J=6.4, 1.7 Hz, 2H), 7.06-7.02 (m, 2H), 4.60 (s, 1H), 1.28 (s, 12H).

Preparative Example 33

4-((3-(4,4,5,5-tetramethyl-1,3,2-dioxaborolan-2-yl)benzyl)oxy)aniline (23a) (Ingale, G., et al., *Tetrahedron Lett.* 2014, 55, 5247-5250). The mixture of 4((3-bromobenzyl) oxy)aniline 9 (1.0 g, 3.6 mmol, 1.0 equiv.), bis(pinacolato) diboron (1.37 g, 5.4 mmol, 1.5 equiv.), KOAc (0.71 g, 7.19 mmol, 2.0 equiv.), dioxane (15 mL) and PdCl$_2$(dppf)$_2$ (0.13 g, 0.18 mmol, 5%) were microwaved at 120° C. for 40 min. The suspension was filtered and washed with EtOAc. The solvent was evaporated and the residue was diluted with EtOAc and washed with brine, organic layer was dried over Na$_2$SO$_4$, filtered and concentrated. The crude product was purified by flash column chromatography (EtOAc/hexane; 1:9) to afford desired compound 23a (0.64 g, 55%) as a colorless solid. $^1$H NMR (600 MHz, DMSO-d$_6$) δ 7.71 (s, 1H), 7.60 (d, J=7.3 Hz, 1H), 7.52 (d, J=7.6 Hz, 1H), 7.38 (t, J=7.5 Hz, 1H), 6.71 (d, J=8.8 Hz, 2H), 6.49 (d, J=8.8 Hz, 2H), 4.95 (s, 2H), 4.61 (s, 2H), 1.29 (s, 12H).

Preparative Example 34

6-((4-((3-(4,4,5,5-tetramethyl-1,3,2-dioxaborolan-2-yl) benzyl) oxy) phenyl) amino) pyrimidine-2,4(1H,3H)-dione (24a). Compound 24a was synthesized with 6-chlorouracil (1) and compound 23a using the method as described for compound 3a. $^1$H NMR (600 MHz, DMSO-d$_6$) δ 10.35 (s, 1H), 10.12 (s, 1H), 7.98 (s, 1H), 7.76 (s, 1H), 7.63 (d, J=7.2 Hz, 1H), 7.58 (d, J=7.4 Hz, 1H), 7.41 (t, J=7.5 Hz, 1H), 7.15 (d, J=8.6 Hz, 2H), 7.03 (d, J=8.7 Hz, 2H), 5.12 (s, 2H), 4.43 (s, 1H), 1.30 (s, 12H).

Preparative Example 35

6-((4-((4-(4,4,5,5-tetramethyl-1,3,2-dioxaborolan-2-yl) benzyl) oxy) phenyl) amino) pyrimidine-2,4(1H,3H)-dione (24b). Compound 24b was synthesized as described for compound 3a. $^1$H NMR (600 MHz, DMSO-d$_6$) δ 10.35 (s, 1H), 10.12 (s, 1H), 7.98 (s, 1H), 7.69 (d, J=7.9 Hz, 2H), 7.45 (d, J=7.9 Hz, 2H), 7.14 (d, J=8.9 Hz, 2H), 7.02 (d, J=8.9 Hz, 2H), 5.14 (s, 2H), 4.42 (s, 1H), 1.29 (s, 13H).

Preparative Example 36

(3-((Phenoxycarbonyl)amino)phenyl)boronic acid (28a). To a solution of 3-aminophenylboronic acid (27, 1.0 eq) in DCM, phenyl chloroformate (1.1 eq) was added at 0° C. and stirred at r.t for 12 h. The solvent was evaporated and EtOAc (20 mL) was added to it. The organic layer was washed with water (2×15 mL), 1N HCl (2×10 mL), brine (20 mL) and dried over Na$_2$SO$_4$. The solvent was evaporated in vacuo to leave colorless oil 28a which was used in the next step without any further purification. Compound 28b was synthesized using the procedure described above using 4-aminophenylboronic acid. For compounds 29a-c, diphenylphosphoryl chloride was used in the place of phenyl chloroformate.

EXAMPLES

Example 101

2,4-Dioxo-10-(4-(trifluoromethoxy)phenyl)-2,3,4,10-tetrahydropyrimido[4,5-b]quinoline-8-carbonitrile. Compound was synthesized using the method as described for 5a. Yellow solid, 72% yield; $^1$H NMR (600 MHz, DMSO-$d_6$) δ 11.27 (s, 1H), 9.16 (s, 1H), 8.41 (d, J=7.8 Hz, 1H), 7.89 (d, J=7.8 Hz, 1H), 7.71 (d, J=7.6 Hz, 2H), 7.60 (d, J=7.5 Hz, 2H), 7.19 (s, 1H). $^{13}$C NMR (150 MHz, DMSO-$d_6$) δ 161.0, 158.7, 155.8, 148.5, 140.9, 140.8, 135.2, 132.1, 130.4, 126.2, 123.3, 122.5, 120.6, 117.8, 117.4, 115.5. HRMS-ESI (+) m/z calculated for $C_{19}H_{10}F_3N_4O_3$, 399.0705 [M+H]$^+$; found: 399.0707.

Example 102

10-(4-(Difluoromethoxy)phenyl)-2,4-dioxo-2,3,4,10-tetrahydropyrimido[4,5-b]quinoline-8-carbonitrile. The title compound was prepared using a procedure similar to that described in Example 101. Yellow solid, 62% yield; $^1$H NMR (600 MHz, DMSO-$d_6$) δ 11.25 (s, 1H), 9.15 (s, 1H), 8.40 (d, J=8.2 Hz, 1H), 7.89 (dd, J=8.1, 1.3 Hz, 1H), 7.56 (t, J=78 Hz, 1H), 7.52-7.48 (m, 4H), 7.15 (s, 1H). $^{13}$C NMR (150 MHz, DMSO-$d_6$) δ 161.4, 159.1, 156.2, 151.7, 141.4, 141.2, 133.4, 132.5, 130.3, 126.5, 123.6, 121.0, 120.2, 118.2, 118.1 (t, J=256.5 Hz), 117.8, 115.8. HRMS-ESI (+) m/z calculated for $C_{19}H_{11}F_2N_4O_3$, 381.0799 [M+H]$^+$; found: 381.0800.

Example 103

10-(Benzo[d][1,3]dioxol-5-yl)-2,4-dioxo-2,3,4,10-tetrahydropyrimido[4,5-b]quinoline-8-carbonitrile. The title compound was prepared using a procedure similar to that described in Example 101. Yellow solid, 66% yield; $^1$H NMR (600 MHz, DMSO-$d_6$) δ 11.24 (s, 1H), 9.14 (s, 1H), 8.39 (d, J=8.1 Hz, 1H), 7.88 (d, J=8.1 Hz, 1H), 7.29 (s, 1H), 7.19 (d, J=8.2 Hz, 1H), 7.04 (d, J=1.5 Hz, 1H), 6.88 (dd, J=8.1, 1.6 Hz, 1H), 6.21 (d, J=1.9 Hz, 2H). $^{13}$C NMR (100 MHz; DMSO-$d_6$) δ 161.3, 159.0, 156.1, 148.5, 148.0, 141.5, 140.9, 132.2, 130.0, 126.2, 123.3, 121.6, 121.1, 117.9, 117.6, 115.6, 109.0, 108.9, 102.0. HRMS-ESI (+) m/z calculated for $C_{19}H_{11}N_4O_4$, 359.0780 [M+H]$^+$; found: 359.0783.

Example 104

10-(2,2-Difluorobenzo[d][1,3]dioxol-5-yl)-2,4-dioxo-2,3,4,10-tetrahydropyrimido[4,5-b]quinoline-8-carbonitrile. The title compound was prepared using a procedure similar to that described in Example 101. Yellow solid, 73% yield; $^1$H NMR (600 MHz, DMSO-$d_6$) δ 11.28 (s, 1H), 9.17 (s, 1H), 8.39 (d, J=8.2 Hz, 1H), 7.89 (dd, J=8.1, 1.2 Hz, 1H), 7.71 (d, J=8.5 Hz, 1H), 7.59 (d, J=1.9 Hz, 1H), 7.49 (s, 1H), 7.29 (dd, J=8.5, 2.0 Hz, 1H), $^{13}$C NMR (100 MHz, DMSO-$d_6$) δ 161.2, 159.0, 156.0, 143.7, 143.3, 141.3, 141.2, 132.6, 132.1, 126.5, 124.8, 123.3, 121.3, 117.8, 117.6, 115.8, 111.3, 111.0. HRMS-ESI (+) m/z calculated for $C_{19}H_9F_2N_4O_4$, 395.0592 [M+H]$^+$; found: 395.0596.

Example 105

2,4-Dioxo-10-(4-phenoxyphenyl)-2,3,4,10-tetrahydropyrimido[4,5-b]quinoline-8-carbonitrile. The title compound was prepared using a procedure similar to that described in Example 101. Yellow solid, 79% yield; $^1$H NMR (600 MHz, DMSO-$d_6$) δ 11.25 (s, 1H), 9.15 (s, 1H), 7.89 (d, J=8.0 Hz, 1H), 7.50 (t, J=7.8 Hz, 2H), 7.42 (d, J=8.6 Hz, 2H), 7.26 (t, J=7.9 Hz, 5H), 7.22 (s, 1H). $^{13}$C NMR (150 MHz, DMSO-$d_6$) δ 161.4, 159.2, 157.9, 156.3, 155.4, 141.6, 141.1, 132.4, 131.3, 130.3, 130.1, 126.4, 124.5, 123.6, 121.1, 119.9, 119.1, 118.2, 117.8, 115.8. HRMS-ESI (+) m/z calculated for $C_{24}H_{15}N_4O_3$, 407.1144 [M+H]$^+$; found: 407.1146.

Example 106

2,4-Dioxo-10-(3-phenoxyphenyl)-2,3,4,10-tetrahydropyrimido[4,5-b]quinoline-8-carbonitrile. The title compound was prepared using a procedure similar to that described in Example 101. Yellow solid, 71% yield; $^1$H NMR (600 MHz, DMSO-$d_6$) δ 11.24 (s, 1H), 9.13 (s, 1H), 8.39 (d, J=8.1 Hz, 1H), 7.89 (d, J=8.1 Hz, 1H), 7.70 (t, J=8.1 Hz, 1H), 7.43 (t, J=7.7 Hz, 2H), 7.26 (d, J=9.1 Hz, 2H), 7.23-7.15 (m, 5H). $^{13}$C NMR (150 MHz, DMSO-$d_6$) δ 161.3, 158.7, 158.2, 156.1, 155.7, 141.0, 140.9, 137.9, 132.3, 131.6, 130.1, 126.3, 124.0, 123.5, 122.9, 120.9, 119.2, 119.1, 118.2, 118.1, 117.7, 115.7. HRMS-ESI (+) m/z calculated for $C_{24}H_{15}N_4O_3$, 407.1144 [M+H]$^+$; found: 407.1148.

Example 107

10-(4-(4-Fluorophenoxy)phenyl)-2,4-dioxo-2,3,4,10-tetrahydropyrimido[4,5-b]quinoline-8-carbonitrile. The title compound was prepared using a procedure similar to that described in Example 101. Yellow solid, 81% yield; $^1$H NMR (400 MHz, DMSO-$d_6$) δ 11.24 (s, 1H), 9.15 (s, 1H), 8.40 (d, J=8.2 Hz, 1H), 7.89 (dd, J=8.1, 1.2 Hz, 1H), 7.41 (dd, J=9.4, 2.5 Hz, 2H), 7.35-7.31 (m, 4H), 7.25-7.20 (m, 3H). $^{13}$C NMR (150 MHz, DMSO-$d_6$) δ 161.7, 159.8 (d, J=238.5 Hz), 159.4, 158.5, 156.5, 151.6, 141.8, 141.3, 132.7, 131.5, 130.3, 126.7, 123.9, 122.3 (d, J=7.5 Hz), 121.3, 118.9, 118.4, 118.0, 117.2 (d, J=24 Hz), 116.0. HRMS-ESI (+) m/z calculated for $C_{24}H_{14}FN_4O_3$, 425.1050 [M+H]$^+$; found: 425.1052.

Example 108

10-(4-(4-chlorophenoxy)phenyl)-2,4-dioxo-2,3,4,10-tetrahydropyrimido[4,5-b]quinoline-8-carbonitrile. The title compound was prepared using a procedure similar to that described in Example 101. Yellow solid, 79% yield; $^1$H NMR (600 MHz, DMSO-$d_6$) δ 11.25 (s, 1H), 9.16 (s, 1H), 8.41 (d, J=8.2 Hz, 1H), 7.90 (dd, J=8.2, 1.3 Hz, 1H), 7.57-7.50 (m, 2H), 7.50-7.40 (m, 2H), 7.32-7.28 (m, 4H), 7.24 (s, 1H). $^{13}$C NMR (150 MHz, DMSO-$d_6$) δ 161.2, 158.9, 157.2, 156.0, 154.2, 141.3, 140.8, 132.2, 131.4, 129.9, 129.8, 128.0, 126.2, 123.4, 121.3, 120.8, 119.1, 117.9, 117.5, 115.5, HRMS-ESI (+) m/z calculated for $C_{24}H_{14}ClN_4O_3$, 441.0754 [M+H]$^+$; found: 441.0756.

Example 109

Methyl-3-(4-(8-cyano-2,4-dioxo-3,4-dihydropyrimido[4,5-b]quinolin-10(2H)-yl)phenoxy)-benzoate. The title compound was prepared using a procedure similar to that described in Example 101. Yellow solid, 75% yield; $^1$H NMR (600 MHz, DMSO-$d_6$) δ 11.25 (s, 1H), 9.15 (s, 1H), 8.40 (d, J=8.1 Hz, 1H), 7.89 (dd, J=8.1, 1.3 Hz, 1H), 7.83 (d, J=7.9 Hz, 1H), 7.73-7.68 (m, 1H), 7.65 (t, J=7.9 Hz, 1H), 7.59-7.55 (m, 1H), 7.47-7.44 (m, 2H), 7.32 (dd, J=9.3, 2.6 Hz, 2H), 7.23 (s, 1H), 3.87 (s, 3H). $^{13}$C NMR (100 MHz, DMSO-$d_6$) δ 165.3, 161.3, 159.0, 157.1, 156.1, 155.8, 141.4, 140.9, 132.3, 131.8, 131.5, 130.7, 130.1, 126.3, 124.8, 124.4, 123.4, 120.9, 119.6, 119.5, 118.0, 117.6, 115.6, 52.2. HRMS-ESI (+) m/z calculated for $C_{26}H_{17}N_4O_5$, 465.1199 [M+H]$^+$; found: 465.1202.

Example 110

3-(4-(8-Cyano-2,4-dioxo-3,4-dihydropyrimido[4,5-b]quinolin-10(2H)-yl)phenoxy)benzoic acid. The title compound was prepared using a procedure similar to that described in Example 101. Yellow solid, 67% yield; $^1$H NMR (400 MHz, DMSO-d$_6$) δ 11.25 (s, 1H), 9.15 (s, 1H), 8.41 (d, J=8.2 Hz, 1H), 7.89 (dd, J=8.2, 1.0 Hz, 1H), 7.81 (d, J=7.6 Hz, 1H), 7.72 (s, 1H), 7.61 (t, J=7.9 Hz, 1H), 7.51 (dd, J=7.9, 2.0 Hz, 1H), 7.45 (d, J=8.8 Hz, 2H), 7.31 (d, J=8.8 Hz, 2H), 7.24 (s, 1H). $^{13}$C NMR (100 MHz, DMSO-d$_6$) δ 166.6, 161.3, 159.0, 157.3, 156.1 155.5, 141.4, 140.9, 133.5, 132.3, 131.6, 130.4, 130.1, 126.3, 125.0, 123.7, 123.4, 120,9, 119.8, 119.4, 118.0, 117.6, 115.6. HRMS-ESI (+) m/z calculated for C$_{25}$H$_{15}$N$_4$O$_5$, 451.1042 [M+H]$^+$, found: 451.1046.

Example 111

10-(4-(Benzyloxy)phenyl)-2,4-dioxo-2,3,4,10-tetrahydropyrimido[4,5-b]quinoline-8-carbonitrile. The title compound was prepared using a procedure similar to that described in Example 101. Yellow solid, 75% yield; $^1$H NMR (600 MHz, DMSO-d$_6$) δ 11.23 (s, 1H), 9.14 (s, 1H), 8.39 (d, J=8.2 Hz, 1H), 7.87 (dd, J=8.1, 1.2 Hz, 1H), 7.53 (d, J=7.4 Hz, 2H), 7.44 (t, J=7.5 Hz, 2H), 7.37-7.33 (m, 3H), 7.31 (d, J=9.0 Hz, 2H), 7.12 (s, 1H), 5.23 (s, 2H). $^{13}$C NMR (100 MHz, DMSO-d$_6$) δ 161.3, 159.0, 158.8, 156.1, 141.5, 140.8, 136.5, 132.3, 129.3, 129.2, 128.3, 127.84, 127.7, 126.1, 123.4, 120.9, 118.0, 117.6, 116.1, 115.5, 69.6. HRMS-ESI (+) m/z calculated for C$_{25}$H$_{17}$N$_4$O$_3$, 421.1301 [M+H]$^+$, found: 421.1303.

Example 112

10-(3-(Benzyloxy)phenyl)-2,4-dioxo-2,3,4,10-tetrahydropyrimido[4,5-b]quinoline-8-carbonitrile. The title compound was prepared using a procedure similar to that described in Example 101. Yellow solid, 81% yield; $^1$H NMR (600 MHz, DMSO-d$_6$) δ11.25 (s, 1H), 9.16 (s, 1H), 8.40 (d, J=8.1 Hz, 1H), 7.88 (d, J=8.0 Hz, 1H), 7.63 (t, J=8.0 Hz, 1H), 7.48 (d, J=7.3 Hz, 2H), 7.40 (t, J=7.3 Hz, 2H), 7.36-7.28 (m, 2H), 7.16 (s, 1H), 7.05 (s, 1H), 7.01 (d, J=7.5 Hz, 1H), 5.15 (s, 2H). $^{13}$C NMR (100 MHz, DMSO-d$_6$) δ 161.3, 159.6, 158.6, 156.1, 141.0, 140.9, 137.7, 136.3, 132.3, 131.1, 128.3, 127.8, 126.2, 123.4, 120.8, 120.3, 118.0, 117.6, 116.1, 115.6, 114.7, 69.5. HRMS-ESI (+) m/z calculated for C$_{25}$H$_{17}$N$_4$O$_3$, 421.1301 [M+H]$^+$; found: 421.1305.

Example 113

10-(4-((4-Chlorobenzyl)oxy)phenyl)-2,4-dioxo-2,3,4,10-tetrahydropyrimido[4,5-b]quinoline-8-carbonitrile. The title compound was prepared using a procedure similar to that described in Example 101. Yellow solid, 58% yield; $^1$H NMR (600 MHz, DMSO-d$_6$) δ 11.23 (s, 1H), 9.15 (s, 1H), 8.40 (d, J=8.1 Hz, 1H), 7.88 (d, J=8.1 Hz, 1H), 7.56 (d, J=8.1 Hz, 2H), 7.51 (d, J=8.1 Hz, 2H), 7.37 (d, J=8.4 Hz, 2H), 7.31 (d, J=8.4 Hz, 2H), 7.11 (s, 1H), 5.24 (s, 2H). $^{13}$C NMR (100 MHz, DMSO-d$_6$) δ 161.1, 158.8, 158.4, 155.9, 141.3, 140.6, 135.4, 132.2, 132.1, 129.3 129.2, 128.2, 125.9, 125.1, 123.2 120.7, 117.8, 117.4, 115.9, 115.3, 68.5. HRMS-ESI (+) m/z calculated for C$_{25}$H$_{16}$ClN$_4$O$_3$, 455.0911 [M+H]$^+$; found: 455.0912.

Example 114

10-(4-((4-Bromobenzyl) oxy) phenyl)-2,4-dioxo-2,3,4, 10-tetrahydropyrimido [4,5-b] quinoline-8-carbonitrile. The title compound was prepared using a procedure similar to that described in Example 101. Orange solid, 69% yield; $^1$H NMR (600 MHz, DMSO-d$_6$) δ 11.23 (s, 1H), 9.15 (s, 1H), 8.40 (d, J=7.5 Hz, 1H), 7.88 (d, J=7.4 Hz, 1H), 7.64 (d, J=7.3 Hz, 2H), 7.50 (d, J=7.2 Hz, 2H), 7.36 (d, J=7.8 Hz, 2H), 7.31 (d, J=7.0 Hz, 2H), 7.11 (s, 1H), 5.22 (s, 2H). $^{13}$C NMR (150 MHz, DMSO-d$_6$) δ 161.8, 159.5, 159.1, 156.5, 142.0, 141.4, 141.2, 136.5, 131.6, 130.4, 130.2, 129.8, 129.7, 123.9, 121.4, 118.5, 118.1, 116.8, 116.4, 115.9, 69.2. HRMS-ESI (+) m/z calculated for C$_{25}$H$_{16}$BrN$_4$O$_3$, 499.0406 [M+H]$^+$; found: 499.0407.

Example 115

10-(4-((3-Chlorobenzyl)oxy)phenyl)-2,4-dioxo-2,3,4,10-tetrahydropyrimido[4,5-b]-quinolone -8-carbonitrile. The title compound was prepared using a procedure similar to that described in Example 101. Yellow solid, 52% yield; $^1$H NMR (600 MHz, DMSO-d$_6$) δ 11.24 (s, 1H), 9.15 (s, 1H), 8.40 (d, J=8.2 Hz, 1H), 7.88 (dd, J=8.2, 1.2 Hz, 1H), 7.61 (s, 1H), 7.52-7.44 (m, 3H), 7.37 (d, J=9.0 Hz, 2H), 7.32 (d, J=9.0 Hz, 2H), 7.12. (s, 1H), 5.26 (s, 2H). $^{13}$C NMR (100 MHz, DMSO-d$_6$) δ 162.2, 159.9, 159.4, 156.9, 142.4, 141.7, 140.0, 133.8, 133.1, 131.1, 130.2, 128.6, 128.2, 127.1, 126,9, 124.3, 121.7, 118.9, 118.4, 117.0, 116.3, 69.5. HRMS-ESI (+) m/z calculated for C$_{25}$H$_{16}$ClN$_4$O$_3$, 455.0911 [M+H]$^+$; found: 455.0915.

Example 116

Methyl-3-((4-(8-cyano-2,4-dioxo-3,4-dihydropyrimido [4,5-b]quinolin-10(2H)-yl)phenoxy) methyl)benzoate). The title compound was prepared using a procedure similar to that described in Example 101. Yellow solid, 82% yield; $^1$H NMR (600 MHz, DMSO-d$_6$) δ 11.23 (s, 1H), 9.14 (s, 1H), 8.40 (d, J=7.4 Hz, 1H), 8.13 (s, 1H), 7.97 (d, J=7.4 Hz, 1H), 7.88 (d, J=7.5 Hz, 1H), 7.82 (d, J=7.4 Hz, 1H), 7.65-7.58 (m, 1H), 7.38-7.34 (m, 4H), 7.11 (s, 1H), 5.33 (s, 2H), 3.88 (s, 3H). $^{13}$C NMR (100 MHz, DMSO-d$_6$) δ 166.3, 161.7, 159.4, 159.0, 156.5, 142.0, 141.3, 137.8, 132.8, 132.7, 130.1, 129.8, 129.3, 129.0, 128.6, 126.5, 123.8, 121.3, 118.4, 118.0, 116.6, 115.9, 69.3, 52.5. HRMS-ESI (+) m/z calculated for C$_{27}$H$_{19}$N$_4$O$_5$, 479.1355 [M+H]$^+$; found: 479.1357.

Example 117

3-((4-(8-cyano-2,4-dioxo-3,4-dihydropyrimido[4,5-b] quinolin-10(2H)-yl)phenoxy) methyl)benzoic acid. The title compound was prepared using a procedure similar to that described in Example 101. Yellow solid, 52% yield; $^1$H NMR (600 MHz, DMSO-d$_6$) δ 13.05 (s, 1H), 11.23 (s, 1H), 9.15 (s, 1H), 8.40 (d, J=8.2 Hz, 1H), 8.11 (s, 1H), 7.95 (d, J=7.7 Hz, 1H), 7.88 (dd, J=8.2, 1.1 Hz, 1H), 7.78 (d, J=7.6 Hz, 1H), 7.58 (t, J=7.6 Hz, 1H), 7.37 (d, J=8.9 Hz, 2H), 7.33 (d, J=9.0 Hz, 2H), 7.12 (s, 1H), 5.31 (s, 2H). $^{13}$C NMR (100 MHz, DMSO-d$_6$) δ 167.5, 161.9, 159.6, 159.3, 156.7, 142.2, 141.4, 137.7, 132.9, 132.6, 131.5, 130.0, 129.3, 129.0, 126.7, 124.0, 121.5, 118.6, 118.2, 116.8, 116.1, 69.6. HRMS-EST (+) m/z calculated for C$_{26}$H$_{17}$N$_4$O$_5$, 465.1199 [M+H]$^+$; found: 465.1202.

Example 118

Phenyl (4-(4-(8-cyano-2,4-dioxo-3,4-dihydropyrimido[4, 5-b]quinolin-10(2H)-yl)phenoxy)-phenyl)carbamate). The title compound was prepared using a procedure similar to that described in Example 101. Yellow solid, 59% yield; $^{13}$H NMR (600 MHz, DMSO-d$_6$) δ 11.24 (s, 1H), 10.33 (s, 1H), 9.15 (s, 1H), 8.40 (d, J=8.2 Hz, 1H), 7.89 (dd, J=8.1, 1.1 Hz, 1H), 7.62 (d, J=8.6 Hz, 2H), 7.44 (t, J=7.9 Hz, 2H), 7.40 (d, J=8.8 Hz, 2H), 7.28-7.26 (m, 4H), 7.24-7.19 (m, 4H). $^{13}$C NMR (100 MHz, DMSO-$d_6$) δ 162.1, 160.5, 159.8, 157.9, 156.9, 146.8, 145.1, 142.3, 141.7, 133.1, 130.7, 130.35, 130.0, 127,0, 124.3, 122.5, 122.2, 121.7, 119.4, 118.8, 118.4, 117.9, 116.3, 115.8, 115.6, HRMS-ESI (+) m/z calculated for $C_{31}H_{20}N_5O_5$, 542.1464 [M+H]$^+$; found: 542.1466.

Example 119

2,4-Dioxo-10-(4-(3-(4,4,5,5-tetramethyl-1,3,2-dioxaborolan-2-yl)phenoxy)phenyl)-2,3,4,10-tetrahydropyrimido[4,5-b]quinoline-8-carbonitrile. The title compound was prepared using a procedure similar to that described in Example 101, Yellow solid, 83% yield; $^1$H NMR (600 MHz, DMSO-$d_6$) δ 11.25 (s, 1H), 9.15 (s, 1H), 8.40 (d, J=8.2 Hz, 1H), 7.92-7.86 (m, 1H), 7.54-7.48 (m, 2H), 7.45-7.39 (m, 3H), 7.28-7.24 (m, 3H), 7.22 (d, J=8.9 Hz, 1H), 1.31 (s, 12H). $^{13}$C NMR (150 MHz, DMSO-$d_6$) δ 161.2, 158.9, 157.7, 156.0, 155.2, 141.3, 140.8, 132.2, 131.0, 130.04, 129.8, 126.2, 124.6, 124.2, 123.4, 122.9, 120.8, 119.7, 119.1, 118.8, 117.9, 115.5, 83.7, 24.4. HRMS-ESI (+) m/z calculated for $C_{30}H_{26}BN_4O_5$, 533.1996 [M+H]$^+$; found: 533.1999.

Example 120

(3-(4-(8-Cyano-2,4-dioxo-3,4-dihydropyrimido[4,5-b]quinolin-10(2H)-yl)phenoxy)phenyl) boronic acid. To a solution of 2,4-Dioxo-10-(4-(3-(4,4,5,5-tetramethyl-1,3,2-dioxaborolan-2-yl)phenoxy)phenyl)-2,3,4,10-tetrahydropyrimido[4,5-b]quinoline-8-carbonitrile (Example 119, 0.2 g, 1.0 eq) in a mixture of THF/$H_2O$ (3:2; 5 mL), was added NaIO$_4$ (0.24 g, 3.0 eq) and stirred at room temperature for 2 h before adding 1N HCl (0.3 mL). The solution was stirred at room temperature for 8 h and the solvent was evaporated invacuo to leave yellow solid which was purified using combiflash with 0-10% methanol in DCM to produce the boronic acid. Yellow solid, 66% yield; $^1$H NMR (600 MHz, DMSO-$d_6$) δ 11.23 (d, J=10.5 Hz, 1H), 9.14 (d, J=9.3 Hz, 1H), 8.40 (d, J=8.2 Hz, 1H), 8.18 (s, 2H), 7.88 (d, J=8.2 Hz, 1H), 7.69-7.65 (m, 2H), 7.46 (t, J=7.8 Hz, 1H), 7.41 (q, J=3.4 Hz, 2H), 7.30 (dd, J=8.2, 2.8 Hz, 1H), 7.22 (dd, J=12.6, 3.7 Hz, 3H). $^{13}$C NMR (100 MHz, DMSO-$d_6$) δ 162.1, 159.8, 159.0, 156.9, 155.3, 142.2, 141.8, 137.5, 133.1, 131.7, 131.1, 130.7, 130.1, 127.1, 126.1, 124.3, 122.6, 121.7, 119.4, 118.8, 118.5, 116.4. HRMS-ESI (+) m/z calculated for $C_{24}H_{16}BN_4O_5$, 451.1214 [M+H]$^+$; found: 451.1219.

Example 121

2,4-Dioxo-10-(4-((3-(4,4,5,5-tetramethyl-1,3,2-dioxaborolan-2-yl)benzyl)oxy)phenyl)-2,3,4,10-tetrahydropyrimido[4,5-b]quinoline-8-carbonitrile. The title compound was prepared using a procedure similar to that described in Example 101. Yellow solid, 66% yield; $^1$H NMR (600 MHz, DMSO-$d_6$) δ 11.23 (s, 1H), 9.15 (s, 1H), 8.40 (d, J=8.2 Hz, 1H), 7.88 (d, J=8.2 Hz, 1H), 7.84 (s, 1H), 7.67 (t, J=8.5 Hz, 2H), 7.46-7.44 (m, 1H), 7.36 (d, J=8.8 Hz, 2H), 7.31 (d, J=8.9 Hz, 2H), 7.11 (s, 1H), 5.25 (s, 2H), 1.32 (s, 12H). $^{13}$C NMR (100 MHz, DMSO-$d_6$) δ 162.2, 159.9, 156.9, 142.4, 141.7, 136.9, 136.2, 134.5, 133.1, 131.6, 130.4, 130.2, 129.2, 128.8, 128.6, 126.9, 124.3, 121.7, 118.8, 118.5, 117.0, 116.3, 84.4, 74.2, 25.6. HRMS-ESI (+) m/z calculated for $C_{31}H_{28}BN_4O_5$, 547.2153 [M+H]$^+$; found: 547.2156.

Example 122

2,4-Dioxo-10-(4-((4-(4,4,5,5-tetramethyl-1,3,2-dioxaborolan-2-yl)benzyl)oxy)phenyl)-2,3,41,10-tetrahydropyrimido[4,5-b]quinoline-8-carbonitrile. The title compound was prepared using a procedure similar to that described in Example 101. Yellow solid, 51% yield; $^1$H NMR (600 MHz, DMSO-$d_6$) δ 11.23 (s, 1H), 9.14 (s, 1H), 8.40 (d, J=8.2 Hz, 1H), 7.88 (dd, J=8.1, 1.2 Hz, 1H), 7.74 (d, J=7.9 Hz, 2H), 7.54 (d, J=7.9 Hz, 2H), 7.35 (d, J=8.9 Hz, 2H), 7.30 (d, J=9.0 Hz, 2H), 7.11 (s, 1H), 5.27 (s, 2H), 1.31 (s, 12H). $^{13}$C NMR (100 MHz, DMSO-$d_6$) δ 161.4, 159.1, 158.7, 156.1, 141.6, 140.9, 140.0, 134.5, 134.1, 132.3, 129.4, 128.4, 126.9, 126.1, 123.5, 120.9, 118.0, 117.6, 116.2, 115.5, 83.6, 73.4, 24.5. HRMS-ESI (+) m/z calculated for $C_{31}H_{28}BN_4O_5$, 547.2153 [M+H]$^+$; found: 547.2155.

Example 123

(3-((4-(8-Cyano-2,4-dioxo-3,4-dihydropyrimido [4,5-b]quinolin-10(2H)-yl) phenoxy) methyl) phenyl) boronic acid. The title compound was prepared using a procedure similar to that described in Example 120. Yellow solid, 40% yield; $^1$H NMR (600 MHz, DMSO-$d_6$) δ 11.23 (s, 1H), 9.15 (s, 1H), 8.40 (d, J=8.1 Hz, 1H), 8.10 (s, 2H), 7.94 (s, 1H), 7.88 (d, J=7.9 Hz, 1H), 7.80 (d, J=7.5 Hz, 1H), 7.57 (d, J=7.5 Hz, 1H), 7.41 (t, J=7.5 Hz, 1H), 7.37 (d, J=7.7 Hz, 2H), 7.32 (d, J=8.1 Hz, 2H), 7.13 (s, 1H), 5.22 (s, 2H). $^{13}$C NMR (100 MHz, DMSO-$d_6$) δ 161.9, 159.6, 159.5, 156.7, 142.2, 141.4, 135.9, 134.3, 134.3, 132.9, 130.2, 129.9, 129.8, 128.0, 126.7, 124.0, 121.5, 118.6, 118.2, 116.7, 116.1, 70.5. HRMS-ESI (+) m/z calculated for $C_{25}H_{18}BN_4O_5$, 465.1370 [M+H]$^+$, found: 465.1369.

Example 124

(4-((4-(8-Cyano-2,4-dioxo-3,4-dihydropyrimido [4,5-b] quinolin-10(2H)-yl) phenoxy) methyl) phenyl) boronic acid. The title compound was prepared using a procedure similar to that described in Example 120. Yellow solid, 79% yield; $^1$H NMR (600 MHz, DMSO-$d_6$) δ 11.23 (s, 1H), 9.15 (s, 1H), 8.40 (d, J=8.2 Hz, 1H), 8.07 (s, 2H), 7.88 (d, J=8.2 Hz, 1H), 7.84 (d, J=7.8 Hz, 2H), 7.49 (d, J=7.8 Hz, 2H), 7.36 (d, J=8.8 Hz, 2H), 7.31 (d, J=8.9 Hz, 2H), 7.13 (s, 1H), 5.24 (s, 2H). $^{13}$C NMR (100 MHz, DMSO-$d_6$) δ 161.6, 159.3, 159.1, 156.4, 141.8, 141.1, 138.5, 134.4, 132.6, 129.6, 129.5, 126.9, 126.3, 123.7, 121.2, 118.3, 117.9, 116.4, 115.8, 69.8. HRMS-ESI (+) m/z calculated for $C_{25}H_{18}BN_4O_5$, 465.1370 [M+H]$^+$; found: 465.1372.

Example 125

10-(4-Hydroxyphenyl)-3-methyl-2,4-dioxo-2,3,4,10-tetrahydropyrimido[4,5-b]quinoline-8-carbonitrile (4q). The title compound was prepared using a procedure similar to that described in Example 101. Yellow solid, 81% yield; $^1$H NMR (400 MHz, DMSO-$d_6$) δ 10.04 (s, 1H), 9.19 (s, 1H), 8.43 (d, J=8.1 Hz, 1H), 7.88 (dd, J=8.1, 1.2 Hz, 1H), 7.19 (d, J=8.7 Hz, 2H), 7.15 (s, 1H), 7.03 (d, J=8.7 Hz, 2H), 3.22 (s, 3H). $^{13}$C NMR (150 MHz, DMSO-$d_6$) δ 160.7, 158.0, 157.3, 155.5, 141.4, 141.3, 132.2, 129.0, 127.1, 125.9, 123.3, 120.8, 117.5, 117.2, 116.5, 115.4, 27.2. HRMS-ESI (+) m/z calculated for $C_{19}H_{13}N_4O_3$, 345.0988 [M+H]$^+$; found: 345.0991.

Example 126

10-(4-Hydroxyphenyl)-2,4-dioxo-3-phenyl-2,3,4,10-tetrahydropyrimido[4,5-b]quinoline-8-carbonitrile. (Evans, B., et al., *Tetrahedron Lett*. 1998, 39, 2937-2940). To a suspension of compound 4b (0.1 g, 0.30 mmol, 1.0 eq) in DMF (2 mL) was added phenylboronic acid (0.11 g, 0.91 mmol, 3.0 eq), Cu(OAc)$_2$(0.06 g, 0.30 mmol, 1.0 eq) and stirred at room temperature under air. The reaction was continued until the disappearance of starting material (typically between 24-48 h) and water (10 mL) was added to it. The resulting solution was extracted with EtOAc (3×20 mL), washed with brine and evaporated in vacuo to leave the crude product. The crude product was purified using Combi flash with 0-100% EtOAc in hexane as an eluent to furnish the desired product as pale yellow solid (0.07 g, 56%). $^1$H NMR (400 MHz, DMSO-d$_6$) δ 10.06 (s, 1H), 9.23 (s, 1H), 8.45 (d, J=8.2 Hz, 1H), 7.90 (dd, J=8.2, 1.1 Hz, 1H), 7.47 (t, J=7.5 Hz, 2H), 7.40 (t, J=7.5 Hz, 1H), 7.26-7.22 (m, 4H), 7.19 (s, 1H), 7.05 (d, J=8.7 Hz, 2H). $^{13}$C NMR (150 MHz, DMSO-d$_6$) δ 161.1, 158.4, 158.1, 155.4, 142.0, 141.8, 136.5, 132.6, 129.4, 128.9, 128.7, 127.9, 127.5, 126.4, 123.7, 121.3, 118.2, 117.8, 116.9, 115.9. HRMS-ESI (+) m/z calculated for C$_{24}$H$_{15}$N$_4$O$_3$, 407.1144 [M+H]$^+$; found: 407.1146.

Example 127

3-(4-Fluorophenyl)-10-(4-hydroxyphenyl)-2,4-dioxo-2,3,4,10-tetrahydropyrimido[4,5-b]quinoline-8-carbonitrile. The title compound was prepared using a procedure similar to that described in Example 126. Yellow solid, 30% yield; $^1$H NMR (600 MHz, DMSO-d$_6$) δ 10.09 (s, 1H), 9.24 (s, 1H), 8.46 (d, J=8.2 Hz, 1H), 7.91 (d, J=8.2 Hz, 1H), 7.33-7.27 (m, 4H), 7.24 (d, J=8.6 Hz, 2H), 7.20 (s, 1H), 7.05 (d, J=8.6 Hz, 2H). HRMS-ESI (+) m/z calculated for C$_{24}$H$_{14}$FN$_4$O$_3$, 425.1050 [M+H]$^+$; found: 425.1051.

Example 128

3-(4-Chlorophenyl)-10-(4-hydroxyphenyl)-2,4-dioxo-2,3,4,10-tetrahydropyrimido[4,5-b]quinoline-8-carbonitrile. The title compound was prepared using a procedure similar to that described in Example 126. Yellow solid, 80% yield; $^1$H NMR (600 MHz, DMSO-d$_6$) δ 10.08 (s, 1H), 9.25 (s, 1H), 8.46 (d, J=8.1 Hz, 1H), 7.91 (d, J=8.2 Hz, 1H), 7.54 (d, J=8.5 Hz, 2H), 7.29 (d, J=8.5 Hz, 2H), 7.23 (d, J=8.6 Hz, 2H), 7.20 (s, 1H), 7.05 (d, J=8.6 Hz, 2H). $^{13}$C NMR (150 MHz, DMSO-d$_6$) δ 161.0, 158.4, 158.1, 155.2, 142.0, 141.8, 135.4, 132.6, 132.5, 130.6, 129.3, 128.9, 127.4, 126.5, 123.7, 121.3, 118.1, 117.8, 116.8, 116.0. HRMS-ESI (+) m/z calculated for C$_{24}$H$_{14}$ClN$_4$O$_3$, 441,0754 [M+H]$^+$; found: 441.0756.

Example 129

3-(4-Bromophenyl)-10-(4-hydroxyphenyl)-2,4-dioxo-2,3,4,10-tetrahydropyrimido[4,5-b]quinoline-8-carbonitrile. The title compound was prepared using a procedure similar to that described in Example 126. Yellow solid, 52% yield; $^1$H NMR (600 MHz, DMSO-d$_6$) δ 10.08 (s, 1H), 9.24 (s, 1H), 8.46 (d, J=8.2 Hz, 1H), 7.91 (dd, J=8.2, 1.2 Hz, 1H), 7.73-7.63 (m, 2H), 7.25-7.21 (m, 4H), 7.20 (s, 1H), 7.06-7.03 (m, 2H). $^{13}$C NMR (150 MHz, DMSO-d$_6$) δ 161.7, 159.1, 158.8, 155.8, 142.5, 136.5, 133.4, 132.7, 131.8, 131.5, 130.2, 129.9, 128.1, 127.2, 124.4, 121.7, 118.8, 118.5, 117.7, 116.7. HRMS-ESI (+) m/z calculated for C$_{24}$H$_{14}$BrN$_4$O$_3$, 485.0249 [M+H]$^+$; found: 485.0250.

Example 130

Methyl-3-(8-cyano-10-(4-hydroxyphenyl)-2,4-dioxo-4,10-dihydropyrimido[4,5-b]quinolin-3(2H)-yl)benzoate. The title compound was prepared using a procedure similar to that described in Example 126. Yellow solid, 59% yield; $^1$H NMR (600 MHz, DMSO-d$_6$) δ 10.09 (s, 1H), 9.24 (s, 1H), 8.47 (d, J=7.8 Hz, 1H), 7.99 (d, J=7.4 Hz, 1H), 7.92 (d, J=7.6 Hz, 1H), 7.85 (s, 1H), 7.64 (t, J=7.4 Hz, 1H), 7.55 (d, J=6.8 Hz, 1H), 7.29-7.18 (m, 3H), 7.06 (d, J=7.8 Hz, 2H), 3.87 (s, 3H). $^{13}$C NMR (150 MHz, DMSO-d$_6$) δ 165.9, 161.4, 158.6, 158.4, 155.6, 142.2, 142.0, 137.2, 134.0, 132.9, 130.7, 129.8, 129.8, 129.6, 128.9, 127.7, 126.8, 123.9, 121.6, 118.4, 118.1, 117.1, 116.2, 52.6. HRMS-ESI (+) m/z calculated for C$_{26}$H$_{17}$N$_4$O$_5$, 465.1199 [M+H]$^+$; found: 465.1199.

Example 131

3-(8-cyano-10-(4-hydroxyphenyl)-2,4-dioxo-4,10-dihydropyrimido[4,5-b]quinolin-3(2H)-yl)benzamide. The title compound was prepared using a procedure similar to that described in Example 126. Yellow solid, 72% yield; $^1$H NMR (600 MHz, DMSO-d$_6$) δ 10,08 (s, 1H), 9.26 (s, 1H), 8.47 (d, J=8.2 Hz, 1H), 8.02 (s, 1H), 7.91 (d, J=8.1 Hz, 2H), 7.74 (s, 1H), 7.56 (t, J=7.8 Hz, 1H), 7.44-7.39 (m, 2H), 7.25 (d, J=8.7 Hz, 2H), 7.20 (s, 1H), 7.05 (d, J=8.7 Hz, 2H). $^{13}$C NMR (150 MHz, DMSO-d$_6$) δ 167.3, 161.3, 158.6, 158.3, 155.5, 142.3, 142.0, 136.7, 135.3, 132.8, 131.8, 129.6, 129.1, 128.2, 127.7, 127.1, 126.7, 123.9, 121.6, 118.3, 118.0, 117.1, 116.2. HRMS-ESI (+) in calculated for C$_{25}$H$_{16}$N$_5$O$_4$, 450.1202 [M+H]$^+$; found: 450.1202.

Example 132

Phenyl-(3-(8-cyano-10-(4-hydroxyphenyl)-2,4-dioxo-4,10-dihydropyrimido[4,5-b]quinolin-3(2H)-yl)phenyl)carbamate. The title compound was prepared using a procedure similar to that described in Example 126. Yellow solid, 40% yield; $^1$H NMR (600 MHz, DMSO-d$_6$) δ 10.40 (s, 1H), 10.07 (s, 1H), 9.23 (s, 1H), 8.46 (d, J=8.5 Hz, 1H), 8.05-8.00 (m, 1H), 7.90 (d, J=8.2 Hz, 1H), 7.53 (d, J=8.1 Hz, 1H), 7.44-7.39 (m, 5H), 7.28-7.18 (m, 7H), 7.05 (d, J=8.5 Hz, 2H), 6.93 (d, J=8.1 Hz, 1H). HRMS-ESI (+) m/z calculated for C$_{31}$H$_{20}$N$_5$O$_5$, 542.1464 [M+H]$^+$; found: 542.1465.

Example 133

Phenyl-(4-(8-cyano-10-(4-hydroxyphenyl)-2,4-dioxo-4,10-dihydropyrimido[4,5-b]quinolin-3(2H)-yl)phenyl)carbamate. The title compound was prepared using a procedure similar to that described in Example 126. Yellow solid, 45% yield; $^1$H NMR (600 MHz, DMSO-d$_6$) δ 10.37 (s, 1H), 10.07 (s, 1H), 9.23 (s, 1H), 8.46 (d, J=8.1 Hz, 1H), 7.91 (d, J=8.4 Hz, 1H), 7.58 (d, J=8.2 Hz, 2H), 7.44 (t, J=7.8 Hz, 2H), 7.29-7.24 (m, 5H), 7.18-7.16 (m, 3H), 7.05 (d, J=8.6 Hz, 2H). HRMS-ESI (+) m/z calculated for C$_{31}$H$_{20}$N$_5$O$_5$, 542.1464 [M+H]$^+$; found: 542.1468.

Example 134

Diphenyl-(3-(8-cyano-10-(4-hydroxyphenyl)-2,4-dioxo-4,10-dihydropyrimido[4,5-b]quinolin-3(2H)-yl)phenyl) phosphoramidate. The title compound was prepared using a procedure similar to that described in Example 126. Yellow solid, 58% yield; $^1$H NMR (600 MHz, DMSO-d$_6$) δ 10.10 (s, 1H), 9.25 (s, 1H), 9.01 (d, J=10.2 Hz, 1H), 8.46 (d, J=8.1 Hz, 1H), 7.91 (d, J=8.3 Hz, 1H), 7.41-7.37 (m, 5H), 7.25-7.22 (m, 8H), 7.19 (s, 1H), 7.15 (d, J=8.1 Hz, 1H), 7.09 (s, 1H), 7.05 (d, J=8.3 Hz, 2H), 6.85 (d, J=7.8 Hz, 1H). $^{13}$C NMR (150 MHz, DMSO-d$_6$) δ 161.3, 158.5, 158.3, 155.5, 150.1, 142.0, 140.5, 137.5, 132.9, 132.6, 130.3, 130.0, 129.7, 129.4, 127.7, 126.5, 125.8, 125.4, 123.9, 120.6, 120.2, 118.4, 118.0, 117.2, 116.8, 116.1. HRMS-ESI (+) m/z calculated for C$_{35}$H$_{25}$N$_5$O$_6$P, 654.1542 [M+H]$^+$; found: 654.1545.

Example 135

Diphenyl-(4-(8-cyano-10-(4-hydroxyphenyl)-2,4-dioxo-4,10-dihydropyrimido[4,5-b] quinolin-3(2H)-yl)phenyl) phosphoramidate. The title compound was prepared using a procedure similar to that described in Example 126. Yellow solid, 54% yield; $^1$H NMR (600 MHz, DMSO-d$_6$) δ 10.07 (s, 1H), 9.22 (s, 1H), 9.04 (s, 1H), 8.46 (s, 1H), 7.90 (s, 1H), 7.45-7.43 (m, 3H), 7.31-7.12 (m, 14H), 7.7-7.05 (m, 2H). $^{13}$C NMR (150 MHz, DMSO-d$_6$) δ 161.7, 158.8, 158.5, 156.0, 150.6, 150.5, 142.4, 142.3, 139.8, 133.1, 130.6, 130.5, 129.9, 128.0, 126.8, 125.8, 124.2, 121.8, 120.6, 120.5, 118.6, 118.3, 117.3, 116.4, HRMS-ESI (+) m/z calculated for C$_{36}$H$_{25}$N$_5$O$_6$P, 654.1542 [M+H]$^+$; found: 654.1544.

Example 136

Diphenyl-(4-(8-cyano-10-(4-hydroxyphenyl)-2,4-dioxo-4,10-dihydropyrimido[4,5-b] quinolin-3(2H)-yl)benzyl) phosphoramidate. The title compound was prepared using a procedure similar to that described in Example 126. Yellow solid, 71% yield; $^1$H NMR (600 MHz, DMSO-d$_6$) δ 10.07 (s, 1H), 9.23 (s, 1H), 8.46 (d, J=8.2 Hz, 1H), 7.90 (d, J=8.2 Hz, 1H), 7.40 (t, J=7.8 Hz, 4H), 7.34 (d, J=7.9 Hz, 2H), 7.24 (d, J=8.4 Hz, 1H), 7.23-7.18 (m, 7H), 7.14 (d, J=8.0 Hz, 2H), 7.05 (d, J=8.5 Hz, 2H), 6.47-6.42 (m, 1H), 4.20 (dd, J=12.7, 7.1 Hz, 2H). HRMS-ESI (+) m/z calculated for C$_{37}$H$_{27}$N$_5$O$_6$P, 668.1699 [M+H]$^+$; found: 668.1701.

Example 137

3-(4-Chlorophenyl)-10-(3-hydroxyphenyl)-2,4-dioxo-2, 3,4,10-tetrahydropyrimido[4,5-b]quinoline-8-carbonitrile. The title compound was prepared using a procedure similar to that described in Example 126. Yellow solid, 65% yield; $^1$H NMR (600 MHz, DMSO-d$_6$) δ 10.09 (s, 1H), 9.26 (s, 1H), 8.47 (d, J=8.2 Hz, 1H), 7.92 (dd, J=8.2, 1.2 Hz, 1H), 7.56-7.50 (m, 3H), 7.29 (d, J=8.6 Hz, 2H), 7.17 (s, 1H), 7.07 (dd, J=8.2, 1.7 Hz, 1H), 6.86 (d, J=7.8 Hz, 1H), 6.83 (d, J=2.0 Hz, 1H). $^{13}$C NMR (100 MHz, DMSO-d$_6$) δ 160.8, 158.9, 157.4, 155.0, 141.9, 140.9, 137.2, 135.2, 132.4, 132.3, 131.1, 130.4, 128.7, 126.3, 123.4, 121.0, 118.2, 117.9, 117.6, 116.8, 115.8, 115.0. HRMS-ESI (+) m/z calculated for C$_{24}$H$_{14}$ClN$_4$O$_3$, 441.0754 [M+H]$^+$; found: 441.0749.

Example 138

3-(3-Chlorophenyl)-10-(3-hydroxyphenyl)-2,4-dioxo-2, 3,4,10-tetrahydropyrimido[4,5-b]quinoline-8-carbonitrile. The title compound was prepared using a procedure similar to that described in Example 126. Yellow solid, 51% yield; $^1$H NMR (600 MHz, DMSO-d$_6$) δ 10.09 (s, 1H), 9.26 (s, 1H), 8.48 (d, J=8.2 Hz, 1H), 7.92 (dd, J=8.1, 1.3 Hz, 1H), 7.54-7.48 (m, 3H), 7.40 (t, J=1.8 Hz, 1H), 7.25 (dt, J=7.4, 1.6 Hz, 1H), 7.18 (s, 1H), 7.07 (dd, J=8.3, 1.7 Hz, 1H), 6.87-6.84 (m, 1H), 6.83 (t, J=2.1 Hz, 1H). $^{13}$C NMR (100 MHz, DMSO-d$_6$) δ 160.8, 158.9, 157.4, 155.0, 141.9, 140.9, 137.2, 135.2, 132.4, 132.3, 131.1, 130.4, 128.7, 126.3, 123.4, 121.0, 118.2, 117.9, 117.6, 116.8, 115.8, 115.0. HRMS-ESI (+) m/z calculated for C$_{24}$H$_{14}$ClN$_4$O$_3$, 441.0754 [M+H]$^+$; found: 441.0755.

Example 139

3-(3,4-Dichlorophenyl)-10-(3-hydroxyphenyl)-2,4-dioxo-2,3,4,10-tetrahydropyrimido[4,5-b]quinoline-8-carbonitrile. The title compound was prepared using a procedure similar to that described in Example 126. Yellow solid, 48% yield; $^1$H NMR (600 MHz, DMSO-d$_6$) δ 10.11 (s, 1H), 9.28 (s, 1H), 8.49 (d, J=8.2 Hz, 1H), 7.94 (dd, J=8.2, 1.5 Hz, 1H), 7.77 (d, J=8.5 Hz, 1H), 7.65 (d, J=2.3 Hz, 1H), 7.52 (t, J=8.0 Hz, 1H), 7.32 (dd, J=8.5, 2.3 Hz, 1H), 7.19 (s, 1H), 7.07 (dd, J=8.2, 1.5 Hz, 1H), 6.91-6.78 (m, 2H). $^{13}$C NMR (100 MHz, DMSO-d$_6$) δ 161.5, 159.7, 158.2, 155.5, 142.8, 141.7, 138.0, 137.1, 133.2, 131.9, 131.7, 131.5, 131.4, 130.0, 127.3, 124.2, 121.9, 119.0, 118.6, 118.4, 117.6, 116.7, 115.8. HRMS-ESI (+) m/z calculated for C$_{24}$H$_{13}$Cl$_2$N$_4$O$_3$, 475.0365 [M+H]$^+$; found: 475.0367.

Example 140

3-(4-Chlorophenyl)-2,4-dioxo-10-phenyl-2,3,4,10-tetrahydropyrimido[4,5-b]quinoline-8-carbonitrile. The title compound was prepared using a procedure similar to that described in Example 126. Yellow solid, 62% yield; $^1$H NMR (600 MHz, DMSO-d$_6$) δ 9.29 (s, 1H), 8.49 (d, J=7.9 Hz, 1H), 7.94 (dd, J=8.1, 1.4 Hz, 1H), 7.79-7.73 (m, 2H), 7.71-7.68 (m, 1H), 7.58-7.53 (m, 2H), 7.50-7.48 (m, 2H), 7.32-7.27 (m, 2H), 7.09 (s, 1H). $^{13}$C NMR (100 MHz, DMSO-d$_6$) δ 161.4, 158.3, 155.6, 142.7, 141.7, 137.1, 135.8, 133.2, 133.0, 131.1, 131.0, 130.4, 129.4, 128.8, 127.1, 124.2, 121.6, 118.6, 118.2, 116.5. HRMS-ESI m/z calculated for C$_{24}$H$_{14}$ClN$_4$O$_2$, 425.0805 [M+H]$^+$; found: 425.0808.

Example 141

N-(3-(3-(4-Chlorophenyl)-8-cyano-2,4-dioxo-3,4-dihydropyrimido[4,5-b]quinolin-10(2H)-yl)phenyl)methanesulfonamide (23p). The title compound was prepared using a procedure similar to that described in Example 126. Yellow solid, 52% yield; $^1$H NMR (600 MHz, DMSO-d$_6$) δ 10.22 (s, 1H), 9.26 (s, 1H), 8.47 (d, J=8.2 Hz, 1H), 7.92 (dd, J=8.1, 1.4 Hz, 1H), 7.68 (t, J=8.1 Hz, 1H), 7.57-7.51 (m, 2H), 7.46 (dd, J=8.3, 1.4 Hz, 1H), 7.31-7.29 (m, 2H), 7.28 (d, J=2.1 Hz, 1H), 7.27 (t, J=2.1 Hz, 1H), 7.19-7.16 (m, 1H), 3.12 (s, 3H). $^{13}$C NMR (150 MHz, DMSO-d$_6$) δ 161.3, 158.1, 155.5, 142.6, 141.5, 140.9, 137.7, 135.7, 133.0, 132.9, 131.8, 131.0, 129.3, 127.2, 124.1, 123.5, 121.7, 120.8, 118.7, 118.5, 118.1, 116.6, 40.5. HRMS-ESI (+) m/z calculated for C$_{25}$H$_{17}$ClN$_5$O$_4$S, 518.0690 [M+H]$^+$; found: 518.0691.

Example 142

N-(4-(3-(4-chlorophenyl)-8-cyano-2,4-dioxo-3,4-dihydropyrimido[4,5-b]quinolin-10(2H)-yl)phenyl)methanesulfonamide (23q). The title compound was prepared using a procedure similar to that described in Example 126. Yellow solid, 43% yield; $^1$H NMR (600 MHz, DMSO-d$_6$) δ 10.28 (s, 1H), 9.26 (s, 1H), 8.47 (d, J=8.2 Hz, 1H), 7.92 (dd, J=8.2, 1.2 Hz, 1H), 7.56-7.52 (m, 2H), 7.49 (d, J=8.8 Hz, 2H), 7.41 (d, J=8.8 Hz, 2H), 7.30-7.26 (m. 2H), 7.25 (s, 1H), 3.20 (s, 3H), $^{13}$C NMR (150 MHz, DMSO-d$_6$) δ 161.4, 158.4, 155.5, 142.6, 141.8, 140.2, 135.7, 133.0, 132.9, 131.7, 131.0, 129.8, 129.3, 127.1, 124.1, 121.7, 120.4, 118.4, 118.2, 116.5, 40.5. HRMS-ESI (+) m/z calculated for $C_{25}H_{17}ClN_5O_4S$, 518.0690 [M+H]$^+$; found: 518.0694.

Example 143

(3-(4-(8-Chloro-2,4-dioxo-3,4-dihydropyrimido[4,5-b] quinolin-10(2H)yl)phenoxy)phenyl) boronic acid. The title compound was prepared using a procedure similar to that described in Example 120. Yellow solid, 39% yield; $^1$H NMR (600 MHz, DMSO-d$_6$) δ 11.14 (s, 1H), 9.12 (s, 1H), 8.27 (d, J=8.5 Hz, 1H), 8.18 (s, 2H), 7.70-7.63 (m, 2H), 7.59 (d, J=8.5 Hz, 1H), 7.47 (t, J=7.7 Hz, 1H), 7.42 (d, J=8.7 Hz, 2H), 7.29 (d, J=8.1 Hz, 1H), 7.22 (d, J=8.7 Hz. 2H), 6.73 (s, 1H), $^{13}$C NMR (100 MHz, DMSO-d$_6$) δ 162.2. 159.5, 158.7, 156.8, 155.2, 143.2, 142.2, 139.9, 133.7, 131.8, 130.9, 130.5, 129.9, 125.8, 125.2, 122.4, 120.3, 119.2, 116.8, 116.4. HRMS-ESI (+) m/z calculated for $C_{23}H_{16}BClN_3O_5$, 460, 0872 [M+H]$^+$; found: 460.0873.

Example 144

Cell Permeability. An issue associated with reported deazaflavin analogues is poor cell permeability, which is well correlated with poor efficacy in cancer cells despite high potency in the biochemical assay. The cell permeability of representative compounds of the invention can be evaluated using a PAMPA assay (Ottaviani, G., et al., *J. Med. Chem.* 2006, 49, 3948-3954).

Example 145

Biochemical Potency. The enzymatic activity of TDP2 was measured with a SUMO hTDP2cat fluorescence-based biochemical assay. To a black 384-well plate, 10 μL of compound solution (in reaction buffer, concentration 2-fold higher than the tested concentration) was added, followed by addition of 5 μL of SUMO hTDP2cat enzyme (12.5 pM, final concentration of 3.13 pM). After a pre-incubation period of 10 minutes, 5 μL of substrate 5'-(6-FAM-NHS) (5'-tyrosine)GATCT(3'-BHQ-1)-3' (1 μM, final concentration of 0.25 μM) was added, and the reaction was allowed to proceed at 25° C. for 60 minutes. The fluorescence was measured, and the data was processed as described previously for 14M_zTDP2. Results are shown in Table 1.

Example 146

Efficacy in Cancer Cells. The survival rate of DT40 lymphoma cells treated with representative compounds at increasing concentrations was studied in the presence of clinical Top2 poison etoposide (ETP) at two different doses (0.1 μM and 0.15 μM). Results are shown in FIGS. 2A-2D. Among previously reported deazaflavin TDP2 inhibitors, compound 5-I:

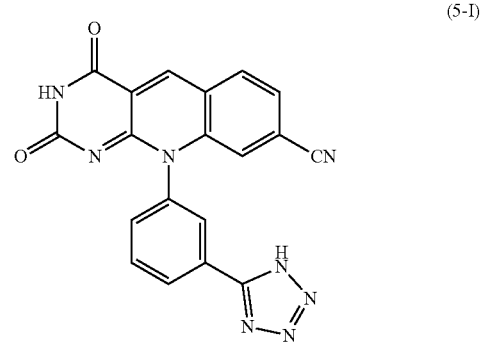 [SMILES: N#Cc1ccc2cc3c(=O)[nH]c(=O)nc-3n(-c3cccc(-c4nnn[nH]4)c3)c2c1]

(5-I)

was the most potent in biochemical assay (IC$_{50}$=40 nM). However, in cancer cells compound 5-I showed weak sensitizing effect with maximal efficacy around 10% cell viability at a high concentration (50 μM) of compound 5-I. In contrast, the compounds of the invention that were tested typically demonstrated a maximal efficacy of closed to 1% cancer cell survival at a much lower concentration (<10 μM, FIGS. 2A-2D). For example, with Example 128 (FIG. 2A) and Example 138 (FIG. 2B), the efficacy reached plateau at around 6 μM. Example 123 (FIG. 2C) showed the most pronounced sensitizing effect as maximal efficacy of 1% cancer cell survival was achieved at a concentration of Example 123<1 μM).

TABLE 1

| Example | R$^1$ | R$^2$ | hTdp2 (Rec) IC$_{50}$ (μM) |
|---|---|---|---|
| 101 | H | 4-(F$_3$CO)-phenyl | 1.03 ± 0.10 |

TABLE 1-continued
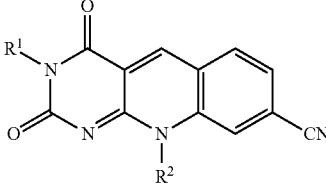
| Example | R¹ | R² | hTdp2 (Rec) IC$_{50}$ (μM) |
|---|---|---|---|
| 102 | H | 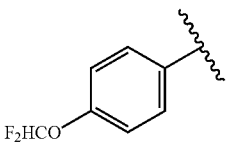 | 0.880 ± 0.059 |
| 103 | H | 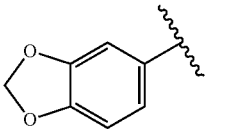 [SMILES: *c1ccc2c(c1)OCO2] | 0.964 ± 0.015 |
| 104 | H | 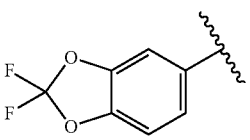 [SMILES: *c1ccc2c(c1)OC(F)(F)O2] | 1.53 ± 0.11 |
| 105 | H | 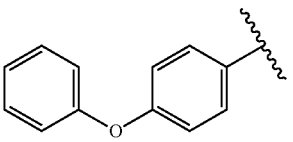 [SMILES: *c1ccc(Oc2ccccc2)cc1] | 1.13 ± 0.06 |
| 106 | H | 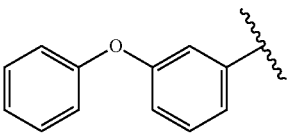 [SMILES: *c1cccc(Oc2ccccc2)c1] | 0.301 ± 0.004 |
| 107 | H | 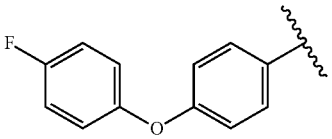 [SMILES: *c1ccc(Oc2ccc(F)cc2)cc1] | 3.80 ± 0.27 |
| 108 | H | 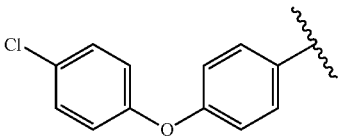 [SMILES: *c1ccc(Oc2ccc(Cl)cc2)cc1] | >10 |
| 109 | H | 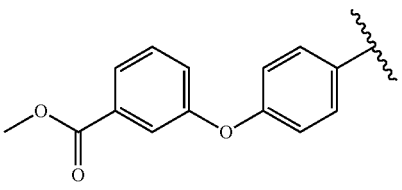 [SMILES: *c1ccc(Oc2cccc(C(=O)OC)c2)cc1] | 0.934 ± 0.05 |

TABLE 1-continued
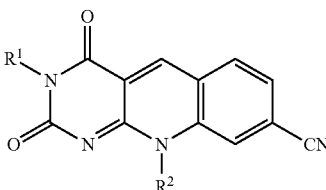
| Example | R¹ | R² | hTdp2 (Rec) IC$_{50}$ (μM) |
|---|---|---|---|
| 110 | H | 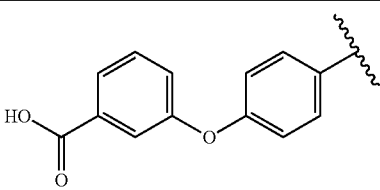 | 0.186 ± 0.006 |
| 111 | H | 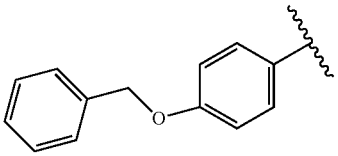 [SMILES: *c1ccc(OCc2ccccc2)cc1] | 0.196 ± 0.019 |
| 112 | H | 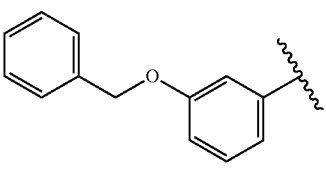 [SMILES: *c1cccc(OCc2ccccc2)c1] | 0.383 ± 0.019 |
| 113 | H | 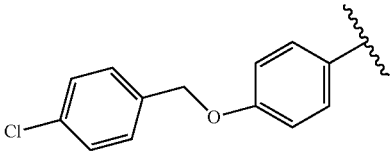 [SMILES: *c1ccc(OCc2ccc(Cl)cc2)cc1] | 1.60 ± 0.16 |
| 114 | H | 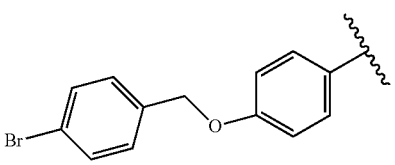 [SMILES: *c1ccc(OCc2ccc(Br)cc2)cc1] | 1.31 ± 0.03 |
| 115 | H | 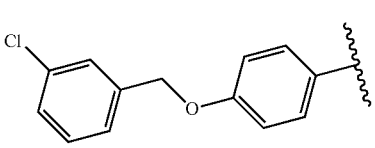 [SMILES: *c1ccc(OCc2cccc(Cl)c2)cc1] | 0.993 ± 0.09 |
| 116 | H | 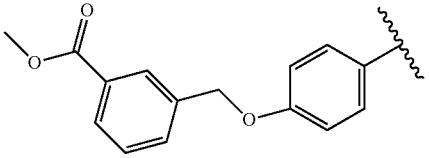 [SMILES: *c1ccc(OCc2cccc(C(=O)OC)c2)cc1] | 0.153 ± 0.010 |
| 117 | H | 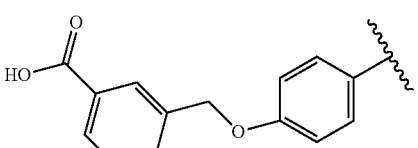 | 0.131 ± 0.005 |

TABLE 1-continued
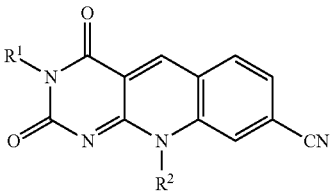
| Example | R¹ | R² | hTdp2 (Rec) IC$_{50}$ (μM) |
|---|---|---|---|
| 118 | H | 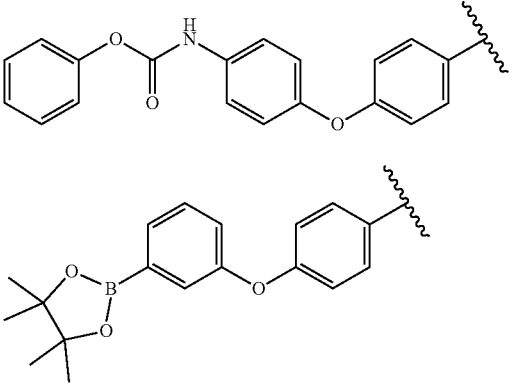 | 0.795 ± 0.040 |
| 119 | H | 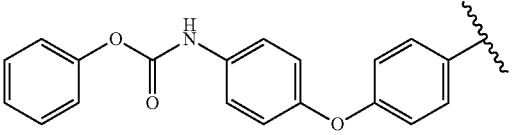 [SMILES: *c1ccc(Oc2ccc(NC(=O)Oc3ccccc3)cc2)cc1] | 0.00828 ± 0.00044 |
| 120 | H | 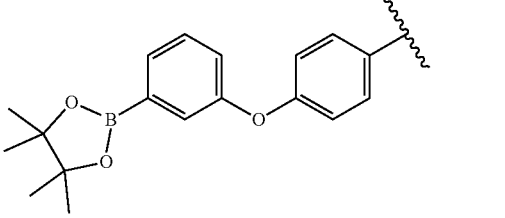 | 0.00501 ± 0.00069 |
| 121 | H | 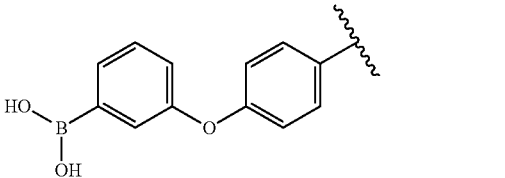 [SMILES: *c1ccc(Oc2cccc(B(O)O)c2)cc1] | 0.047 ± 0.004 |
| 122 | H | 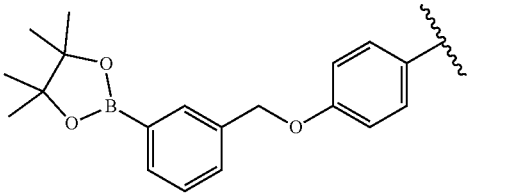 [SMILES: *c1ccc(OCc2cccc(B3OC(C)(C)C(C)(C)O3)c2)cc1] | 0.359 ± 0.032 |
| 123 | H | 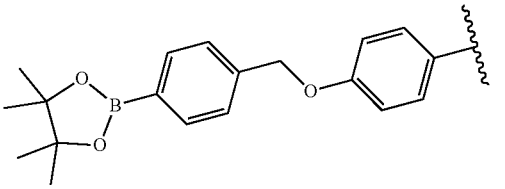 [SMILES: *c1ccc(OCc2ccc(B3OC(C)(C)C(C)(C)O3)cc2)cc1] | 0.039 ± 0.003 |
| 124 | H | 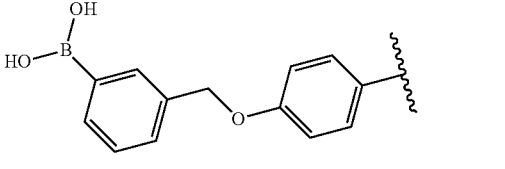 [SMILES: *c1ccc(OCc2cccc(B(O)O)c2)cc1] | 0.239 ± 0.018 |

TABLE 1-continued
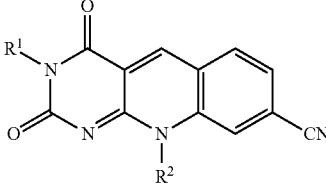
| Example | R¹ | R² | hTdp2 (Rec) IC$_{50}$ (μM) |
|---|---|---|---|
| 125 | CH₃ | 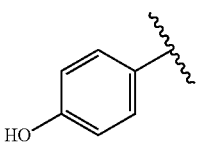 | 0.317 ± 0.017 |
| 126 | 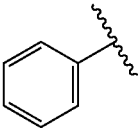 [SMILES: *c1ccccc1] | 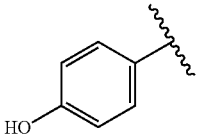 | 0.0331 ± 0.0014 |
| 127 | 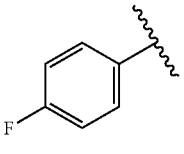 | 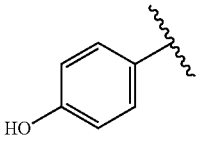 | 0.0704 ± 0.0029 |
| 128 | 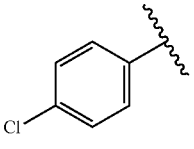 [SMILES: *c1ccc(Cl)cc1] | 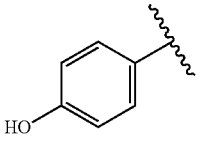 [SMILES: *c1ccc(O)cc1] | 0.0328 ± 0.0024 |
| 129 | 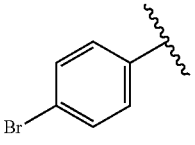 [SMILES: *c1ccc(Br)cc1] | 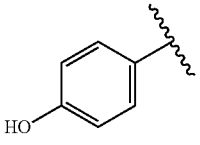 | 0.0647 ± 0.0029 |
| 130 | 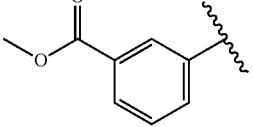 | 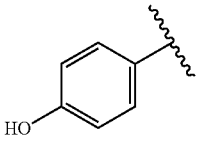 | 0.0380 ± 0.0003 |
| 131 | 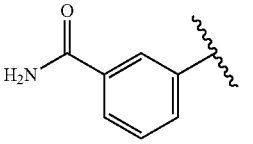 [SMILES: *c1cccc(C(N)=O)c1] | 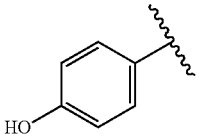 [SMILES: *c1ccc(O)cc1] | 0.0350 ± 0.0002 |
| 132 | 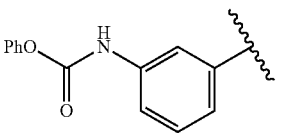 [SMILES: *c1cccc(NC(=O)Oc2ccccc2)c1] | 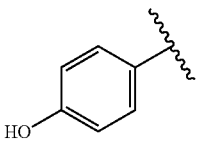 [SMILES: *c1ccc(O)cc1] | 0.119 ± 0.004 |

TABLE 1-continued
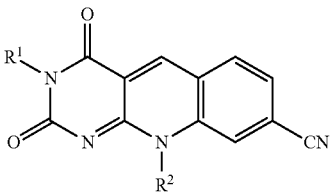
| Example | R¹ | R² | hTdp2 (Rec) IC$_{50}$ (μM) |
|---|---|---|---|
| 133 | 4-(PhOC(O)NH)-C₆H₄- | 4-HO-C₆H₄- | 0.059 ± 0.004 |
| 134 | 3-((PhO)₂P(O)NH)-C₆H₄- | 4-HO-C₆H₄- | 0.277 ± 0.011 |
| 135 | 4-((PhO)₂P(O)NH)-C₆H₄- | 4-HO-C₆H₄- | 0.185 ± 0.009 |
| 136 | 4-((PhO)₂P(O)NHCH₂)-C₆H₄- | 4-HO-C₆H₄- | 0.119 ± 0.003 |
| 137 | 4-Cl-C₆H₄- | 3-HO-C₆H₄- | 0.00725 ± 0.00031 |
| 138 | 3-Cl-C₆H₄- | 3-HO-C₆H₄- | 0.0198 ± 0.0018 |
| 139 | 3,4-diCl-C₆H₃- | 3-HO-C₆H₄- | 0.0136 ± 0.0003 |
| 140 | 4-Cl-C₆H₄- | C₆H₅- | 0.274 ± 0.015 |

TABLE 1-continued

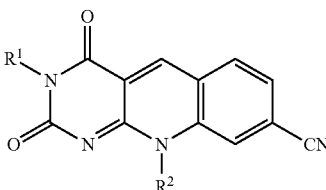

| Example | R¹ | R² | hTdp2 (Rec) IC$_{50}$ (μM) |
|---|---|---|---|
| 141 | 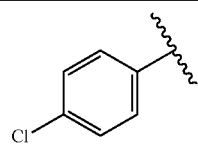 | 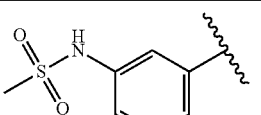 | 0.00609 ± 0.00059 |
| 142 | 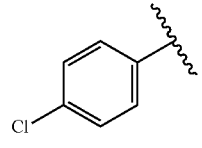 | 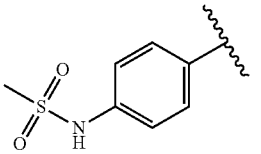 [SMILES: *c1ccc(NS(C)(=O)=O)cc1] | 0.00649 ± 0.00041 |
| 143 | 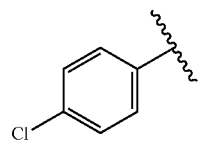 | 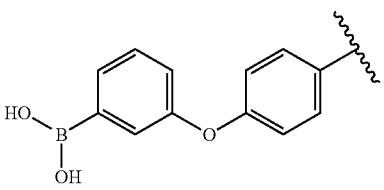 [SMILES: *c1ccc(Oc2cccc(B(O)O)c2)cc1] | 0.00385 ± 0.00037 |

Example 147

The following illustrate representative pharmaceutical dosage forms, containing a compound of formula (I) ('Compound X'), for therapeutic or prophylactic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |

| (iii) Capsule | mg/capsule |
|---|---|
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X= (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X= (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 ml |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula (I), (II) or (III):

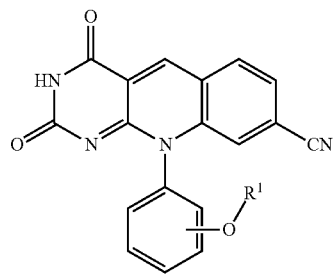

(I)

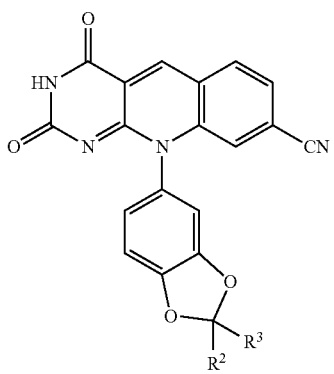

(II)

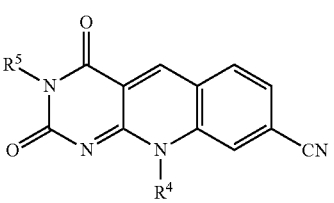

(III)

or a pharmaceutically acceptable salt thereof, wherein:
$R^1$ is phenyl, benzyl, or $(C_1-C_3)$alkyl optionally substituted with halo, wherein the phenyl or benzyl is optionally substituted with one or more groups $R^x$ that are independently selected from the group consisting of halo, carboxy, $(C_1-C_6)$alkoxycarbonyl, halo$(C_1-C_6)$alkoxy- carbony -C(=O)NR$^b$R$^c$, -NHP(=O)(OR$^d$)(OR$^e$), -NHC(=O)OR$^f$, -B(OR$^g$)(OR$^h$), -S(O)$_2$F, -P(=O)(F)(OR$^k$),

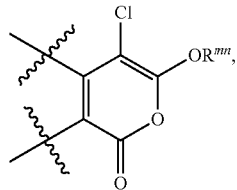

and $(C_1-C_3)$alkyl substituted with halo, $(C_1-C_6)$ alkoxycarbonyl, halo$(C_1-C_6)$alkoxycarbonyl, -C(=O)NR$^b$R$^c$, -NHP(=O)(OR$^d$)(OR$^e$), -NHC(=O)OR$^f$, -B(OR$^g$)(OR$^h$), -S(O)$_2$F, or -P(=O)(F)(OR$^k$);
$R^b$ and $R^c$ are each independently H or $(C_1-C_6)$alkyl;
$R^d$ and $R^e$ are each independently H, $(C_1-C_6)$alkyl, or phenyl;
$R^f$ is H, $(C_1-C_6)$alkyl, or phenyl;
$R^g$ and $R^h$ are each independently H or $(C_1-C_6)$alkyl, or $R^g$ and $R^h$ taken together with the boron to which they are attached form a 5- or 6-membered ring that is optionally substituted with one or more groups independently selected from $(C_1-C_6)$alkyl;
$R^k$ is $(C_1-C_6)$alkyl; and
$R^{mn}$ is H, $(C_1-C_6)$alkyl, or phenyl;
$R^2$ and $R^3$ are each independently selected from H, halo or $(C_1-C_6)$alkyl that is optionally substituted with halo;
$R^4$ is phenyl, wherein the phenyl is optionally substituted with one or more groups $R^{xx}$ that are independently selected from the group consisting of halo, carboxy, -OH, -OR$^1$, $(C_1-C_6)$alkoxycarbonyl, halo $(C_1-C_6)$alkoxycarbonyl, -C(=O)NR$^m$R$^n$, -NHP(=O)(OR$^p$)(OR$^q$), -NHC(=O)OR$^s$, -NHS(O)$_2$R$^{ss}$, -B(OR$^t$)(OR$^u$), -S(O)$_2$F, -P(=O)(F)(OR$^v$),

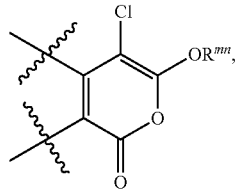

and
$(C_1-C_3)$alkyl that is optionally substituted with halo, $(C_1-C_6)$alkoxycarbonyl, halo$(C_1-C_6)$alkoxy-carbonyl, -C(=O)NR$^m$R$^n$, -N-P(=O)(OR$^p$)(OR$^q$), -NHC(=O)OR$^s$, -B(OR$^t$)(OR$^u$) -S(O)$_2$F, or -P(=O)(F)(OR$^v$);
$R^m$ and $R^n$ are each independently H or $(C_1-C_6)$alkyl;
$R^p$ and $R^q$ are each independently H, $(C_1-C_6)$alkyl, or phenyl;
$R^s$ is H, $(C_1-C_6)$alkyl, or phenyl;
$R^{ss}$ is $(C_1-C_6)$alkyl, or phenyl;
$R^t$ and $R^u$ are each independently H or $(C_1-C_6)$alkyl, or $R^t$ and $R^u$ taken together with the boron and oxygens to which they are attached form a 5- or 6-membered ring that is optionally substituted with one or more groups independently selected from $(C_1-C_6)$alkyl;
$R^v$ is $(C_1-C_6)$alkyl; and
$R^5$ is phenyl, wherein the phenyl is optionally substituted with one or more groups that are independently selected from the group consisting of halo, $(C_1-C_6)$ alkoxycarbonyl, -NHP(=O)(OR$^w$)(OR$^y$), -C(=O)

NR$^z$R$^{aa}$, -NHC(=O)OR$^{bb}$, carboxy, or (C$_1$-C$_3$)alkyl substituted with -NHP(=O)(OR$^w$)(OR$^y$), R$^z$ and R$^{aa}$ are each independently H or (C$_1$-C$_6$)alkyl;

R$^w$ and R$^y$ are each independently H, (C$_1$-C$_6$)alkyl, or phenyl; and

R$^{bb}$ is H, (C$_1$-C$_6$)alkyl, or phenyl.

2. The compound or pharmaceutically acceptable salt of claim 1, which is a compound of formula (I), or a pharmaceutically acceptable salt thereof.

3. The compound or pharmaceutically acceptable salt of claim 2, which is a compound of formula (Ia):

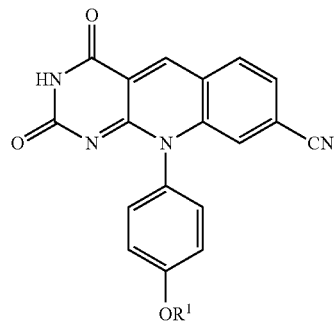

(Ia)

or pharmaceutically acceptable a salt thereof.

4. The compound or pharmaceutically acceptable salt of claim 2, which is a compound of formula (Ib):

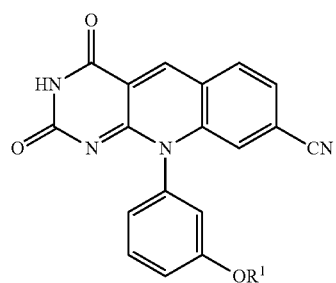

(Ib)

or a pharmaceutically acceptable salt thereof.

5. The compound or pharmaceutically acceptable salt of claim 2, which is a compound of formula (Ic):

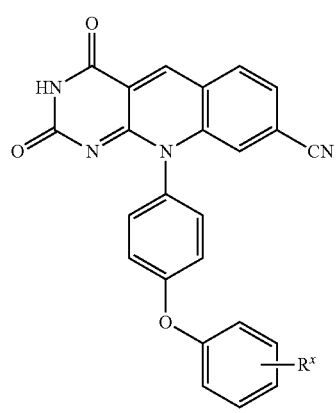

(Ic)

or a pharmaceutically acceptable salt thereof.

6. The compound or pharmaceutically acceptable salt of claim 2, which is a compound of formula (Id):

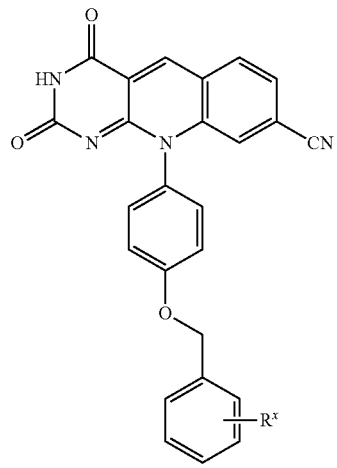

(Id)

7. The compound or pharmaceutically acceptable salt of claim 1, wherein each R$^x$ is independently selected from the group consisting of bromo, chloro, fluoro, carboxy, methoxycarbonyl, aminocarbonyl, -NHP(=O)(OPh)(OPh), -CH$_2$-NHP(=O)(OPh)(OPh), -NHC(=O)OPh, -B(OH)(OH), and

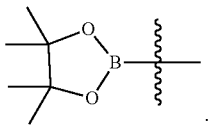 [SMILES: *B1OC(C)(C)C(C)(C)O1]

8. The compound or pharmaceutically acceptable salt of claim selected from the group consisting of:

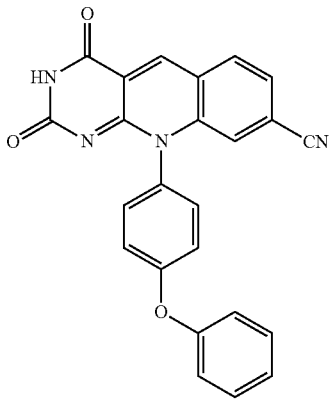

69
-continued
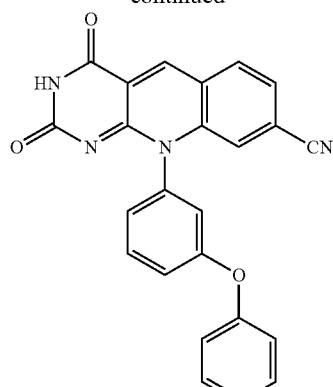
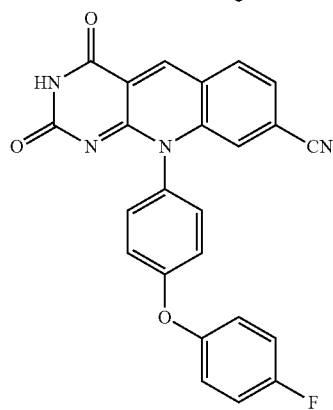
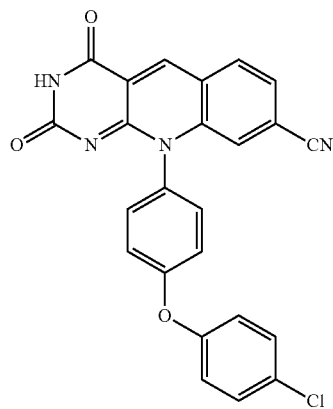
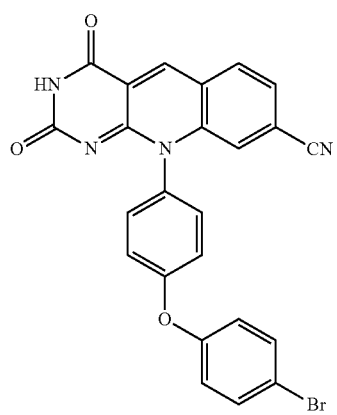
70
-continued
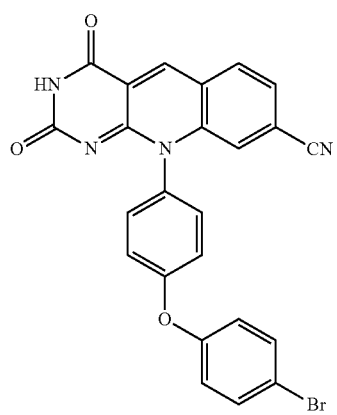
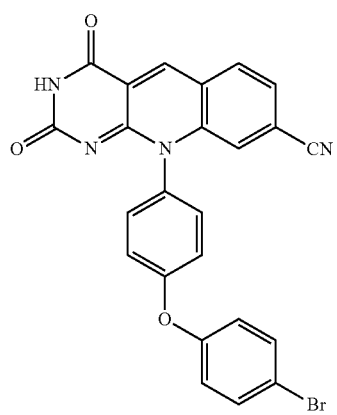
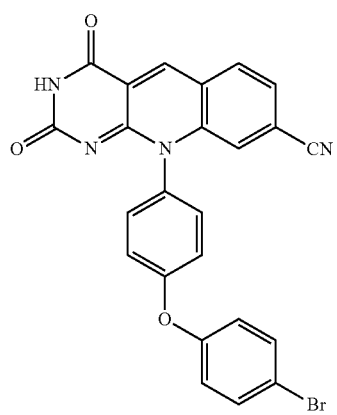
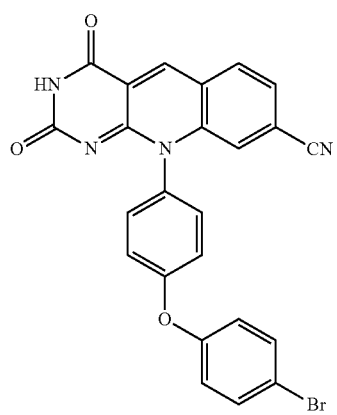

71
-continued
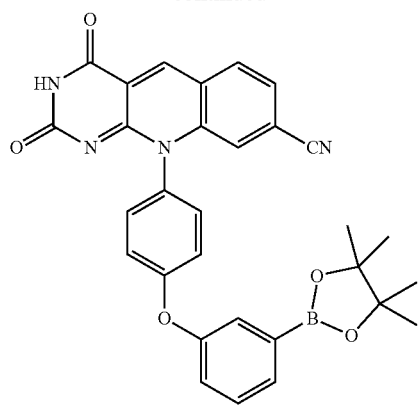
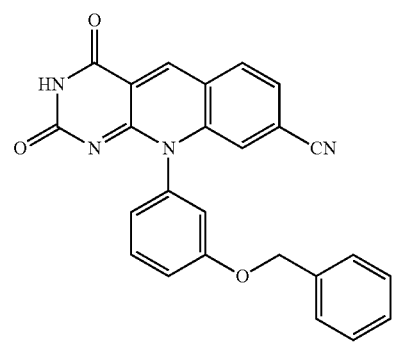
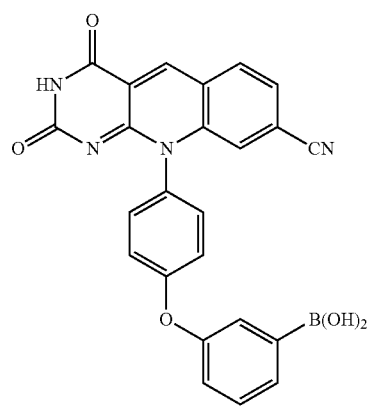
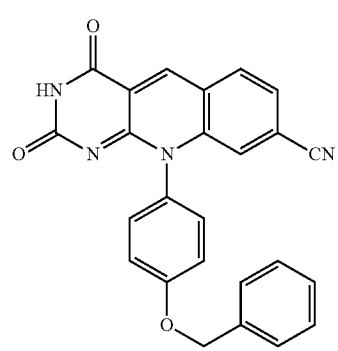
72
-continued
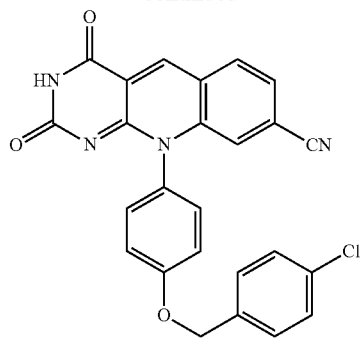
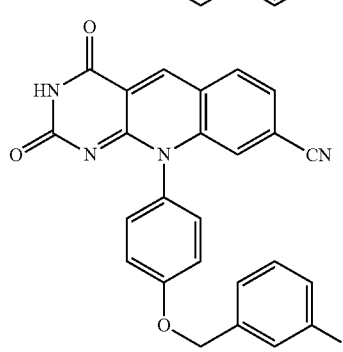
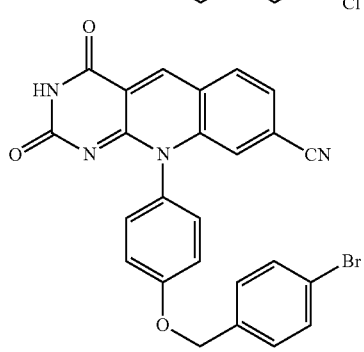
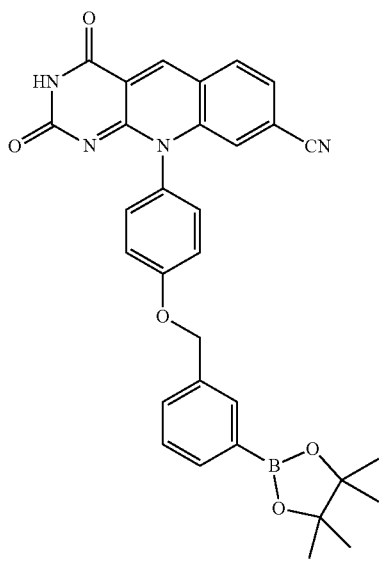

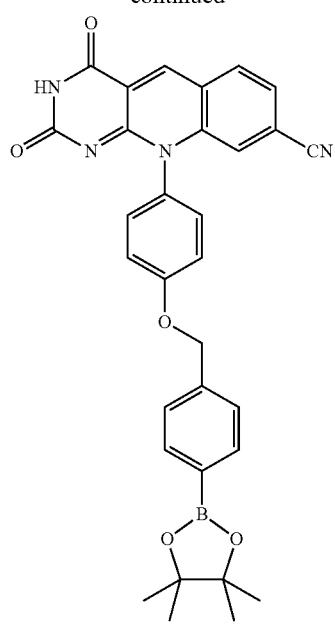
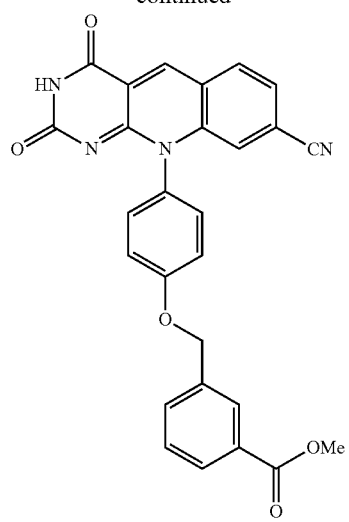
and pharmaceutically acceptable salts thereof.
9. The compound or pharmaceutically acceptable salt of claim 1, which is a compound of formula (II), or a pharmaceutically acceptable salt thereof.
10. The compound or pharmaceutically acceptable salt of claim 9, selected from the group consisting of:

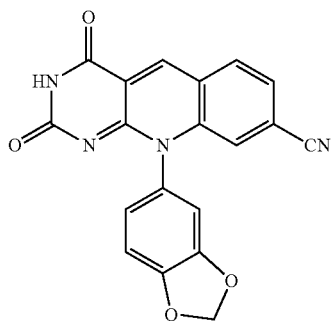

and

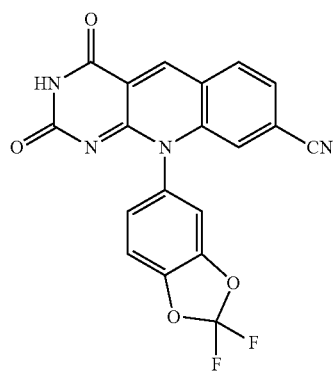

and pharmaceutically acceptable salts thereof.

11. The compound or pharmaceutical salt of claim 1, which is a compound of formula (IIIa):

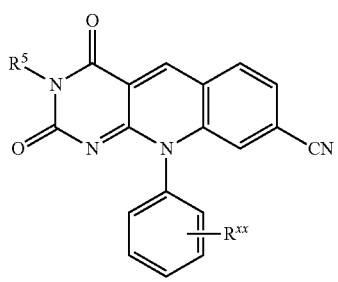

or a pharmaceutically acceptable, salt thereof.

12. The compound or pharmaceutically acceptable salt of claim 11, which is a compound of formula (IIIb):

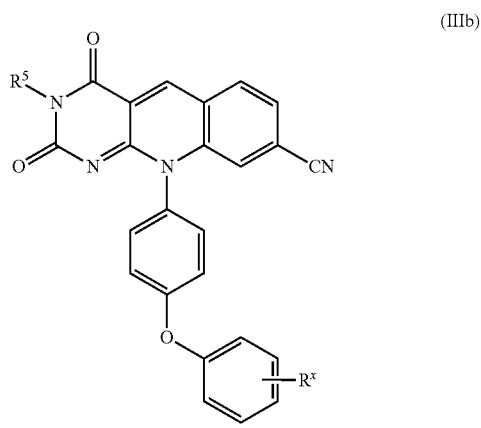

or a pharmaceutically acceptable salt thereof.

13. The compound or pharmaceutically acceptable salt of claim 11, wherein $R^{xx}$ is independently selected from the group consisting of H, OH, -NHS(O)$_2$Me or -B(OH)$_2$.

14. The compound or pharmaceutically acceptable salt of claim 11, wherein $R^5$ is phenyl optionally substituted with one or more groups that are independently selected from the group consisting of halo, carboxy, (C$_1$-C$_6$)alkoxycarbonyl, -NHP(=O)(OPh)(OPh), -C(=O)NH$_2$, -NHC(=O)OPh, and (C$_1$-C$_3$)alkyl substituted with -NHP(=O)(OPh)(OPh).

15. The compound or pharmaceutically acceptable of claim 1, selected from the group consisting of:

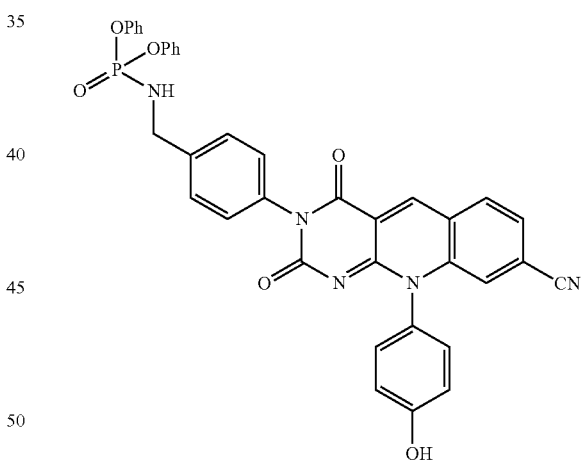

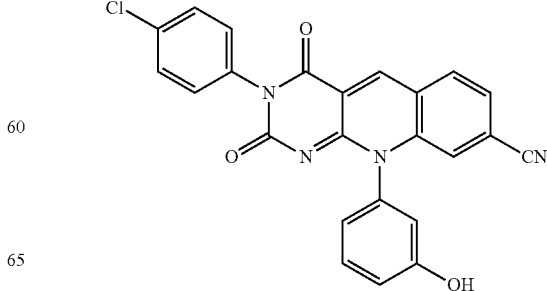

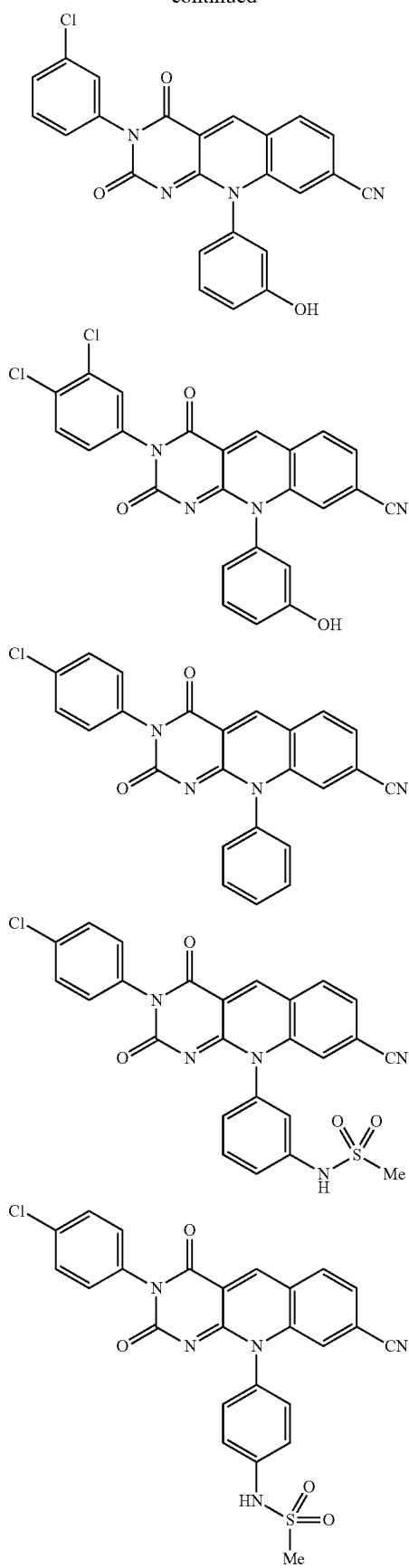
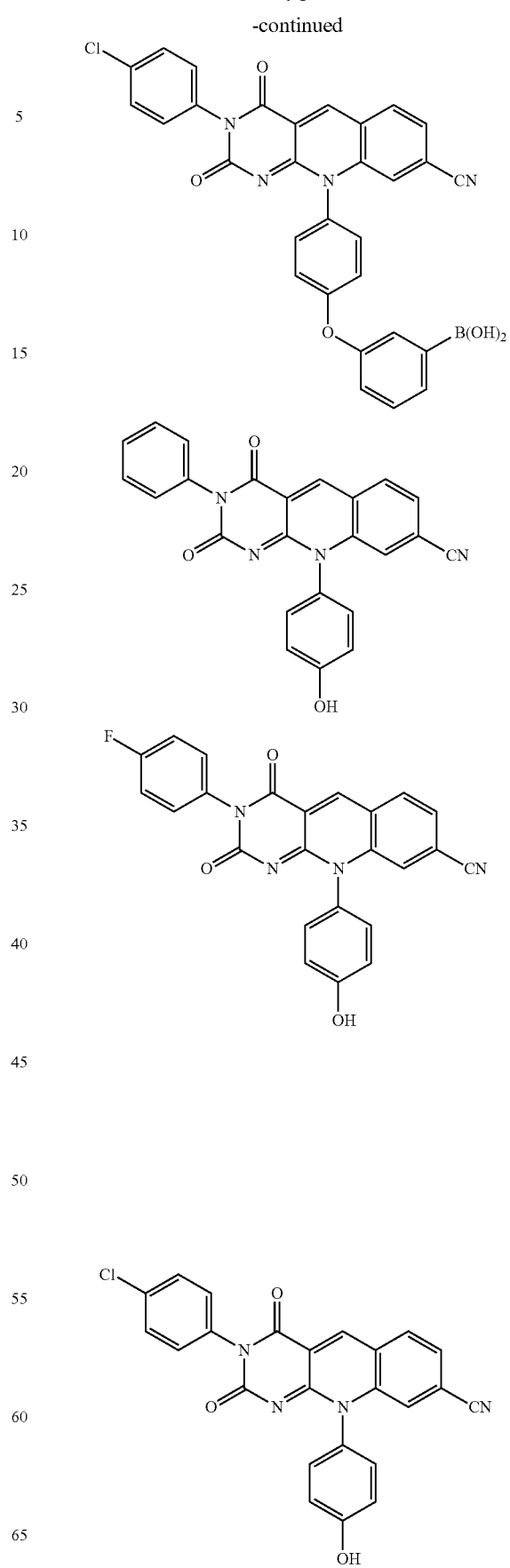

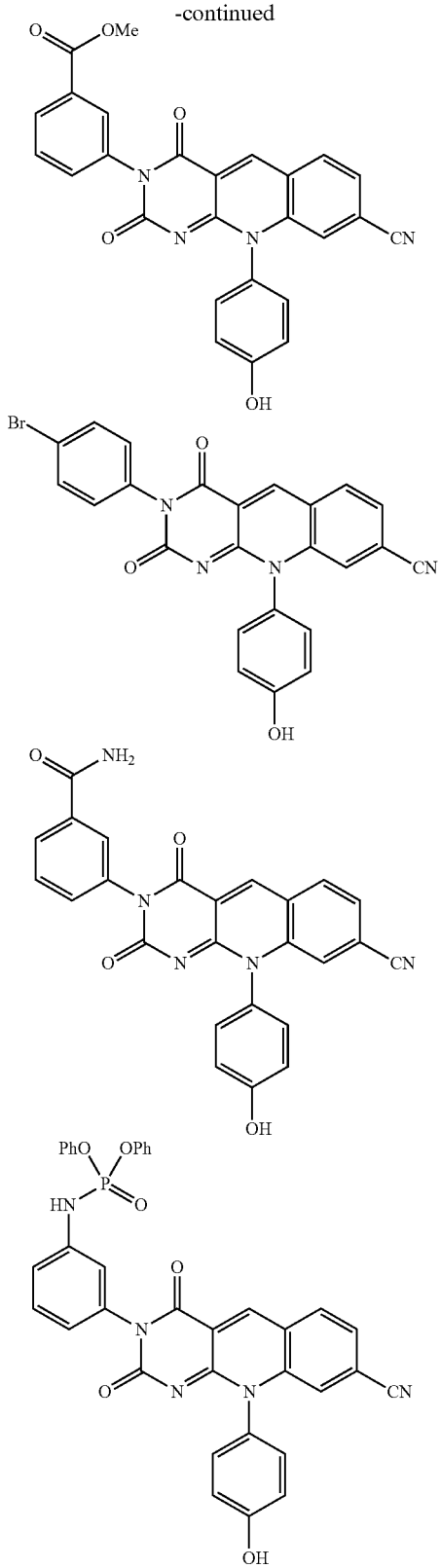
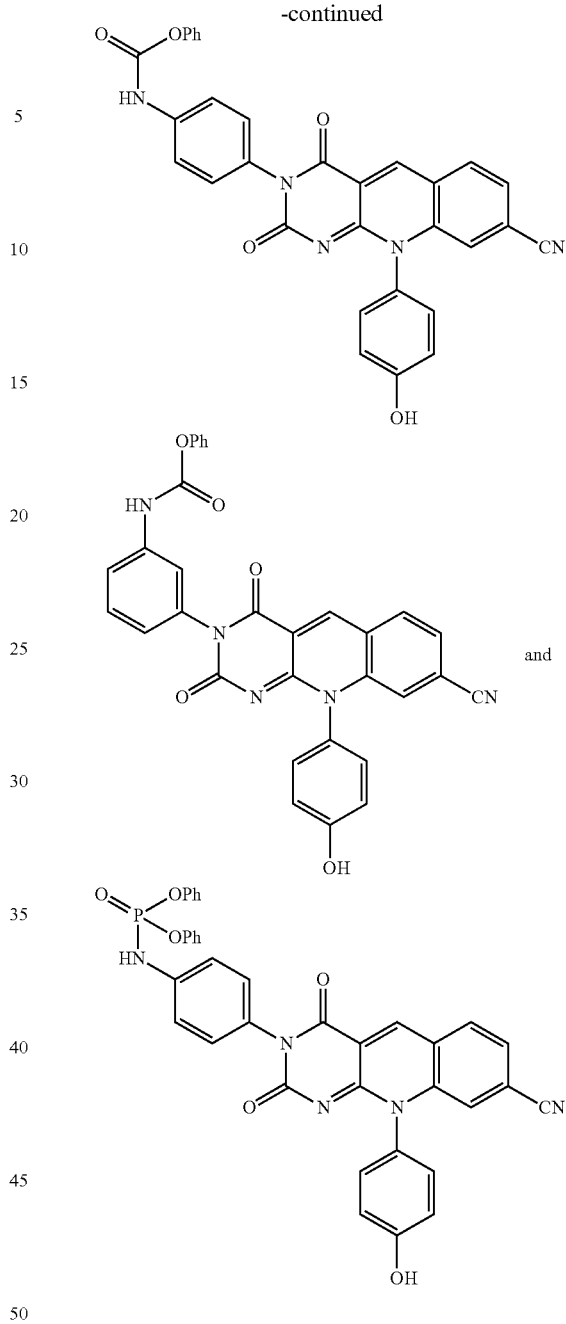

and pharmaceutically acceptable salts thereof.

16. A pharmaceutical composition comprising a compound as described in claim 1 or a pharmaceutically acceptable salt thereof, and a pharmaceutically acceptable excipient.

17. A pharmaceutical composition comprising, 1) a compound as described in claim 1 or a pharmaceutically acceptable salt thereof, 2) a chemotherapeutic agent, and 3) a pharmaceutically acceptable excipient.

* * * * *

UNITED STATES PATENT AND TRADEMARK OFFICE
CERTIFICATE OF CORRECTION

PATENT NO. : 10,617,706 B2  
APPLICATION NO. : 16/267274  
DATED : April 14, 2020  
INVENTOR(S) : Zhengqiang Wang, Jayakanth Kankanala and Yves Pommier Page 1 of 1

It is certified that error appears in the above-identified patent and that said Letters Patent is hereby corrected as shown below:

In the Claims

Column 65, Line 65, Claim 1, please delete "halo($C_1$-$C_6$)alkoxy- carbony" and insert -- halo($C_1$-$C_6$)alkoxycarbonyl, --;

Column 66, Line 11, Claim 1, please delete "($C_1$-$C_6$) alkoxycarbonyl," and insert -- ($C_1$-$C_6$)alkoxycarbonyl, --;

Column 68, Line 47, Claim 8, please delete "salt of claim selected" and insert -- salt of claim 2 selected --;

Column 76, Lines 31-32, Claim 15, please delete "pharmaceutically acceptable of claim 1, selected" and insert -- pharmaceutically acceptable salt of claim 1, selected -- therefor.

Signed and Sealed this  
Twenty-third Day of February, 2021

Drew Hirshfeld  
*Performing the Functions and Duties of the*  
*Under Secretary of Commerce for Intellectual Property and*  
*Director of the United States Patent and Trademark Office*